(12) United States Patent
Chu et al.

(10) Patent No.: US 12,186,215 B2
(45) Date of Patent: *Jan. 7, 2025

(54) LOCKING ASSEMBLY FOR COUPLING GUIDEWIRE TO DELIVERY SYSTEM

(71) Applicant: Endologix LLC, Irvine, CA (US)

(72) Inventors: Kevin Chu, Tustin, CA (US); Rolando Lee, Irvine, CA (US); Craig Welk, Laguna Niguel, CA (US); Bryant Tran, Anaheim, CA (US)

(73) Assignee: Endologix LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/485,100

(22) Filed: Sep. 24, 2021

(65) Prior Publication Data

US 2022/0218503 A1 Jul. 14, 2022

Related U.S. Application Data

(63) Continuation of application No. 15/317,905, filed as application No. PCT/US2016/040197 on Jun. 29, 2016, now Pat. No. 11,129,737.

(Continued)

(51) Int. Cl.
*A61F 2/06* (2013.01)
*A61F 2/954* (2013.01)
(Continued)

(52) U.S. Cl.
CPC ............... *A61F 2/954* (2013.01); *A61F 2/06* (2013.01); *A61F 2/966* (2013.01);
(Continued)

(58) Field of Classification Search
CPC ............ A61M 39/1011; A61M 39/105; A61M 2039/1016; A61M 2205/0216;
(Continued)

(56) References Cited

U.S. PATENT DOCUMENTS

| 519,928 A | 5/1894 | Schanck |
| 1,065,935 A | 7/1913 | Gail |

(Continued)

FOREIGN PATENT DOCUMENTS

| CA | 2007648 | 4/1991 |
| CA | 2127458 | 7/1993 |

(Continued)

OTHER PUBLICATIONS

US 5,690,647 A, 11/1997, Osborne (withdrawn)

(Continued)

*Primary Examiner* — Majid Jamialahmadi
(74) *Attorney, Agent, or Firm* — Foley & Lardner LLP

(57) ABSTRACT

A locking assembly for releasably coupling a first elongate member to a second elongate member is provided. The locking assembly can include a first lumen for anchoring the locking assembly to a catheter and a second lumen for releasably retaining a guidewire to the locking assembly. A release member can interface with the locking assembly and apply a force that decouples the guidewire from the locking assembly.

20 Claims, 40 Drawing Sheets

Related U.S. Application Data

(60) Provisional application No. 62/187,103, filed on Jun. 30, 2015.

(51) Int. Cl.
*A61F 2/966* (2013.01)
*A61M 39/10* (2006.01)
*A61F 2/07* (2013.01)

(52) U.S. Cl.
CPC ...... *A61M 39/1011* (2013.01); *A61M 39/105* (2013.01); *A61F 2002/065* (2013.01); *A61F 2/07* (2013.01); *A61M 2039/1016* (2013.01); *A61M 2205/0216* (2013.01)

(58) Field of Classification Search
CPC .......... A61F 2/969; A61F 2/954; A61F 2/966; A61F 2/95; A61F 2002/011; A61F 2/07; A61F 2002/065; A61B 17/0487; A61B 17/0401; A61B 2017/22049
See application file for complete search history.

(56) References Cited

U.S. PATENT DOCUMENTS

| | | |
|---|---|---|
| 2,127,903 A | 8/1938 | Bowen |
| 2,335,333 A | 11/1943 | Wysong |
| 2,437,542 A | 5/1944 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,245,703 A | 4/1966 | Manly |
| 3,805,301 A | 4/1974 | Liebig |
| 3,994,149 A | 11/1976 | Dahlman |
| 4,362,156 A | 12/1982 | Feller, Jr. et al. |
| 4,402,685 A | 9/1983 | Bühler et al. |
| 4,473,067 A | 9/1984 | Schiff |
| 4,497,074 A | 2/1985 | Ray et al. |
| 4,501,263 A | 2/1985 | Harbuck |
| 4,503,568 A | 3/1985 | Madras |
| 4,512,338 A | 4/1985 | Balko et al. |
| 4,525,157 A | 6/1985 | Vaillancourt |
| 4,562,596 A | 1/1986 | Kornberg |
| 4,580,568 A | 4/1986 | Gianturco |
| 4,592,754 A | 6/1986 | Gupte et al. |
| 4,617,932 A | 10/1986 | Kornberg |
| 4,723,550 A | 2/1988 | Bales et al. |
| 4,723,938 A | 2/1988 | Goodin et al. |
| 4,728,328 A | 3/1988 | Hughes et al. |
| 4,747,833 A | 5/1988 | Kousal et al. |
| 4,756,307 A | 7/1988 | Crownshield |
| 4,768,507 A | 9/1988 | Fischell et al. |
| 4,772,266 A | 9/1988 | Groshong |
| 4,781,690 A | 11/1988 | Ishida et al. |
| 4,795,465 A | 1/1989 | Marten |
| 4,800,882 A | 1/1989 | Gianturco |
| 4,816,028 A | 3/1989 | Kapadia et al. |
| 4,840,940 A | 6/1989 | Sottiural |
| 4,856,516 A | 8/1989 | Hillstead |
| 4,874,374 A | 10/1989 | Kousal et al. |
| 4,878,906 A | 11/1989 | Lindemann et al. |
| 4,888,000 A | 12/1989 | McQuilkin et al. |
| 4,907,336 A | 3/1990 | Gianturco |
| 4,917,668 A | 4/1990 | Haind |
| 4,922,905 A | 5/1990 | Strecker |
| 4,960,412 A | 10/1990 | Fink |
| 4,978,334 A | 12/1990 | Toye et al. |
| 4,981,478 A | 1/1991 | Evard et al. |
| 4,981,947 A | 1/1991 | Tomagou et al. |
| 4,994,069 A | 2/1991 | Ritchrt et al. |
| 4,994,071 A | 2/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,064,414 A | 11/1991 | Revane |
| 5,064,435 A | 11/1991 | Porter |
| 5,078,726 A | 1/1992 | Kreamer |
| 5,084,010 A | 1/1992 | Plaia et al. |
| 5,098,392 A | 3/1992 | Fleischhacker et al. |
| 5,098,395 A | 3/1992 | Fields |
| 5,104,388 A | 4/1992 | Quackenbush |
| 5,104,399 A | 4/1992 | Lazarus |
| 5,108,380 A | 4/1992 | Herlitze et al. |
| 5,108,424 A | 4/1992 | Hoffman, Jr. et al. |
| 5,116,349 A | 5/1992 | Aranyi |
| 5,122,154 A | 6/1992 | Rhodes |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,137,519 A | 8/1992 | Littrell et al. |
| 5,141,497 A | 8/1992 | Erskine |
| 5,151,105 A | 9/1992 | Kwan-Gett |
| 5,156,619 A | 10/1992 | Ehrenfeld |
| 5,158,545 A | 10/1992 | Trudell et al. |
| 5,167,634 A | 12/1992 | Corrigan, Jr. et al. |
| 5,178,634 A | 1/1993 | Martinez |
| 5,186,712 A | 2/1993 | Kelso et al. |
| 5,195,978 A | 3/1993 | Schiffer |
| 5,195,980 A | 3/1993 | Catlin |
| 5,197,976 A | 3/1993 | Herweck et al. |
| 5,201,757 A | 4/1993 | Heyn et al. |
| 5,203,774 A | 4/1993 | Gilson et al. |
| 5,205,829 A | 4/1993 | Lituchy |
| 5,211,658 A | 5/1993 | Clouse |
| 5,222,969 A | 6/1993 | Gillis |
| 5,242,399 A | 9/1993 | Lau et al. |
| 5,246,452 A | 9/1993 | Sinnott |
| 5,250,036 A | 10/1993 | Farivar |
| 5,256,141 A | 10/1993 | Gencheff et al. |
| 5,263,932 A | 11/1993 | Jang |
| 5,267,982 A | 12/1993 | Sylvanowicz |
| 5,273,052 A | 12/1993 | Kraus et al. |
| 5,275,622 A | 1/1994 | Lazarus et al. |
| 5,279,592 A | 1/1994 | Amor et al. |
| 5,282,860 A | 1/1994 | Matsuno et al. |
| 5,282,478 A | 2/1994 | Fleischhaker et al. |
| 5,282,824 A | 2/1994 | Gianturco |
| 5,290,310 A | 3/1994 | Makower et al. |
| 5,304,156 A | 4/1994 | Sylvanowicz et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpeil |
| 5,324,306 A | 6/1994 | Makower et al. |
| 5,330,500 A | 7/1994 | Song |
| 5,334,157 A | 8/1994 | Klein et al. |
| 5,342,387 A | 8/1994 | Summers |
| 5,350,397 A | 9/1994 | Palermo et al. |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,376,077 A | 12/1994 | Gomringer |
| 5,383,892 A | 1/1995 | Cardon et al. |
| 5,387,235 A | 2/1995 | Chuter |
| 5,389,087 A | 2/1995 | Miraki |
| 5,391,152 A | 2/1995 | Patterson |
| 5,397,310 A | 3/1995 | Chu et al. |
| 5,397,355 A | 3/1995 | Marin et al. |
| 5,403,283 A | 4/1995 | Luther |
| 5,403,341 A | 4/1995 | Solar |
| 5,405,323 A | 4/1995 | Rogers et al. |
| 5,405,377 A | 4/1995 | Cragg |
| 5,405,378 A | 4/1995 | Strecker |
| 5,414,664 A | 5/1995 | Lin et al. |
| 5,415,178 A | 5/1995 | Hsl et al. |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |

(56) References Cited

U.S. PATENT DOCUMENTS

| | | |
|---|---|---|
| 5,443,500 A | 8/1995 | Sigwart |
| 5,453,090 A | 9/1995 | Martinez et al. |
| 5,456,713 A | 10/1995 | Chuter |
| 5,458,615 A | 10/1995 | Klemm et al. |
| 5,462,530 A | 10/1995 | Jang |
| 5,464,449 A | 11/1995 | Ryan et al. |
| 5,464,450 A | 11/1995 | Buscemi et al. |
| 5,464,499 A | 11/1995 | Moslehi et al. |
| 5,472,417 A | 12/1995 | Martin et al. |
| 5,484,444 A | 1/1996 | Braunschweller et al. |
| 5,489,295 A | 2/1996 | Piplani et al. |
| 5,496,365 A | 3/1996 | Sgro |
| 5,505,710 A | 4/1996 | Dorsey, III |
| 5,507,727 A | 4/1996 | Crainich |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,882 A | 6/1996 | Gaterud et al. |
| 5,522,883 A | 6/1996 | Slater et al. |
| 5,523,092 A | 6/1996 | Slater et al. |
| 5,545,152 A | 8/1996 | Funderburk et al. |
| 5,545,209 A | 8/1996 | Roberts et al. |
| 5,545,211 A | 8/1996 | An et al. |
| 5,549,635 A | 8/1996 | Solar |
| 5,545,118 A | 9/1996 | Jang |
| 5,554,118 A | 9/1996 | Jang |
| 5,554,181 A | 9/1996 | Das |
| 5,562,697 A | 10/1996 | Christiansen |
| 5,562,724 A | 10/1996 | Vorwerk et al. |
| 5,562,726 A | 10/1996 | Chuter |
| 5,562,728 A | 10/1996 | Lazarus et al. |
| 5,571,135 A | 11/1996 | Fraser et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,817 A | 11/1996 | Martin |
| 5,575,818 A | 11/1996 | Pinchuk |
| 5,578,071 A | 11/1996 | Parodi |
| 5,578,072 A | 11/1996 | Barone et al. |
| 5,591,195 A | 1/1997 | Taheri et al. |
| 5,591,197 A | 1/1997 | Orth et al. |
| 5,591,198 A | 1/1997 | Boyle et al. |
| 5,591,226 A | 1/1997 | Trerotola et al. |
| 5,591,228 A | 1/1997 | Edoga |
| 5,591,229 A | 1/1997 | Parodi |
| 5,591,230 A | 1/1997 | Horn et al. |
| 5,593,417 A | 1/1997 | Rhodes |
| 5,599,305 A | 2/1997 | Hermann et al. |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,755 A | 5/1997 | Heller et al. |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,634,928 A | 6/1997 | Fischell et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,653,748 A | 8/1997 | Strecker |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,666,968 A | 9/1997 | Imran et al. |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,671 A | 10/1997 | Inoue |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,690,671 A | 11/1997 | McGurk et al. |
| 5,693,015 A | 12/1997 | Walker et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,697,971 A | 12/1997 | Fischell et al. |
| 5,700,269 A | 12/1997 | Pinchuk et al. |
| 5,702,418 A | 12/1997 | Ravenscroft |
| 5,707,354 A | 1/1998 | Salmon et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,725,519 A | 3/1998 | Penner et al. |
| 5,733,267 A | 3/1998 | Del Toro |
| 5,733,325 A | 3/1998 | Robinson et al. |
| 5,738,660 A | 4/1998 | Luther |
| 5,738,674 A | 4/1998 | Williams et al. |
| 5,741,233 A | 4/1998 | Riddle et al. |
| 5,741,325 A | 4/1998 | Chalkof et al. |
| 5,746,766 A | 5/1998 | Edoga |
| 5,746,776 A | 5/1998 | Smith et al. |
| 5,749,880 A | 5/1998 | Banas et al. |
| 5,749,921 A | 5/1998 | Lenker et al. |
| 5,755,735 A | 5/1998 | Richter et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,882 A | 6/1998 | Fogarty et al. |
| 5,769,885 A | 6/1998 | Quiachon et al. |
| 5,769,887 A | 6/1998 | Brown et al. |
| 5,772,636 A | 6/1998 | Brimhall et al. |

(56) References Cited

U.S. PATENT DOCUMENTS

| | | |
|---|---|---|
| 5,782,807 A | 6/1998 | Falvai et al. |
| 5,776,142 A | 7/1998 | Gunderson |
| 5,782,817 A | 7/1998 | Franzel et al. |
| 5,782,855 A | 7/1998 | Lau et al. |
| 5,782,909 A | 7/1998 | Quiachon et al. |
| 5,788,707 A | 8/1998 | Del Toro et al. |
| 5,797,952 A | 8/1998 | Klein |
| 5,800,456 A | 9/1998 | Maeda et al. |
| 5,800,508 A | 9/1998 | Goicoechea et al. |
| 5,800,514 A | 9/1998 | Nunez et al. |
| 5,800,517 A | 9/1998 | Anderson et al. |
| 5,800,526 A | 9/1998 | Anderson et al. |
| 5,800,540 A | 9/1998 | Chin |
| 5,810,836 A | 9/1998 | Hussein et al. |
| 5,810,873 A | 9/1998 | Morales |
| 5,817,100 A | 10/1998 | Igaki |
| 5,823,198 A | 10/1998 | Jones et al. |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,053 A | 10/1998 | Khosravi et al. |
| 5,843,046 A | 12/1998 | Motisi et al. |
| 5,843,092 A | 12/1998 | Heller et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,855,600 A | 1/1999 | Alt |
| 5,860,998 A | 1/1999 | Robinson et al. |
| 5,865,844 A | 2/1999 | Plaia et al. |
| 5,867,432 A | 2/1999 | Toda |
| 5,868,783 A | 2/1999 | Tower |
| 5,871,536 A | 2/1999 | Lazarus |
| 5,873,906 A | 2/1999 | Lau et al. |
| 5,876,432 A | 3/1999 | Lau et al. |
| 5,879,321 A | 3/1999 | Hill |
| 5,879,333 A | 3/1999 | Smith |
| 5,879,334 A | 3/1999 | Brimhall |
| 5,879,366 A | 3/1999 | Shaw et al. |
| 5,885,217 A | 3/1999 | Gisselberg et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,619 A | 5/1999 | Olson et al. |
| 5,906,640 A | 5/1999 | Penn et al. |
| 5,906,641 A | 5/1999 | Thompson et al. |
| 5,910,145 A | 6/1999 | Fischell et al. |
| 5,911,710 A | 6/1999 | Barry et al. |
| 5,911,752 A | 6/1999 | Dustrude et al. |
| 5,916,263 A | 6/1999 | Goicocha et al. |
| 5,919,225 A | 7/1999 | Lau et al. |
| 5,925,075 A | 7/1999 | Myers et al. |
| 5,925,076 A | 7/1999 | Inoe |
| 5,928,248 A | 7/1999 | Acker |
| 5,928,279 A | 7/1999 | Shannon et al. |
| 5,935,135 A | 8/1999 | Bramfitt et al. |
| 5,935,161 A | 8/1999 | Robinson et al. |
| 5,938,696 A | 8/1999 | Goicoechea et al. |
| 5,948,017 A | 9/1999 | Taheri |
| 5,948,018 A | 9/1999 | Dereume et al. |
| 5,954,729 A | 9/1999 | Bachmann et al. |
| 5,957,929 A | 9/1999 | Brenneman |
| 5,957,949 A | 9/1999 | Leonhardt et al. |
| 5,957,973 A | 9/1999 | Quiachon et al. |
| 5,961,546 A | 10/1999 | Robinson et al. |
| 5,961,548 A | 10/1999 | Shmulewitz |
| 5,971,958 A | 10/1999 | Zhang |
| 5,976,153 A | 11/1999 | Fischell et al. |
| 5,976,155 A | 11/1999 | Foreman et al. |
| 5,980,514 A | 11/1999 | Kupiecki et al. |
| 5,984,929 A | 11/1999 | Bashiri et al. |
| 5,984,955 A | 11/1999 | Wisselink |
| 5,989,242 A | 11/1999 | Saadat et al. |
| 5,993,489 A | 11/1999 | Lewis et al. |
| 5,997,562 A | 12/1999 | Zadno-Azizi et al. |
| 6,001,125 A | 12/1999 | Golds et al. |
| 6,004,294 A | 12/1999 | Brimhall et al. |
| 6,004,347 A | 12/1999 | McNamara et al. |
| 6,004,348 A | 12/1999 | Banas et al. |
| 6,017,363 A | 1/2000 | Hojelbane |
| 6,019,777 A | 2/2000 | Mackenzie |
| 6,019,785 A | 2/2000 | Strecker |
| 6,027,508 A | 2/2000 | Ren et al. |
| 6,027,520 A | 2/2000 | Tsugita et al. |
| 6,027,779 A | 2/2000 | Campbell et al. |
| 6,027,811 A | 2/2000 | Campbell et al. |
| 6,030,414 A | 2/2000 | Taheri |
| 6,030,415 A | 2/2000 | Chuter |
| 6,033,413 A | 3/2000 | Mikus et al. |
| 6,033,434 A | 3/2000 | Borghi |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,059,824 A | 5/2000 | Taheri |
| 6,063,092 A | 5/2000 | Shin |
| 6,063,113 A | 5/2000 | Kavteladze et al. |
| 6,068,635 A | 5/2000 | Gianotti |
| 6,068,654 A | 5/2000 | Berg et al. |
| 6,070,589 A | 6/2000 | Keith et al. |
| 6,074,398 A | 6/2000 | Leschinsky |
| 6,077,295 A | 6/2000 | Limon et al. |
| 6,077,296 A | 6/2000 | Shokoohl et al. |
| 6,077,297 A | 6/2000 | Robinson et al. |
| 6,080,191 A | 6/2000 | Summers |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,005 A | 8/2000 | Botich et al. |
| 6,096,027 A | 8/2000 | Layne |
| 6,106,548 A | 8/2000 | Reubin et al. |
| 6,110,180 A | 8/2000 | Foreman et al. |
| 6,113,607 A | 9/2000 | Lau et al. |
| 6,117,142 A | 9/2000 | Goodson et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,132,458 A | 10/2000 | Stachle et al. |
| 6,136,006 A | 10/2000 | Johnson et al. |
| 6,139,532 A | 10/2000 | Howell et al. |
| 6,143,002 A | 11/2000 | Vietmeier |
| 6,143,016 A | 11/2000 | Bleam et al. |
| 6,146,389 A | 11/2000 | Geitz |
| 6,146,415 A | 11/2000 | Fitz |
| 6,149,680 A | 11/2000 | Shelso et al. |
| 6,149,681 A | 11/2000 | Houser et al. |
| 6,152,944 A | 11/2000 | Holman et al. |
| 6,156,063 A | 12/2000 | Douglas |
| 6,159,195 A | 12/2000 | Ha et al. |
| 6,159,198 A | 12/2000 | Gardeski et al. |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,174,327 B1 | 1/2001 | Mertens et al. |
| 6,174,329 B1 | 1/2001 | Mertens et al. |
| 6,183,443 B1 | 2/2001 | Kratoska et al. |
| 6,183,481 B1 | 2/2001 | Lee et al. |
| 6,183,509 B1 | 2/2001 | Dible |
| 6,187,015 B1 | 2/2001 | Brenneman |
| 6,187,033 B1 | 2/2001 | Schmitt et al. |

(56) References Cited

U.S. PATENT DOCUMENTS

| | | |
|---|---|---|
| 6,187,036 B1 | 2/2001 | Shaollan et al. |
| 6,187,037 B1 | 2/2001 | Satz |
| 6,192,944 B1 | 2/2001 | Greenhalgh |
| 6,193,726 B1 | 2/2001 | Vanney |
| 6,193,745 B1 | 2/2001 | Fogarty et al. |
| 6,197,007 B1 | 3/2001 | Thorne et al. |
| 6,197,016 B1 | 3/2001 | Fourkas et al. |
| 6,197,049 B1 | 3/2001 | Shaollan et al. |
| 6,203,735 B1 | 3/2001 | Edwin et al. |
| 6,210,422 B1 | 4/2001 | Douglas |
| 6,210,429 B1 | 4/2001 | Vardi et al. |
| 6,214,038 B1 | 4/2001 | Piplani et al. |
| 6,221,081 B1 | 4/2001 | Mikus et al. |
| 6,221,090 B1 | 4/2001 | Wilson |
| 6,221,098 B1 | 4/2001 | Wilsor |
| 6,221,102 B1 | 4/2001 | Baker et al. |
| 6,224,609 B1 | 5/2001 | Ressemann et al. |
| 6,224,627 B1 | 5/2001 | Armstrong et al. |
| 6,228,062 B1 | 5/2001 | Howell et al. |
| 6,231,543 B1 * | 5/2001 | Hegde .............. A61M 25/10 606/192 |
| 6,231,563 B1 | 5/2001 | White et al. |
| 6,235,051 B1 | 5/2001 | Murphy |
| 6,238,410 B1 | 5/2001 | Vrba et al. |
| 6,254,609 B1 | 7/2001 | Vrba et al. |
| 6,254,628 B1 | 7/2001 | Wallace et al. |
| 6,258,099 B1 | 7/2001 | Mareiro et al. |
| 6,261,316 B1 | 7/2001 | Shaollan et al. |
| 6,264,682 B1 | 7/2001 | Wilson et al. |
| 6,273,895 B1 | 8/2001 | Pinchuk et al. |
| 6,273,909 B1 | 8/2001 | Kugler et al. |
| 6,280,465 B1 | 8/2001 | Cryer |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,315 B1 | 9/2001 | Wijeratne et al. |
| 6,287,329 B1 | 9/2001 | Duering et al. |
| 6,296,622 B1 | 10/2001 | Kurz et al. |
| 6,299,634 B1 | 10/2001 | Bergeron |
| 6,302,893 B1 | 10/2001 | Limon et al. |
| 6,312,406 B1 | 11/2001 | Jayaraman |
| 6,315,792 B1 | 11/2001 | Armstrong et al. |
| 6,325,826 B1 | 12/2001 | Vardi et al. |
| 6,331,184 B1 | 12/2001 | Abrams |
| 6,331,190 B1 | 12/2001 | Shokoohl et al. |
| 6,334,867 B1 | 1/2002 | Anson |
| 6,344,056 B1 | 2/2002 | Dehdashtian |
| 6,346,118 B1 | 2/2002 | Baker et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,554 B2 | 3/2002 | De Paulis |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,557 B1 | 3/2002 | Gittings et al. |
| 6,361,559 B1 | 3/2002 | Houser et al. |
| 6,361,637 B2 | 3/2002 | Martin et al. |
| 6,379,365 B1 | 4/2002 | Diaz |
| 6,380,457 B1 | 4/2002 | Yurek et al. |
| 6,383,213 B2 | 5/2002 | Wilson et al. |
| 6,387,120 B2 | 5/2002 | Wilson et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,529 B1 | 7/2002 | Holman et al. |
| 6,416,542 B1 | 7/2002 | Marcade et al. |
| 6,425,765 B1 | 7/2002 | Irwin, III |
| 6,428,565 B1 | 8/2002 | Wisselink |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,436,135 B1 | 8/2002 | Goldfarb |
| 6,440,161 B1 | 8/2002 | Madrid et al. |
| 6,447,540 B1 | 9/2002 | Fontaine et al. |
| 6,451,043 B1 | 9/2002 | McInnes et al. |
| 6,482,211 B1 | 9/2002 | Choi |
| 6,458,152 B1 | 10/2002 | Khosravi et al. |
| 6,464,721 B1 | 10/2002 | Marcade et al. |
| 6,468,298 B1 | 10/2002 | Pelton |
| 6,475,166 B1 | 11/2002 | Escano |
| 6,475,170 B1 | 11/2002 | Doron et al. |
| 6,478,777 B1 | 11/2002 | Honeck et al. |
| 6,485,513 B1 | 11/2002 | Fan |
| 6,491,719 B1 | 12/2002 | Fogrty et al. |
| 6,500,182 B2 | 12/2002 | Foster |
| 6,500,202 B1 | 12/2002 | Shaollan et al. |
| 6,508,790 B1 | 1/2003 | Lawrence |
| 6,508,833 B2 | 1/2003 | Pavonick et al. |
| 6,508,835 B1 | 1/2003 | Shaollan et al. |
| 6,508,836 B2 | 1/2003 | Wilson et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,522 B1 | 2/2003 | Bell et al. |
| 6,517,569 B2 | 2/2003 | Mikus et al. |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,524,336 B1 | 2/2003 | Papazolgou et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,554,848 B2 | 4/2003 | Boylan et al. |
| 6,558,396 B1 | 5/2003 | Inoue |
| 6,562,063 B1 | 5/2003 | Euteneurer et al. |
| 6,562,064 B1 | 5/2003 | Debeer |
| 6,565,596 B1 | 5/2003 | White et al. |
| 6,565,597 B1 | 5/2003 | Fearnot et al. |
| 6,569,192 B1 | 5/2003 | Foreman et al. |
| RE38,146 E | 6/2003 | Palmaz et al. |
| 6,572,643 B1 | 6/2003 | Gharibadeh |
| 6,572,645 B2 | 6/2003 | Leonhardt |
| 6,576,005 B1 | 6/2003 | Geitz |
| 6,576,006 B2 | 6/2003 | Limon et al. |
| 6,576,009 B2 | 6/2003 | Ryan et al. |
| 6,579,308 B1 | 6/2003 | Jansen et al. |
| 6,579,312 B2 | 6/2003 | Wilson et al. |
| 6,582,390 B1 | 6/2003 | Sanderson |
| 6,582,394 B1 | 6/2003 | Reiss et al. |
| 6,582,459 B1 | 6/2003 | Lau et al. |
| 6,582,460 B1 | 6/2003 | Cryer |
| 6,585,758 B1 | 7/2003 | Chouinard et al. |
| 6,589,213 B2 | 7/2003 | Reydel |
| 6,589,251 B2 | 7/2003 | Yee et al. |
| 6,589,262 B1 | 7/2003 | Honebrink et al. |
| 6,592,548 B2 | 7/2003 | Jayaraman |
| 6,592,581 B2 | 7/2003 | Bowe |
| 6,592,614 B2 | 7/2003 | Lenker et al. |
| 6,592,615 B1 | 7/2003 | Marcade et al. |
| 6,599,315 B2 | 7/2003 | Wilson |
| 6,602,280 B2 | 8/2003 | Chobotov |
| 6,607,551 B1 | 8/2003 | Sullivan et al. |
| 6,607,552 B1 | 8/2003 | Hanson |
| 6,613,073 B1 | 9/2003 | White et al. |
| 6,613,075 B1 | 9/2003 | Healy et al. |
| 6,616,675 B1 | 9/2003 | Evard et al. |
| 6,620,191 B1 | 9/2003 | Svensson |
| 6,641,564 B1 | 11/2003 | Kraus |
| 6,645,242 B1 | 11/2003 | Quinn |
| 6,652,492 B1 | 11/2003 | Bell et al. |
| 6,652,567 B1 | 11/2003 | Deaton |
| 6,652,579 B1 | 11/2003 | Cox et al. |
| 6,656,213 B2 | 12/2003 | Solem |
| 6,660,030 B2 | 12/2003 | Shaolian et al. |
| 6,660,033 B1 | 12/2003 | Marcade et al. |
| 6,663,665 B2 | 12/2003 | Shaolian et al. |

(56) References Cited

U.S. PATENT DOCUMENTS

| | | |
|---|---|---|
| 6,669,716 B1 | 12/2003 | Gilson et al. |
| 6,669,718 B2 | 12/2003 | Besselink |
| 6,669,719 B2 | 12/2003 | Wallace et al. |
| 6,673,102 B1 | 1/2004 | Vonesh et al. |
| 6,676,666 B2 | 1/2004 | Vrba et al. |
| 6,676,667 B2 | 1/2004 | Mareiro et al. |
| 6,689,157 B2 | 2/2004 | Madrid et al. |
| 6,692,483 B2 | 2/2004 | Vardi et al. |
| 6,695,875 B2 | 2/2004 | Stelter et al. |
| 6,699,274 B2 | 3/2004 | Stinson |
| 6,699,275 B1 | 3/2004 | Knudson et al. |
| 6,702,843 B1 | 3/2004 | Brown et al. |
| 6,702,845 B1 | 3/2004 | Cully et al. |
| 6,706,062 B2 | 3/2004 | Vardi et al. |
| 6,722,705 B2 | 4/2004 | Korkor |
| 6,723,075 B2 | 4/2004 | Davey et al. |
| 6,723,116 B2 | 4/2004 | Taheri |
| 6,733,523 B2 | 5/2004 | Shaollan et al. |
| 6,740,101 B2 | 5/2004 | Houser et al. |
| 6,743,210 B2 | 6/2004 | Hart et al. |
| 6,749,627 B2 | 6/2004 | Thompson et al. |
| 6,752,819 B1 | 6/2004 | Brady et al. |
| 6,755,855 B2 | 6/2004 | Yurek et al. |
| 6,761,733 B2 | 7/2004 | Chobotov et al. |
| 6,767,359 B2 | 7/2004 | Weadock |
| 6,773,457 B2 | 8/2004 | Ivancev et al. |
| 6,790,224 B2 | 9/2004 | Gerberding |
| 6,793,671 B2 | 9/2004 | Wall |
| 6,800,065 B2 | 10/2004 | Duane et al. |
| 6,802,859 B1 | 10/2004 | Pazienza et al. |
| 6,808,509 B1 | 10/2004 | Davey |
| 6,808,520 B1 | 10/2004 | Fourkas et al. |
| 6,811,566 B1 | 11/2004 | Penn et al. |
| 6,814,752 B1 | 11/2004 | Chuter |
| 6,818,014 B2 | 11/2004 | Brown et al. |
| 6,821,292 B2 | 11/2004 | Pazienza et al. |
| 6,827,706 B2 | 12/2004 | Parodi |
| 6,827,726 B2 | 12/2004 | Parodi |
| 6,827,731 B2 | 12/2004 | Armstrong et al. |
| 6,833,003 B2 | 12/2004 | Jones et al. |
| 6,835,203 B1 | 12/2004 | Vardi et al. |
| 6,840,950 B2 | 1/2005 | Standford et al. |
| 6,846,316 B2 | 1/2005 | Abrams |
| 6,849,084 B2 | 2/2005 | Rabkin et al. |
| 6,849,086 B2 | 2/2005 | Cragg |
| 6,858,038 B2 | 2/2005 | Heuser |
| 6,866,669 B2 | 3/2005 | Buzzard et al. |
| 6,872,193 B2 | 3/2005 | Shaw et al. |
| 6,875,229 B2 | 4/2005 | Wilson et al. |
| 6,878,158 B2 | 4/2005 | Shin et al. |
| 6,887,249 B1 | 5/2005 | Houser et al. |
| 6,887,251 B1 | 5/2005 | Suval |
| 6,887,256 B2 | 5/2005 | Gilson et al. |
| 6,889,026 B2 | 5/2005 | Schlageter et al. |
| 6,896,699 B2 | 5/2005 | Wilson et al. |
| 6,899,727 B2 | 5/2005 | Armstrong et al. |
| 6,899,728 B1 | 5/2005 | Phillips et al. |
| 6,905,505 B2 | 6/2005 | Nash et al. |
| 6,908,477 B2 | 6/2005 | McGuckin |
| 6,911,039 B2 | 6/2005 | Shiu et al. |
| 6,918,925 B2 | 7/2005 | Tehrani |
| 6,923,829 B2 | 8/2005 | Boyle et al. |
| 6,926,732 B2 | 8/2005 | Derus et al. |
| 6,929,661 B2 | 8/2005 | Bolduc et al. |
| 6,932,837 B2 | 8/2005 | Amplatz et al. |
| 6,939,327 B2 | 9/2005 | Hall et al. |
| 6,939,352 B2 | 9/2005 | Buzzard et al. |
| 6,939,368 B2 | 9/2005 | Simso |
| 6,939,370 B2 | 9/2005 | Hartley et al. |
| 6,939,371 B2 | 9/2005 | Kugler et al. |
| 6,939,377 B2 | 9/2005 | Jayaraman et al. |
| 6,942,691 B1 | 9/2005 | Chuter |
| 6,942,692 B2 | 9/2005 | Landau et al. |
| 6,942,693 B2 | 9/2005 | Chouinard et al. |
| 6,945,990 B2 | 9/2005 | Greenean |
| 6,948,017 B2 | 9/2005 | Carpenter et al. |
| 6,951,572 B1 | 10/2005 | Douglas |
| 6,953,475 B2 | 10/2005 | Shaolian et al. |
| 6,955,679 B1 | 10/2005 | Hendricksen et al. |
| 6,955,688 B2 | 10/2005 | Wilson et al. |
| 6,960,217 B2 | 11/2005 | Bolduc |
| 6,962,602 B2 | 11/2005 | Vardi |
| 6,974,471 B2 | 12/2005 | Van Schie et al. |
| 6,981,982 B2 | 1/2006 | Armstrong et al. |
| 6,984,244 B2 | 1/2006 | Perez et al. |
| 6,989,024 B2 | 1/2006 | Hebert et al. |
| 6,989,026 B2 | 1/2006 | Richter et al. |
| 6,991,639 B2 | 1/2006 | Holman et al. |
| 6,994,721 B2 | 2/2006 | Israel |
| 6,994,722 B2 | 2/2006 | DiCarlo |
| 7,004,926 B2 | 2/2006 | Navia et al. |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,022,133 B2 | 4/2006 | Yee et al. |
| 7,025,773 B2 | 4/2006 | Gittings et al. |
| 7,025,779 B2 | 4/2006 | Elliott |
| 7,029,494 B2 | 4/2006 | Soun et al. |
| 7,029,496 B2 | 4/2006 | Rakos et al. |
| 7,052,511 B2 | 5/2006 | Weldon et al. |
| 7,056,323 B2 | 6/2006 | Mareiro et al. |
| 7,074,235 B1 | 7/2006 | Roy |
| 7,074,236 B2 | 7/2006 | Rabkin et al. |
| 7,096,554 B2 | 8/2006 | Austin et al. |
| 7,101,390 B2 | 9/2006 | Nelson |
| 7,105,015 B2 | 9/2006 | Goshgarian |
| 7,105,016 B2 | 9/2006 | Shiu et al. |
| 7,105,017 B2 | 9/2006 | Kerr |
| 7,105,020 B2 | 9/2006 | Greenberg et al. |
| 7,118,593 B2 | 10/2006 | Davidson et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,127,789 B2 | 10/2006 | Stinson |
| 7,131,991 B2 | 11/2006 | Zarins et al. |
| 7,137,993 B2 | 11/2006 | Acosta et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,172,577 B2 | 2/2007 | Mangano et al. |
| 7,175,651 B2 | 2/2007 | Kerr |
| 7,175,652 B2 | 2/2007 | Cook et al. |
| 7,175,657 B2 | 2/2007 | Khan et al. |
| 7,189,256 B2 | 3/2007 | Smith |
| 7,189,257 B2 | 3/2007 | Schmitt et al. |
| 7,195,648 B2 | 3/2007 | Jones et al. |
| 7,201,770 B2 | 4/2007 | Johnson et al. |
| 7,220,274 B1 | 5/2007 | Quinn |
| 7,220,275 B2 | 5/2007 | Davidson et al. |
| 7,220,276 B1 | 5/2007 | Williams et al. |
| 7,229,472 B2 | 6/2007 | DePalma et al. |
| 7,232,449 B2 | 6/2007 | Sharkawy et al. |
| 7,235,095 B2 | 6/2007 | Haverkost et al. |
| 7,237,552 B2 | 7/2007 | Khera et al. |
| 7,241,300 B2 | 7/2007 | Sharkawy et al. |
| 7,241,308 B2 | 7/2007 | Andreas et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,294,145 B2 | 11/2007 | Ward |
| 7,297,156 B2 | 11/2007 | Nelson |
| 7,300,454 B2 | 11/2007 | Park et al. |
| 7,300,460 B2 | 11/2007 | Levine et al. |
| 7,306,623 B2 | 12/2007 | Watson |
| 7,309,351 B2 | 12/2007 | Escamilla et al. |
| 7,314,481 B2 | 1/2008 | Karpiel |
| 7,314,483 B2 | 1/2008 | Landau et al. |
| 7,316,708 B2 | 1/2008 | Gordon et al. |
| 7,320,703 B2 | 1/2008 | DiMatteo et al. |

(56) References Cited

U.S. PATENT DOCUMENTS

| | | |
|---|---|---|
| 7,331,980 B2 | 2/2008 | Dubrul et al. |
| 7,341,598 B2 | 3/2008 | Davidson et al. |
| 7,367,980 B2 | 5/2008 | Kida et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,381,216 B2 | 6/2008 | Buzzard et al. |
| 7,402,168 B2 | 7/2008 | Acosta et al. |
| 7,402,171 B2 | 7/2008 | Osborne et al. |
| 7,407,509 B2 | 8/2008 | Greenberg et al. |
| 7,413,560 B2 | 8/2008 | Chong et al. |
| 7,413,573 B2 | 8/2008 | Hartley et al. |
| 7,419,501 B2 | 9/2008 | Chiu et al. |
| 7,425,219 B2 | 9/2008 | Quadri et al. |
| 7,435,253 B1 | 10/2008 | Hartley et al. |
| 7,438,721 B2 | 10/2008 | Doig et al. |
| 7,473,271 B2 | 1/2009 | Gunderson |
| 7,476,244 B2 | 1/2009 | Buzzard et al. |
| 7,481,805 B2 | 1/2009 | Magnusson |
| 7,491,230 B2 | 2/2009 | Holman et al. |
| 7,491,232 B2 | 2/2009 | Bolduc et al. |
| 7,520,890 B2 | 4/2009 | Phillips |
| 7,520,895 B2 | 4/2009 | Douglas et al. |
| 7,526,849 B2 | 5/2009 | Serrano |
| 7,527,636 B2 | 5/2009 | Dunfee et al. |
| 7,537,606 B2 | 5/2009 | Hartley |
| 7,553,324 B2 | 6/2009 | Andreas et al. |
| 7,572,289 B2 | 8/2009 | Sisken et al. |
| 7,575,590 B2 | 8/2009 | Watson |
| 7,578,838 B2 | 8/2009 | Melsheimer |
| 7,578,841 B2 | 8/2009 | Yadin et al. |
| 7,582,111 B2 | 9/2009 | Krolik et al. |
| 7,591,832 B2 | 9/2009 | Eversull et al. |
| 7,591,843 B1 | 9/2009 | Escano et al. |
| 7,611,529 B2 | 11/2009 | Greenberg et al. |
| 7,615,072 B2 | 11/2009 | Rust et al. |
| 7,618,398 B2 | 11/2009 | Holman et al. |
| 7,632,299 B2 | 12/2009 | Weber |
| 7,635,382 B2 | 12/2009 | Pryor |
| 7,635,383 B2 | 12/2009 | Gumm |
| 7,637,932 B2 | 12/2009 | Bolduc et al. |
| 7,641,684 B2 | 1/2010 | Hilaire et al. |
| 7,645,298 B2 | 1/2010 | Hartley et al. |
| 7,651,519 B2 | 1/2010 | Dittman |
| 7,666,219 B2 | 2/2010 | Rasmussen et al. |
| 7,670,316 B2 | 3/2010 | Windheuser et al. |
| 7,670,369 B2 | 3/2010 | Shaeffer et al. |
| 7,674,284 B2 | 3/2010 | Melsheimer |
| 7,678,141 B2 | 3/2010 | Greenan et al. |
| 7,691,135 B2 | 4/2010 | Shaollan et al. |
| 7,691,139 B2 | 4/2010 | Baker et al. |
| 7,695,508 B2 | 4/2010 | Van Der Leest et al. |
| 7,699,885 B2 | 4/2010 | Leonhardt et al. |
| 7,708,771 B2 | 5/2010 | Chuter et al. |
| 7,708,773 B2 | 5/2010 | Pinchuk et al. |
| 7,713,261 B2 | 5/2010 | Nash et al. |
| 7,717,923 B2 | 5/2010 | Kennedy, II et al. |
| 7,722,657 B2 | 5/2010 | Hartley |
| 7,736,337 B2 | 6/2010 | Diep et al. |
| 7,736,383 B2 | 6/2010 | Bressler et al. |
| 7,736,384 B2 | 6/2010 | Bressler et al. |
| 7,753,951 B2 | 7/2010 | Shaked et al. |
| 7,758,625 B2 | 7/2010 | Wu et al. |
| 7,758,633 B2 | 7/2010 | Nazzaro |
| 7,763,063 B2 | 7/2010 | Arbefeuille et al. |
| 7,766,952 B2 | 8/2010 | Horan et al. |
| 7,766,961 B2 | 8/2010 | Patel et al. |
| 7,771,463 B2 | 8/2010 | Ton et al. |
| 7,771,465 B2 | 8/2010 | Zukowski |
| 7,785,340 B2 | 8/2010 | Heidner et al. |
| 7,785,361 B2 | 8/2010 | Nikolchev et al. |
| 7,794,473 B2 | 9/2010 | Tessmer et al. |
| 7,799,266 B2 | 9/2010 | Parker et al. |
| 7,806,917 B2 | 10/2010 | Xiao |
| 7,815,601 B2 | 10/2010 | Jordan et al. |
| 7,815,661 B2 | 10/2010 | Mirizzi et al. |
| 7,828,837 B2 | 11/2010 | Khoury |
| 7,833,202 B2 | 11/2010 | Suzuki |
| 7,833,259 B2 | 11/2010 | Boatman |
| 7,837,724 B2 | 11/2010 | Keeble et al. |
| 7,842,066 B2 | 11/2010 | Gilson et al. |
| 7,846,135 B2 | 12/2010 | Runfola |
| 7,867,267 B2 | 1/2011 | Sullivan et al. |
| 7,867,270 B2 | 1/2011 | Hartley |
| 7,871,419 B2 | 1/2011 | Devellian et al. |
| 7,871,430 B2 | 1/2011 | Pavcnik et al. |
| 7,879,081 B2 | 2/2011 | DeMatteo et al. |
| 7,883,537 B2 | 2/2011 | Grayzel et al. |
| 7,892,275 B2 | 2/2011 | Hartley et al. |
| 7,892,277 B2 | 2/2011 | Douglas et al. |
| 7,909,873 B2 | 3/2011 | Tan-Malecki et al. |
| 7,914,572 B2 | 3/2011 | Hartley et al. |
| 7,922,755 B2 | 4/2011 | Acosta et al. |
| 7,935,140 B2 | 5/2011 | Griffin |
| 7,942,924 B1 | 5/2011 | Perez et al. |
| 7,993,389 B2 | 8/2011 | Globerman |
| 8,002,814 B2 | 8/2011 | Kennedy, II et al. |
| 8,021,420 B2 | 9/2011 | Dolan |
| 8,025,692 B2 | 9/2011 | Feeser |
| 8,034,100 B2 | 10/2011 | Shaolian et al. |
| 8,062,344 B2 | 11/2011 | Dorn et al. |
| 8,075,607 B2 | 12/2011 | Melsheimer |
| 8,075,608 B2 | 12/2011 | Gordon et al. |
| 8,092,508 B2 | 1/2012 | Leynov et al. |
| 8,118,856 B2 | 2/2012 | Schreck et al. |
| 8,147,427 B2 | 4/2012 | Nanto et al. |
| 8,152,830 B2 | 4/2012 | Gumm |
| 8,167,892 B2 | 5/2012 | Feller, III et al. |
| 8,182,522 B2 | 5/2012 | Sarac et al. |
| 8,216,295 B2 | 7/2012 | Bemjamin et al. |
| 8,221,494 B2 | 7/2012 | Schreck et al. |
| 8,236,040 B2 | 8/2012 | Mayberry et al. |
| 8,343,204 B2 | 1/2013 | Osborne |
| 8,357,192 B2 | 1/2013 | Mayberry et al. |
| 8,491,646 B2 | 7/2013 | Schreck |
| 8,523,931 B2 | 9/2013 | Mayberry et al. |
| 8,568,466 B2 | 10/2013 | Shaollan et al. |
| 8,672,989 B2 | 3/2014 | Schreck et al. |
| 8,764,812 B2 | 7/2014 | Mayberry et al. |
| 8,808,350 B2 | 8/2014 | Schreck et al. |
| 8,821,564 B2 | 9/2014 | Schreck et al. |
| 8,828,074 B2 | 9/2014 | Xiao et al. |
| 8,844,430 B2 | 9/2014 | Mastropasqua et al. |
| 8,845,708 B2 | 9/2014 | Hartley et al. |
| 8,945,202 B2 | 2/2015 | Mayberry et al. |
| 9,149,381 B2 | 10/2015 | Schreck et al. |
| 2001/0003161 A1 | 6/2001 | Vardi et al. |
| 2001/0014823 A1 | 8/2001 | Ressemann |
| 2001/0016767 A1 | 8/2001 | Wilson et al. |
| 2001/0025195 A1 | 9/2001 | Shaollan et al. |
| 2001/0027338 A1 | 10/2001 | Greenberg |
| 2001/0037142 A1 | 11/2001 | Stelter et al. |
| 2001/0039445 A1 | 11/2001 | Hall et al. |
| 2001/0049547 A1 | 12/2001 | Moore |
| 2002/0019660 A1 | 2/2002 | Gianotti |
| 2002/0029077 A1 | 3/2002 | Leopold et al. |
| 2002/0042650 A1 | 4/2002 | Vardi et al. |
| 2002/0049412 A1 | 4/2002 | Madrid et al. |
| 2002/0052648 A1 | 5/2002 | McGuckin et al. |
| 2002/0120322 A1 | 8/2002 | Thompson et al. |
| 2002/0123786 A1 | 9/2002 | Gittings et al. |
| 2002/0138088 A1 | 9/2002 | Nash et al. |
| 2002/0143383 A1 | 10/2002 | Parodi |
| 2002/0147491 A1 | 10/2002 | Khan et al. |
| 2002/0156516 A1 | 10/2002 | Vardi |
| 2002/0156518 A1 | 10/2002 | Tehrani |
| 2002/0173835 A1 | 11/2002 | Bourang et al. |
| 2002/0193806 A1 | 12/2002 | Moenning et al. |
| 2002/0193872 A1 | 12/2002 | Trout et al. |
| 2002/0198585 A1 | 12/2002 | Wisselink |
| 2003/0004560 A1 | 1/2003 | Chobotov et al. |
| 2003/0004561 A1 | 1/2003 | Bigus et al. |
| 2003/0028233 A1 | 2/2003 | Vardi et al. |
| 2003/0065386 A1 | 4/2003 | Weadock |

(56) References Cited

U.S. PATENT DOCUMENTS

| | | |
|---|---|---|
| 2003/0074043 A1 | 4/2003 | Thompson |
| 2003/0083678 A1 | 5/2003 | Herweck et al. |
| 2003/0083730 A1 | 5/2003 | Stinson |
| 2003/0083738 A1 | 5/2003 | Holman et al. |
| 2003/0093027 A1* | 5/2003 | McGuckin, Jr. ............... A61M 25/09041 604/8 |
| 2003/0097169 A1 | 5/2003 | Brucker et al. |
| 2003/0100943 A1 | 5/2003 | Bolduc |
| 2003/0125751 A1 | 7/2003 | Griffin et al. |
| 2003/0130721 A1 | 7/2003 | Martin et al. |
| 2003/0167060 A1 | 9/2003 | Buzzard et al. |
| 2003/0167083 A1 | 9/2003 | Lashinski et al. |
| 2003/0176910 A1 | 9/2003 | Vrba et al. |
| 2003/0225445 A1 | 12/2003 | Derus et al. |
| 2003/0236564 A1 | 12/2003 | Majercak |
| 2003/0236565 A1 | 12/2003 | DiMatteo et al. |
| 2003/0236566 A1 | 12/2003 | Heuser |
| 2004/0006380 A1 | 1/2004 | Buck et al. |
| 2004/0015150 A1 | 1/2004 | Zadno-Azizi |
| 2004/0039400 A1 | 2/2004 | Schmieding et al. |
| 2004/0044395 A1 | 3/2004 | Nelson |
| 2004/0049204 A1 | 3/2004 | Harari et al. |
| 2004/0049257 A1 | 3/2004 | Kaspersen et al. |
| 2004/0073288 A1 | 4/2004 | Kerr |
| 2004/0093058 A1 | 5/2004 | Cottone et al. |
| 2004/0098084 A1 | 5/2004 | Hartley et al. |
| 2004/0098096 A1 | 5/2004 | Eton |
| 2004/0106972 A1 | 6/2004 | Deaton |
| 2004/0111095 A1 | 6/2004 | Gordon et al. |
| 2004/0127975 A1 | 7/2004 | Levine et al. |
| 2004/0143312 A1 | 7/2004 | Samson et al. |
| 2004/0176832 A1 | 9/2004 | Hartley et al. |
| 2004/0193180 A1 | 9/2004 | Buzzard et al. |
| 2004/0193254 A1 | 9/2004 | Greenberg et al. |
| 2004/0215312 A1 | 10/2004 | Andreas |
| 2004/0215327 A1 | 10/2004 | Doig et al. |
| 2004/0225344 A1 | 11/2004 | Hoffa et al. |
| 2004/0230286 A1 | 11/2004 | Moore et al. |
| 2004/0230287 A1 | 11/2004 | Hartley et al. |
| 2004/0236403 A1 | 11/2004 | Leonhardt et al. |
| 2005/0015135 A1 | 1/2005 | Shanley |
| 2005/0021123 A1 | 1/2005 | Dorn et al. |
| 2005/0027305 A1 | 2/2005 | Shiu et al. |
| 2005/0027345 A1 | 2/2005 | Horan et al. |
| 2005/0033403 A1 | 2/2005 | Ward et al. |
| 2005/0033405 A1 | 2/2005 | Solovay |
| 2005/0038494 A1 | 2/2005 | Eldenschink |
| 2005/0038495 A1 | 2/2005 | Greenan |
| 2005/0049607 A1 | 3/2005 | Hart et al. |
| 2005/0049667 A1 | 3/2005 | Arbefeuille et al. |
| 2005/0049672 A1 | 3/2005 | Murphy |
| 2005/0049674 A1 | 3/2005 | Berra et al. |
| 2005/0049678 A1 | 3/2005 | Cocks et al. |
| 2005/0058327 A1 | 3/2005 | Pieper |
| 2005/0059923 A1 | 3/2005 | Gamboa |
| 2005/0059994 A1 | 3/2005 | Walak et al. |
| 2005/0060016 A1 | 3/2005 | Wu et al. |
| 2005/0060025 A1 | 3/2005 | Mackiewicz et al. |
| 2005/0060026 A1 | 3/2005 | Gamboa |
| 2005/0075647 A1 | 4/2005 | Walters et al. |
| 2005/0080476 A1 | 4/2005 | Gunderson et al. |
| 2005/0085845 A1 | 4/2005 | Hilaire et al. |
| 2005/0085891 A1 | 4/2005 | Goto et al. |
| 2005/0102018 A1 | 5/2005 | Carpenter et al. |
| 2005/0113693 A1 | 5/2005 | Smith et al. |
| 2005/0113853 A1 | 5/2005 | Noriega et al. |
| 2005/0113905 A1 | 5/2005 | Greenberg et al. |
| 2005/0119719 A1 | 6/2005 | Wallace et al. |
| 2005/0119731 A1 | 6/2005 | Brucker et al. |
| 2005/0121043 A1 | 6/2005 | Abrams |
| 2005/0121120 A1 | 6/2005 | Van Dijk et al. |
| 2005/0125002 A1 | 6/2005 | Baran et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131526 A1 | 6/2005 | Wong |
| 2005/0149166 A1 | 7/2005 | Schaeffer et al. |
| 2005/0154441 A1 | 7/2005 | Schaeffer et al. |
| 2005/0154444 A1 | 7/2005 | Quadri |
| 2005/0159803 A1 | 7/2005 | Lad et al. |
| 2005/0165470 A1 | 7/2005 | Weber |
| 2005/0165480 A1 | 7/2005 | Jordan et al. |
| 2005/0171597 A1 | 8/2005 | Boatman et al. |
| 2005/0171598 A1 | 8/2005 | Schaeffer |
| 2005/0171599 A1 | 8/2005 | White |
| 2005/0177221 A1 | 8/2005 | Mustapha |
| 2005/0182476 A1 | 8/2005 | Hartley et al. |
| 2005/0215327 A1 | 9/2005 | Weisel et al. |
| 2005/0216043 A1 | 9/2005 | Blatter et al. |
| 2005/0222668 A1 | 10/2005 | Schaeffer et al. |
| 2005/0228480 A1 | 10/2005 | Douglas et al. |
| 2005/0240153 A1 | 10/2005 | Opie |
| 2005/0240255 A1 | 10/2005 | Schaeffer |
| 2005/0240258 A1 | 10/2005 | Bolduc et al. |
| 2005/0240260 A1 | 10/2005 | Bolduc |
| 2005/0246008 A1 | 11/2005 | Hogendijk |
| 2005/0273150 A1 | 12/2005 | Howel et al. |
| 2005/0288772 A1 | 12/2005 | Douglas et al. |
| 2006/0018948 A1 | 1/2006 | Guire et al. |
| 2006/0020320 A1 | 1/2006 | Shaolian et al. |
| 2006/0036315 A1 | 2/2006 | Yadin et al. |
| 2006/0052750 A1 | 3/2006 | Lenker et al. |
| 2006/0058864 A1 | 3/2006 | Schaeffer et al. |
| 2006/0089704 A1 | 4/2006 | Douglas |
| 2006/0095050 A1 | 5/2006 | Hartley et al. |
| 2006/0100658 A1 | 5/2006 | Obana et al. |
| 2006/0129223 A1 | 6/2006 | Jabbour et al. |
| 2006/0142704 A1 | 6/2006 | Lentz |
| 2006/0142838 A1 | 6/2006 | Molaei et al. |
| 2006/0149350 A1 | 7/2006 | Patel et al. |
| 2006/0155358 A1 | 7/2006 | LaDuca et al. |
| 2006/0155363 A1 | 7/2006 | LaDuca et al. |
| 2006/0155366 A1 | 7/2006 | LaDuca et al. |
| 2006/0161244 A1 | 7/2006 | Sequin |
| 2006/0173525 A1 | 8/2006 | Behl et al. |
| 2006/0178726 A1 | 8/2006 | Myles |
| 2006/0184226 A1 | 8/2006 | Austin |
| 2006/0184237 A1 | 8/2006 | Weber et al. |
| 2006/0200223 A1 | 9/2006 | Andreas et al. |
| 2006/0212107 A1 | 9/2006 | Case et al. |
| 2006/0217794 A1 | 9/2006 | Ruiz et al. |
| 2006/0224232 A1 | 10/2006 | Chobotov |
| 2006/0229669 A1 | 10/2006 | Mirizzi et al. |
| 2006/0229699 A1 | 10/2006 | Tehrani et al. |
| 2006/0229707 A1 | 10/2006 | Khoury |
| 2006/0233990 A1 | 10/2006 | Humphrey et al. |
| 2006/0233991 A1 | 10/2006 | Humphrey et al. |
| 2006/0247760 A1 | 11/2006 | Ganesan et al. |
| 2006/0247761 A1 | 11/2006 | Greenberg et al. |
| 2006/0259063 A1 | 11/2006 | Bates et al. |
| 2006/0264801 A1 | 11/2006 | Bolling et al. |
| 2006/0265045 A1 | 11/2006 | Shiu et al. |
| 2006/0271163 A1 | 11/2006 | Shokoohi |
| 2006/0271164 A1 | 11/2006 | Shaolian et al. |
| 2006/0276872 A1 | 12/2006 | Arbefeuille et al. |
| 2007/0005001 A1 | 1/2007 | Rowe et al. |
| 2007/0010867 A1 | 1/2007 | Carter et al. |
| 2007/0016280 A1 | 1/2007 | Yacoby et al. |
| 2007/0021828 A1 | 1/2007 | Krolik et al. |
| 2007/0027522 A1 | 2/2007 | Chang et al. |
| 2007/0027526 A1 | 2/2007 | Demetriades et al. |
| 2007/0043421 A1 | 2/2007 | Mangiardi et al. |
| 2007/0043425 A1 | 2/2007 | Hartley et al. |
| 2007/0043430 A1 | 2/2007 | Stinson |
| 2007/0049906 A1 | 3/2007 | Magnusson |
| 2007/0050006 A1 | 3/2007 | Lavelle |
| 2007/0050016 A1 | 3/2007 | Gregorich et al. |
| 2007/0055339 A1 | 3/2007 | George et al. |
| 2007/0055350 A1 | 3/2007 | Erickson |
| 2007/0055360 A1 | 3/2007 | Hanson et al. |
| 2007/0055362 A1 | 3/2007 | Brown |
| 2007/0060914 A1 | 3/2007 | Magnusson |
| 2007/0067019 A1 | 3/2007 | Miller et al. |

(56) References Cited

U.S. PATENT DOCUMENTS

| | | |
|---|---|---|
| 2007/0067023 A1 | 3/2007 | Kveen et al. |
| 2007/0073376 A1 | 3/2007 | Krolik et al. |
| 2007/0073388 A1 | 3/2007 | Krolik et al. |
| 2007/0088424 A1 | 4/2007 | Greenberg et al. |
| 2007/0112420 A1 | 5/2007 | LaDuca |
| 2007/0118207 A1 | 5/2007 | Amplatz et al. |
| 2007/0118208 A1 | 5/2007 | Kerr |
| 2007/0123805 A1 | 5/2007 | Shireman et al. |
| 2007/0142896 A1 | 6/2007 | Anderson et al. |
| 2007/0150051 A1 | 6/2007 | Arnault De La Menardiere et al. |
| 2007/0156224 A1 | 7/2007 | Cloanta et al. |
| 2007/0167926 A1 | 7/2007 | Blott et al. |
| 2007/0167955 A1 | 7/2007 | Arnault De La Menardiere et al. |
| 2007/0168014 A1 | 7/2007 | Jimenez |
| 2007/0168019 A1 | 7/2007 | Amplatz et al. |
| 2007/0173921 A1 | 7/2007 | Wholey et al. |
| 2007/0179592 A1 | 8/2007 | Schaeffer |
| 2007/0191927 A1 | 8/2007 | Bowe et al. |
| 2007/0198076 A1 | 8/2007 | Hebert et al. |
| 2007/0203571 A1 | 8/2007 | Kaplan et al. |
| 2007/0213804 A1 | 9/2007 | Schaeffer et al. |
| 2007/0213805 A1 | 9/2007 | Schaeffer et al. |
| 2007/0219620 A1 | 9/2007 | Eells et al. |
| 2007/0219621 A1 | 9/2007 | Hartley et al. |
| 2007/0225659 A1 | 9/2007 | Melsheimer |
| 2007/0225796 A1 | 9/2007 | Yadin et al. |
| 2007/0225797 A1 | 9/2007 | Krivoruhko |
| 2007/0225798 A1 | 9/2007 | Gregorich |
| 2007/0233220 A1 | 10/2007 | Greenan |
| 2007/0239254 A1 | 10/2007 | Chia et al. |
| 2007/0244540 A1 | 10/2007 | Pryor |
| 2007/0244542 A1 | 10/2007 | Greenan et al. |
| 2007/0244547 A1 | 10/2007 | Greenan |
| 2007/0248640 A1 | 10/2007 | Karabey et al. |
| 2007/0250084 A1 | 10/2007 | Sharkway et al. |
| 2007/0260301 A1 | 11/2007 | Chuter et al. |
| 2007/0260302 A1 | 11/2007 | Igaki |
| 2007/0260304 A1 | 11/2007 | Gregorich et al. |
| 2007/0149166 A1 | 12/2007 | Schaeffer et al. |
| 2007/0282166 A1 | 12/2007 | Ayala et al. |
| 2007/0282302 A1 | 12/2007 | Wachsman et al. |
| 2007/0293940 A1 | 12/2007 | Schaeffer et al. |
| 2007/0299494 A1 | 12/2007 | Zukowski |
| 2007/0299495 A1 | 12/2007 | Zukowski et al. |
| 2007/0299497 A1 | 12/2007 | Shaollan et al. |
| 2007/0299499 A1 | 12/2007 | Hartley |
| 2007/0299501 A1 | 12/2007 | Hebert et al. |
| 2008/0009932 A1 | 1/2008 | Ta et al. |
| 2008/0009933 A1 | 1/2008 | Ta et al. |
| 2008/0009937 A1 | 1/2008 | Kipperman |
| 2008/0015681 A1 | 1/2008 | Wilson |
| 2008/0027528 A1 | 1/2008 | Jagger et al. |
| 2008/0033354 A1 | 2/2008 | Hartley et al. |
| 2008/0033525 A1 | 2/2008 | Shaked et al. |
| 2008/0046005 A1 | 2/2008 | Lenker et al. |
| 2008/0046066 A1 | 2/2008 | Jenson et al. |
| 2008/0058918 A1 | 3/2008 | Watson |
| 2008/0065197 A1 | 3/2008 | Meyer et al. |
| 2008/0071343 A1 | 3/2008 | Mayberry et al. |
| 2008/0082052 A1 | 4/2008 | Schnell et al. |
| 2008/0082154 A1 | 4/2008 | Tseng et al. |
| 2008/0086191 A1 | 4/2008 | Valencia |
| 2008/0109065 A1 | 5/2008 | Bowe |
| 2008/0114444 A1 | 5/2008 | Yu |
| 2008/0114446 A1 | 5/2008 | Hartley |
| 2008/0125849 A1 | 5/2008 | Burpee et al. |
| 2008/0133000 A1 | 6/2008 | Molony |
| 2008/0140003 A1 | 6/2008 | Bel et al. |
| 2008/0167704 A1 | 7/2008 | Wright et al. |
| 2008/0167705 A1 | 7/2008 | Agnew |
| 2008/0172042 A1 | 7/2008 | House |
| 2008/0172119 A1 | 7/2008 | Yamasaki et al. |
| 2008/0172122 A1 | 7/2008 | Mayberry et al. |
| 2008/0188921 A1 | 8/2008 | Yamasaki et al. |
| 2008/0208319 A1 | 8/2008 | Rabkin et al. |
| 2008/0255652 A1 | 10/2008 | Thomas et al. |
| 2008/0262595 A1 | 10/2008 | Chu et al. |
| 2008/0262596 A1 | 10/2008 | Xiao |
| 2008/0269866 A1 | 10/2008 | Hamer et al. |
| 2008/0269867 A1 | 10/2008 | Johnson |
| 2008/0275542 A1 | 11/2008 | LaDuca |
| 2008/0281399 A1 | 11/2008 | Hartley |
| 2008/0294230 A1 | 11/2008 | Parker |
| 2008/0294237 A1 | 11/2008 | Chu |
| 2009/0005847 A1 | 1/2009 | Adams |
| 2009/0012602 A1 | 1/2009 | Quadri |
| 2009/0030495 A1 | 1/2009 | Koch |
| 2009/0043373 A1 | 2/2009 | Arnault de la Menardiere et al. |
| 2009/0043377 A1 | 2/2009 | Greenberg et al. |
| 2009/0048663 A1 | 2/2009 | Greenberg |
| 2009/0069880 A1 | 3/2009 | Vonderwalde et al. |
| 2009/0088791 A1 | 4/2009 | Drasler et al. |
| 2009/0099638 A1 | 4/2009 | Grewe |
| 2009/0099649 A1 | 4/2009 | Chobotov et al. |
| 2009/0105798 A1 | 4/2009 | Koch |
| 2009/0105806 A1 | 4/2009 | Benjamin et al. |
| 2009/0109065 A1 | 4/2009 | Pinheiro |
| 2009/0132024 A1 | 5/2009 | Berkhoff |
| 2009/0138065 A1 | 5/2009 | Zhang et al. |
| 2009/0155337 A1 | 6/2009 | Schreck et al. |
| 2009/0164001 A1 | 6/2009 | Biggs et al. |
| 2009/0192586 A1 | 7/2009 | Tabor et al. |
| 2009/0240316 A1 | 9/2009 | Bruszewski |
| 2009/0254165 A1 | 10/2009 | Tabor et al. |
| 2009/0254170 A1 | 10/2009 | Hartley et al. |
| 2009/0259290 A1 | 10/2009 | Bruszewski et al. |
| 2009/0259296 A1 | 10/2009 | McIff et al. |
| 2009/0264985 A1 | 10/2009 | Bruszewski |
| 2009/0276028 A1 | 11/2009 | Bailey et al. |
| 2009/0287145 A1 | 11/2009 | Cragg et al. |
| 2010/0016943 A1 | 1/2010 | Chobotov |
| 2010/0160863 A1 | 1/2010 | Heuser |
| 2010/0030318 A1 | 2/2010 | Berra |
| 2010/0057185 A1 | 3/2010 | Melsheimer et al. |
| 2010/0063575 A1 | 3/2010 | Shalev et al. |
| 2010/0063576 A1 | 3/2010 | Schaeffer et al. |
| 2010/0094390 A1 | 4/2010 | Goldmann et al. |
| 2010/0094393 A1 | 4/2010 | Cordeiro et al. |
| 2010/0114290 A1 | 5/2010 | Rasmussen et al. |
| 2010/0168619 A1 | 7/2010 | Elsesser |
| 2010/0168674 A1 | 7/2010 | Shaw et al. |
| 2010/0168834 A1 | 7/2010 | Ryan et al. |
| 2010/0179635 A1 | 7/2010 | Dittman |
| 2010/0179636 A1 | 7/2010 | Mayberry et al. |
| 2010/0179638 A1 | 7/2010 | Shaolian et al. |
| 2010/0261662 A1 | 10/2010 | Schreck et al. |
| 2010/0262157 A1 | 10/2010 | Silver et al. |
| 2010/0268234 A1 | 10/2010 | Aho et al. |
| 2010/0274270 A1 | 10/2010 | Patel et al. |
| 2010/0274340 A1 | 10/2010 | Hartley et al. |
| 2010/0318181 A1 | 12/2010 | Shaolian et al. |
| 2011/0009945 A1 | 1/2011 | Parker et al. |
| 2011/0015728 A1 | 1/2011 | Jimenez et al. |
| 2011/0046712 A1 | 2/2011 | Melsheimer et al. |
| 2011/0054586 A1 | 3/2011 | Mayberry et al. |
| 2011/0054587 A1 | 3/2011 | Mayberry et al. |
| 2011/0121023 A1 | 5/2011 | Milan |
| 2011/0178588 A1 | 7/2011 | Haselby |
| 2011/0218607 A1 | 9/2011 | Arbefeuille et al. |
| 2011/0218617 A1 | 9/2011 | Nguyen |
| 2011/0224742 A1 | 9/2011 | Weisel et al. |
| 2011/0224772 A1 | 9/2011 | Mayberry et al. |
| 2011/0224782 A1 | 9/2011 | Douglas et al. |
| 2011/0251664 A1 | 10/2011 | Acosta De Acevedo |
| 2011/0257718 A1 | 10/2011 | Argentine |
| 2011/0270371 A1 | 11/2011 | Argentine |
| 2011/0282425 A1 | 11/2011 | Dwork |
| 2011/0288627 A1 | 11/2011 | Hartley et al. |
| 2011/0313503 A1 | 12/2011 | Berra et al. |
| 2012/0029610 A1 | 2/2012 | Shaolian et al. |
| 2012/0109279 A1 | 5/2012 | Mayberry |
| 2012/0221007 A1 | 8/2012 | Batten et al. |
| 2012/0239003 A1 | 9/2012 | Julson et al. |
| 2012/0277847 A1 | 11/2012 | Benjamen |

(56) References Cited

U.S. PATENT DOCUMENTS

| | | | |
|---|---|---|---|
| 2013/0184805 A1 | 7/2013 | Sawada | |
| 2013/0281787 A1 | 10/2013 | Avneri et al. | |
| 2014/0094741 A1* | 4/2014 | Bellisario | A61M 25/0069 604/39 |
| 2014/0194970 A1 | 7/2014 | Chobotov | |
| 2014/0249615 A1 | 9/2014 | Schreck | |
| 2014/0350658 A1 | 11/2014 | Benary et al. | |
| 2014/0358214 A1 | 12/2014 | Schreck et al. | |
| 2015/0173932 A1 | 6/2015 | Mayberry | |
| 2015/0190615 A1* | 7/2015 | Shaltis | A61M 25/0147 604/95.04 |
| 2015/0366688 A1 | 12/2015 | Schreck | |

FOREIGN PATENT DOCUMENTS

| | | |
|---|---|---|
| CA | 2133530 | 4/1995 |
| CA | 2220141 | 11/1996 |
| CA | 2287406 | 12/1997 |
| CN | 105232195 A | 1/2016 |
| DE | 295 21 548 U1 | 2/1995 |
| DE | 295 21 776 U1 | 2/1995 |
| DE | 100 17 147 | 10/2001 |
| EP | 0 282 175 | 9/1988 |
| EP | 0 323 176 | 7/1989 |
| EP | 0 177 330 | 6/1991 |
| EP | 0 458 568 | 11/1991 |
| EP | 0 564 373 | 10/1993 |
| EP | 0 596 145 | 5/1994 |
| EP | 0 621 015 | 10/1994 |
| EP | 0 659 389 | 6/1995 |
| EP | 0 688 545 | 12/1995 |
| EP | 0 689 806 | 1/1996 |
| EP | 0 712 614 | 5/1996 |
| EP | 0 732 088 | 9/1996 |
| EP | 0 732 089 | 9/1996 |
| EP | 0 740 928 | 11/1996 |
| EP | 0 747 020 | 12/1996 |
| EP | 0 775 470 | 5/1997 |
| EP | 0 782 841 | 7/1997 |
| EP | 0 783 873 | 7/1997 |
| EP | 0 783 874 | 7/1997 |
| EP | 0 875 262 | 11/1998 |
| EP | 0 880 938 | 12/1998 |
| EP | 0 880 948 | 12/1998 |
| EP | 0 904 745 | 3/1999 |
| EP | 0 696 447 | 1/2000 |
| EP | 0 974 314 | 1/2000 |
| EP | 1 358 903 | 11/2003 |
| EP | 1 433 438 | 6/2004 |
| EP | 1 470 797 | 10/2004 |
| EP | 1 508 313 | 2/2005 |
| EP | 1 935 374 | 6/2008 |
| EP | 2 429 452 | 3/2012 |
| EP | 2 635 241 | 9/2013 |
| EP | 2 680 915 | 1/2014 |
| ES | 1 038 606 | 7/1998 |
| GB | 1 193 759 | 6/1970 |
| GB | 2206118 B | 9/1990 |
| JP | 04-25755 | 1/1992 |
| JP | H05-81257 | 11/1993 |
| JP | 30-09638 | 4/1994 |
| JP | 07-047134 | 2/1995 |
| JP | 08-052165 | 2/1996 |
| JP | 08-336597 | 12/1996 |
| JP | H951954 A | 2/1997 |
| JP | 09-164209 | 6/1997 |
| JP | 9-511160 | 11/1997 |
| JP | 2000-500047 | 1/2000 |
| JP | 2004-130068 | 4/2004 |
| JP | 2004-136065 A | 5/2004 |
| JP | 2004-532680 A | 10/2004 |
| JP | 2007-236472 | 9/2007 |
| JP | 5629871 | 10/2014 |
| WO | WO 90/14054 | 11/1990 |
| WO | WO 93/13825 | 7/1993 |
| WO | WO 94/24961 | 11/1994 |
| WO | WO 95/21592 | 8/1995 |
| WO | WO 96/14808 | 5/1996 |
| WO | WO 96/34580 | 11/1996 |
| WO | WO 96/38101 | 12/1996 |
| WO | WO 96/39999 | 12/1996 |
| WO | WO 96/41589 | 12/1996 |
| WO | WO 97/10757 | 3/1997 |
| WO | WO 97/10777 | 3/1997 |
| WO | WO 97/14375 | 4/1997 |
| WO | WO 97/17911 | 5/1997 |
| WO | WO 97/18006 | 5/1997 |
| WO | WO 97/19652 | 6/1997 |
| WO | WO 97/26936 | 7/1997 |
| WO | WO 97/033532 | 9/1997 |
| WO | WO 97/045072 | 12/1997 |
| WO | WO 98/02100 | 1/1998 |
| WO | WO 98/11846 | 3/1998 |
| WO | WO 98/20812 | 5/1998 |
| WO | WO 98/27894 | 7/1998 |
| WO | WO 98/27895 | 7/1998 |
| WO | WO 98/53761 | 12/1998 |
| WO | WO 99/13808 | 3/1999 |
| WO | WO 99/029262 | 6/1999 |
| WO | WO 99/44536 | 9/1999 |
| WO | WO 99/47077 | 9/1999 |
| WO | WO 99/53865 | 10/1999 |
| WO | WO 99/58084 | 11/1999 |
| WO | WO 00/33769 | 6/2000 |
| WO | WO 00/53251 | 9/2000 |
| WO | WO 00/67674 | 11/2000 |
| WO | WO 00/78248 | 12/2000 |
| WO | WO 01/03762 | 1/2001 |
| WO | WO 01/24732 | 4/2001 |
| WO | WO 01/26707 | 4/2001 |
| WO | WO 01/067993 | 9/2001 |
| WO | WO 02/36179 | 5/2002 |
| WO | WO 02/39888 | 5/2002 |
| WO | WO 02/060345 | 8/2002 |
| WO | WO 03/068302 | 8/2003 |
| WO | WO 03/094796 | 11/2003 |
| WO | WO 04/047885 | 6/2004 |
| WO | WO 04/089249 | 10/2004 |
| WO | WO 04/105693 | 12/2004 |
| WO | WO 05/037076 | 4/2005 |
| WO | WO 05/037141 | 4/2005 |
| WO | WO 05/067819 | 7/2005 |
| WO | WO 06/028925 | 3/2006 |
| WO | WO 06/036690 | 4/2006 |
| WO | WO 06/047708 | 5/2006 |
| WO | WO 06/071915 | 7/2006 |
| WO | WO 06/117321 | 11/2006 |
| WO | WO 07/027830 | 3/2007 |
| WO | WO 07/092276 | 8/2007 |
| WO | WO-2008/002426 A1 | 1/2008 |
| WO | WO 08/034106 | 3/2008 |
| WO | WO 08/083767 | 7/2008 |
| WO | WO 08/086084 | 7/2008 |
| WO | WO-2008/143243 A1 | 11/2008 |
| WO | WO 09/000546 | 12/2008 |
| WO | WO 09/023221 | 2/2009 |
| WO | WO 09/105699 | 8/2009 |
| WO | WO 10/127040 | 11/2010 |
| WO | WO 11/049808 | 4/2011 |
| WO | WO 12/061526 | 5/2012 |
| WO | WO 12/118901 | 9/2012 |
| WO | WO-2014/159116 A1 | 10/2014 |

OTHER PUBLICATIONS

US 6,413,270 B1, 07/2002, Thornton et al. (withdrawn)
Chinese Office Action dated Jun. 3, 2019, for application No. 201680001552.1.
Chinese Office Action dated Sep. 28, 2018, from application No. 201680001552.1.
Extended European Search Report dated Jan. 9, 2018, from application No. 16790254.3.

(56) References Cited

OTHER PUBLICATIONS

Final Office Action dated Apr. 15, 2020, from U.S. Appl. No. 15/317,905.
Japanese Office Action dated Jun. 1, 2021, from application No. 2016-565006.
Japanese Office Action dated Jun. 30, 2020, from application No. 2016-565006.
Non-Final Office Action dated Oct. 6, 2021, from U.S. Appl. No. 15/317,905.
Non-Final Office Action dated Sep. 23, 2019, from U.S. Appl. No. 15/317,905.
Notice of Allowance dated May 12, 2021, from U.S. Appl. No. 15/317,905.
European Office Action dated Mar. 17, 2023, for application No. 16790254.3.
U.S. Appl. No. 09/714,854, filed Nov. 15, 2000, Shaollan et al.
Definition of mounted, Dictionary.com, retrieved Nov. 18, 2010 from http://dictionary.com/browse/mounted.
Instructions for use of the Gore Excluder® AAA Prosthesis, pp. 1-17, Apr. 2009.
International Search Report and Written Opinion, re PCT Application No. PCT/US 16/40197, mailed Oct. 24, 2016.
Minion et al., "Technique of slow deployment of Gore Excluder endograft improves accuracy of placement", J Vasc Surg 43:852-4, 2006.
Chinese Office Action dated Jun. 24, 2022, from application No. 202010427190.0, 7 pages.
Japanese Office Action dated Dec. 6, 2023, for application No. 2022-189928.

\* cited by examiner

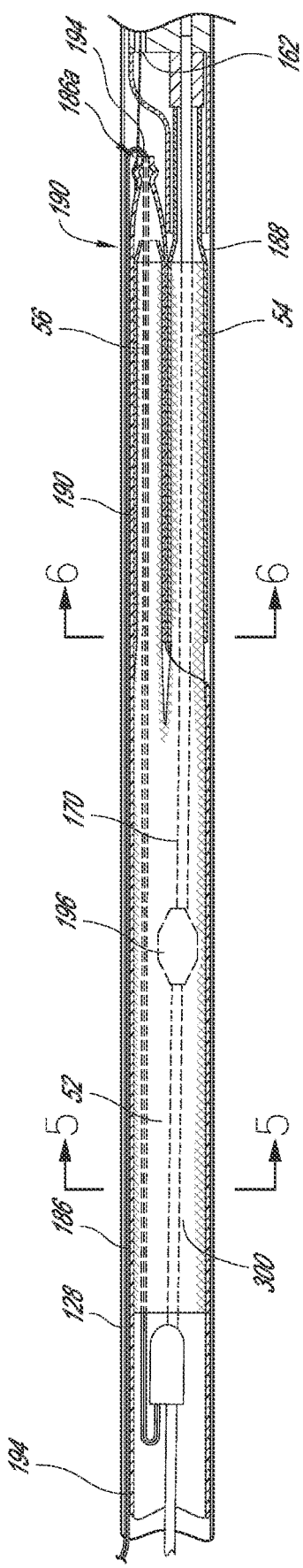
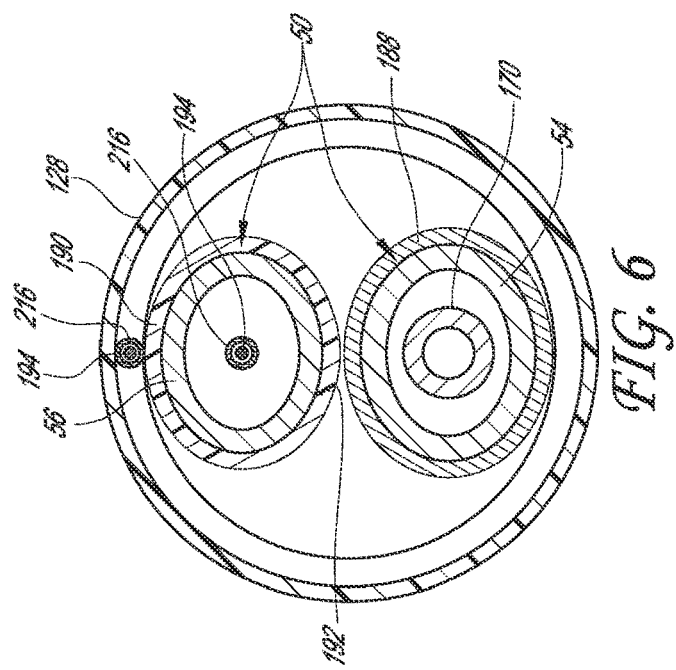
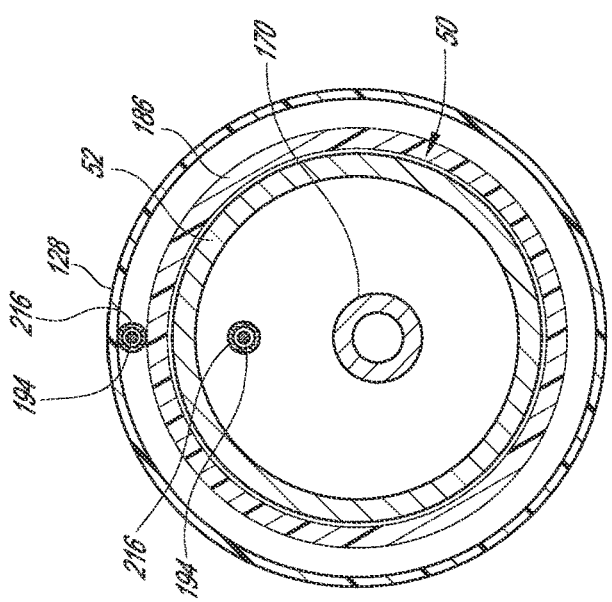
FIG. 4
FIG. 5
FIG. 6

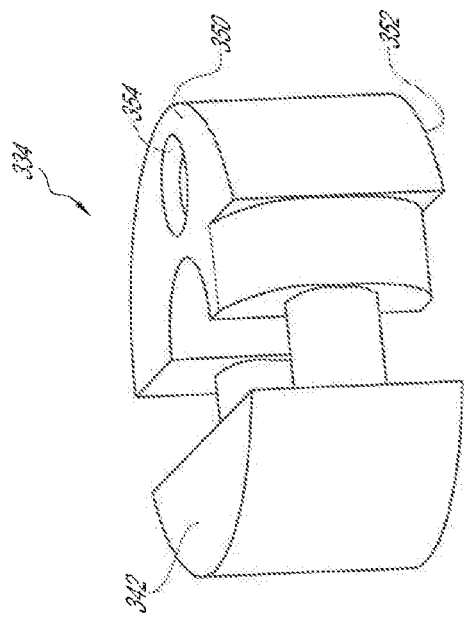
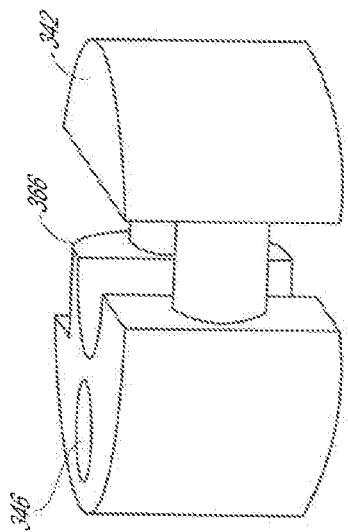
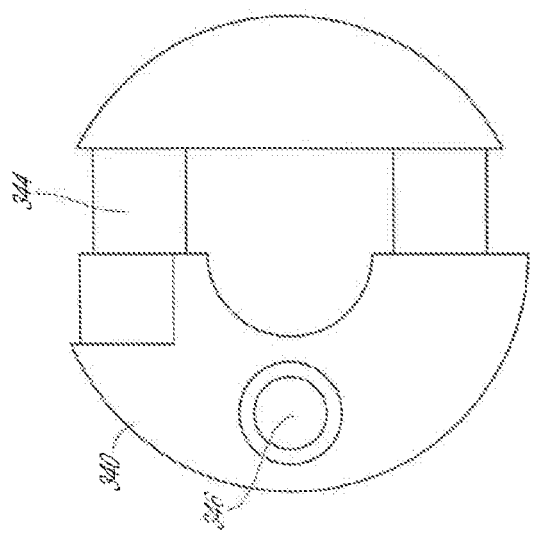
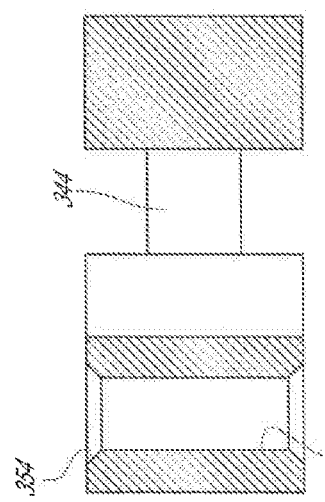
FIG. 14B
FIG. 14D
FIG. 14A
FIG. 14C

LOCKING ASSEMBLY FOR COUPLING GUIDEWIRE TO DELIVERY SYSTEM

INCORPORATION BY REFERENCE TO ANY PRIORITY APPLICATIONS

This application is a continuation application of U.S. patent application Ser. No. 15/317,905, entitled as "LOCKING ASSEMBLY FOR COUPLING GUIDEWIRE TO DELIVERY SYSTEM", filed Dec. 9, 2016, which is a national phase of Application No. PCT/US2016/040197, filed Jun. 29, 2016, which claims priority from U.S. Provisional Patent Application No. 62/187,103, filed Jun. 30, 2015, titled LOCKING ASSEMBLY FOR COUPLING GUIDEWIRE TO DELIVERY SYSTEM, each of which is incorporated by reference herein in its entirety.

BACKGROUND

Technical Field

The present disclosure relates to devices and methods for reversibly coupling a guidewire or other elongate structure to a delivery system.

Description of the Related Art

Some surgical procedures require multiple guidewires, for example to facilitate delivery of an implant to a branched vessel or maintain access in a branched vessel. During these procedures, an implant can be delivered via a delivery system through a first branch vessel (e.g., ipsilateral iliac artery) and access can be provided through a second branch vessel (e.g., contralateral iliac artery) using a catheter, guidewire, or otherwise. However, existing techniques for providing access to the branch vessel involve many steps and may increase the size of the delivery system, thus making the procedure more difficult to perform.

SUMMARY

Certain embodiments described herein are directed to systems, methods and apparatuses for treating endovascular aneurysms or other endovascular defects. However, it will be appreciated that the systems, methods and apparatuses may have application to other fields. In some embodiments, the defects being treated may include, but are not limited to, abdominal aortic aneurysms, subclavian aneurysms, and thoracic aortic aneurysms, to name a few.

As mentioned above, certain surgical procedures, such as those for treating aortic aneurysms may involve the use of multiple guidewires to maintain access through multiple vessels. However, managing multiple guidewires can be difficult, for example because a contralateral guidewire may be inadvertently withdrawn when a sheath or other tubular structure is withdrawn over the contralateral guidewire. Existing systems may utilize a hollow guidewire or other tubular structure to couple a contralateral portion of the delivery system to an ipsilateral portion of the delivery system or to facilitate advancement of a contralateral guidewire to the target vessel. However, the hollow guidewire or other elongate structure increases a diameter of the contralateral portion of the delivery system and increases the number of steps involved in providing and/or removing contralateral access. Thus, it may be desirable to provide a delivery system in which the contralateral guidewire is directly secured to the ipsilateral portion of the delivery system to both reduce the diameter of the contralateral portion of the delivery system and/or reduce the number of steps to provide and/or remove contralateral access. Reducing the diameter of the contralateral portion reduces the size of the contralateral access.

Other devices and techniques use gate cannulation to access the contralateral limb of the stent graft above the bifurcation, which can be challenging and time consuming. Certain aspects of the present disclosure allow for easier deployment of the contralateral limb by providing a precannulated stent graft through the contralateral limb. The present disclosure can also allow the use of a larger guidewire (e.g., 0.035 in.). Precannulation of the contralateral limb eliminates gate cannulation, thereby simplifying the graft placement procedure.

Certain aspects of this disclosure are directed toward a locking assembly for releasably coupling a guidewire to a delivery catheter such that the guidewire can be released from the delivery catheter. In certain aspects of the locking assembly herein, a housing has a proximal end, a distal end, and a lateral wall portion. A recess extends at least partially through the lateral wall of the housing. A first lumen extends from the proximal end of the housing to the distal end of the housing along a longitudinal axis. A second lumen extends from the distal end of the housing, the diameter of the second lumen being less than the diameter of the first lumen. The second lumen is configured to receive and retain a guidewire.

Optionally, the locking assembly includes an elastomeric member that is retained in the recess. The elastomeric member can be configured to retain the guidewire when the guidewire extends into the second lumen. At least a portion of the elastomeric member can be substantially flush with an outer surface of the lateral wall of the housing. The elastomeric member can have an opening that at least partially aligns with the second lumen. The opening of the elastomeric member can have a diameter that is smaller than the diameter of the second lumen of the locking assembly to help retain a guidewire extending through the second lumen.

In certain aspects, the locking assembly has a protruding portion extending along at least a portion of the outer periphery of a distal portion of the housing to provide strain relief to the guidewire that extends distally from the second lumen. The second lumen can be positioned between the first lumen and the protruding portion.

Certain aspects of the present disclosure are directed toward a system utilizing the above-described locking assembly. The locking assembly can be fixed to a first elongate member. The system can also include a second elongate member configured to be retained by the second lumen alone or the second lumen in combination with the elastomeric member.

Certain aspects of the disclosure are directed toward a locking assembly that couples a contralateral guidewire to an ipsilateral catheter. The locking assembly has an anchoring portion configured to engage the ipsilateral catheter. The locking assembly has an interlock portion configured to retain a distal portion of the contralateral guidewire when the contralateral guidewire is advanced or retracted unless a vertical force between about 0.01 and about 6.0 lbf (e.g., between about 0.01 and about 0.5 lbf, between about 0.25 and about 0.75 lbf, between about 0.5 lbf and about 1.0 lbf, between about 0.75 lbf and about 1.15 lbf, between about 1.0 lbf and about 2.0 lbf, between about 1.5 lbf and about 2.5 lbf, between about 2.0 lbf and about 3.0 lbf, between about 2.5 lbf and bout 3.5 lbf, between about 3.0 lbf and about 4.0 lbf, between about 3.5 lbf and about 4.5 lbf, between about 4.0 lbf and about 5.0 lbf, between about 4.5 lbf and about 5.5 lbf, or between about 5.0 lbf and about 6.0 lbf, or otherwise) is applied to the contralateral guidewire.

Certain aspects of the present disclosure are directed toward a method of using the locking assembly described above. The method can include advancing a delivery system in a locked configuration. The delivery system can include a locking assembly fixed to the ipsilateral catheter. The locking assembly can include an interlock portion configured to retain the guidewire when the delivery system is in the locked configuration. A distal end of the guidewire can be introduced into the interlock portion from a distal side of the locking assembly such that the guidewire has a bend when the delivery system is in the locked configuration. The bend can be positioned between a proximal portion of the guidewire and the distal portion of the guidewire. The method can also include releasing the delivery system from the locked configuration to the unlocked configuration by advancing a release catheter along the guidewire.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

FIG. 4 is an enlargement of the portion delineated by curve 4-4 in FIG. 3.

FIG. 5 is a cross-sectional view of the embodiment of the deployment catheter shown in FIG. 3 taken along line 5-5 of FIG. 4.

FIG. 6 is a cross-sectional view of the embodiment of the deployment catheter shown in FIG. 3 taken along line 6-6 of FIG. 4.

FIG. 14A is a top view of an embodiment of the elastomeric member shown in FIG. 14.

FIG. 14B is a rear view of an embodiment of the elastomeric member shown in FIG. 14.

FIG. 14C is a front cross-sectional view of an embodiment of the elastomeric member shown in FIG. 14.

FIG. 14D is a front view of an embodiment of the elastomeric member shown in FIG. 14.

DETAILED DESCRIPTION

Figure 1A:
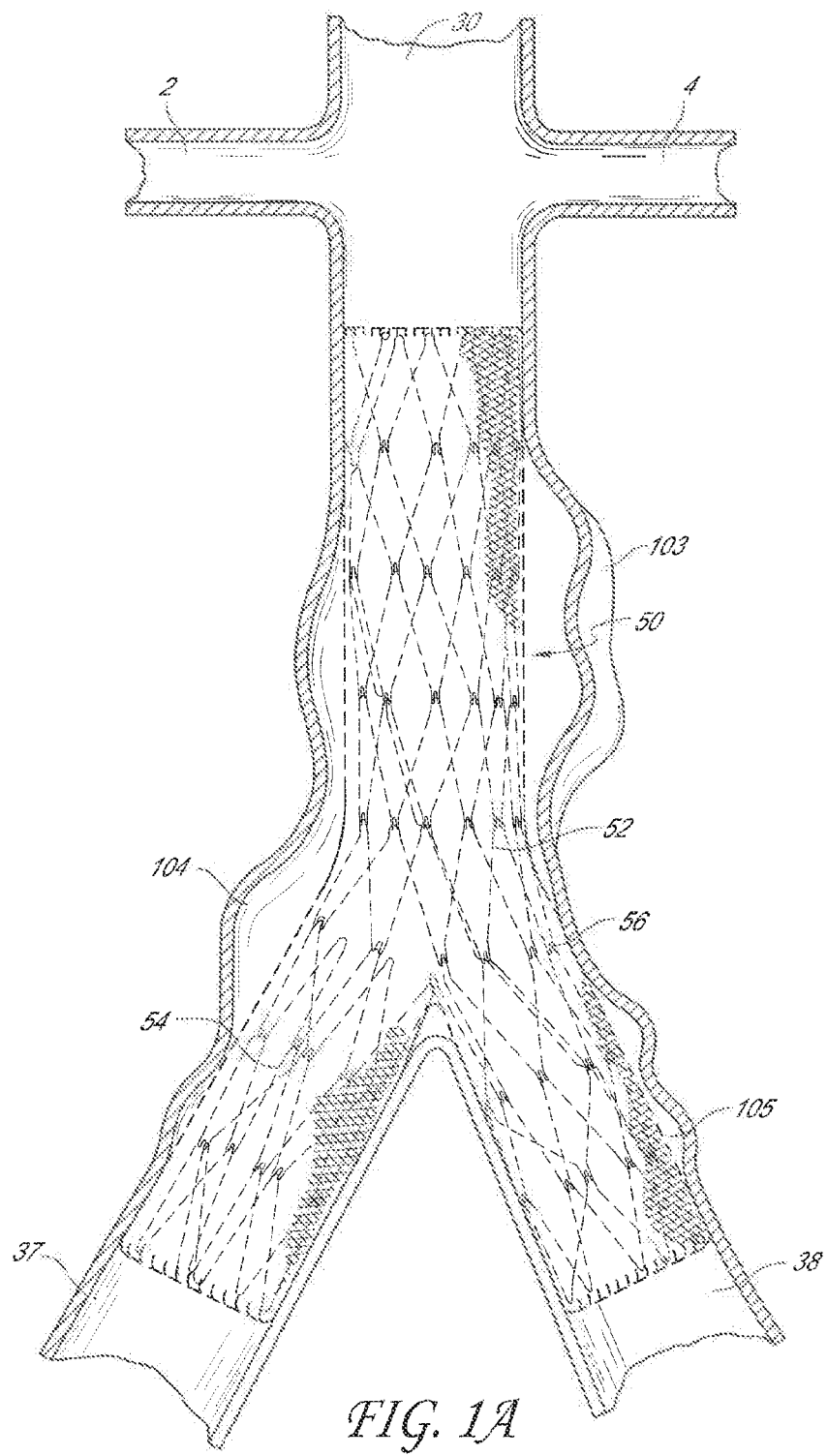
FIG. 1A is a schematic representation of a bifurcated vascular prosthesis for use with the present disclosure, positioned at the bifurcation between the abdominal aorta and the right and left common iliac arteries.

The following detailed description is now directed to certain specific embodiments of the disclosure. In this description, reference is made to the figures wherein like parts are designated with like numerals throughout the description and the drawings. Described below are various embodiments of a delivery system for establishing a surgical platform having multiple guidewires. In some aspects, the present disclosure is directed to devices and methods for deploying a vascular graft for treatment of an abdominal aortic aneurysm, including a deployment catheter and a guidewire assembly which may be used to maintain access through an implanted vascular graft for subsequent catheterizations.

An abdominal aortic aneurysm usually arises in the infrarenal portion of the diseased aorta, for example, below the kidneys. The aneurysm often occurs near a site of vessel branching, making a bifurcated stent a well-suited device for treating the abdominal aortic aneurysm. Endoluminal implantation is an increasingly accepted technique for implanting vascular grafts. This procedure may involve femoral cut down access or percutaneously inserting a vascular graft or prosthesis by using a delivery catheter. This process eliminates the need for major surgical intervention, thereby decreasing the risks associated with vascular and arterial surgery. Various embodiments of catheter delivery systems for prosthetic devices are described herein.

Endovascular surgical procedures can use a guidewire to help position a catheter or place prosthesis. Guidewires can provide a surgical platform from which a physician can conduct a minimally-invasive medical procedure. In some instances, a physician may use multiple guidewires in a medical procedure. When multiple guidewires are used, a first guidewire may have at least one of its ends in a location that is different from at least one of the ends of a second guidewire. When multiple guidewires are used, at least a portion of a first guidewire may be located in proximity to at least a portion of a second guidewire. In some instances, one end of a first guidewire may be located next to a portion of a second guidewire while the other end of the first guidewire is at a location different from the location of the end of the second guidewire. A first guidewire may access the patient at one location and be joined within the patient to a second guidewire that accesses the patient from a different location. Guidewires that access the patient's body from different locations can be used to deploy a bifurcated stent, to seat a heart valve, or to perform an endovascular surgical procedure.

Certain current delivery systems for a bifurcated stent graft system or a graft having at least one branch portion may use two separate sheaths to deploy the distal segment of the graft before the proximal segment. The outer sheath is first retracted to deploy a portion of the mid-body and the contralateral limb. Then, the front sheath is advanced distally to deploy the distal end of the graft, See e.g., U.S. Pat. No. 6,660,030. Other delivery systems, for example as disclosed in U.S. patent application Ser. No. 11/522,292, titled "A MULTI-SEGMENTED GRAFT DEPLOYMENT SYSTEM" and filed on Sep. 15, 2006 (the entirety of which is hereby incorporated by reference as if fully set forth herein) may use a plurality of axially spaced releasable restraint members temporarily connected by a pull wire to allow the distal main branch portion to be deployed before a proximal graft portion. Typically, these delivery systems are delivered to the aneurysm location over a guidewire. The guidewire may be further used to release a branch graft portion of the prosthesis, for example, by operably connecting a branch graft restraint mechanism to the guidewire and proximally withdrawing the guidewire from the vasculature.

Once the bifurcation graft has been deployed and implanted, a variety of procedures may desirably be accomplished. For example, it may be advantageous to implant a cuff (e.g., on the proximal end of the main branch portion) to secure the graft and thereby prevent movement or slippage of the main branch portion. Alternatively, it may be necessary to dilate the stenosis or touch up or re-establish the expansion of the graft. These procedures require advancing another catheter to the graft location along a guidewire. However, the positioning of a guidewire through the graft after the graft has been deployed is difficult since the tip of the guidewire may snag on the wire support cage of the graft. Thus, it may be advantageous to provide a guidewire assembly configured to remain placed through a graft once the graft has been deployed and to allow access through the expanded graft for subsequent catheterizations. Additionally, it may be advantageous to improve the configuration of the deployment catheter and/or the graft restraining members so as to improve the methods of deploying and positioning bifurcated and non-bifurcated grafts, as will be described herein.

In certain embodiments, the deployment catheter may be configured to deliver a graft that includes a main or distal graft portion and at least one branch or proximal graft portion. In certain embodiments, the hollow guidewire assembly may be associated with a restraint member for the branch segment, such that the branch segment may be deployed by the guidewire assembly. The guidewire assembly may be further configured such that it may be used to remove the restraint member from the branch segment while permitting placement and maintenance of a guidewire through the expanded branch segment and main body graft for subsequent catheterizations. Other embodiments of a graft deployment system and guidewire assembly will also be described below.

Prosthesis

FIG. 1A is a schematic representation of an example of a bifurcated vascular graft 50 that can be used with any embodiment of the deployment catheter disclosed herein, positioned at the bifurcation between the abdominal aorta 30 and the right and left common iliac arteries 37 and 38. With reference to FIG. 1A, there is illustrated a schematic representation of the abdominal part of the aorta and its principal branches. In particular, the abdominal aorta 30 is characterized by a right renal artery 2 and left renal artery 4. The large terminal branches of the aorta 30 are the right and left common iliac arteries 37 and 38. Additional vessels (e.g., second lumbar, testicular, inferior mesenteric, middle sacral) have been omitted from FIG. 1A for simplification. One embodiment of an expanded bifurcated endoluminal vascular prosthesis is shown spanning aneurysms 103, 104 and 105. The expanded bifurcated endoluminal vascular graft 50 can comprise a main branch portion 52 (also referred to herein as a main branch segment) for traversing the aorta, a first branch portion 54 (also referred to herein as a first branch segment or an ipsilateral branch portion) for spanning an ipsilateral iliac artery 37, and a second branch portion 56 (also referred to herein as a second branch segment or a contralateral branch portion) for spanning a contralateral iliac artery 38.

The terms "first" and "second" may be used interchangeably. In one embodiment, the first branch portion can refer to a downstream or upstream portion of a main branch vessel. For example, in one embodiment, the main branch portion and the first branch portion are configured to lie within at least a portion aortic arch (including, for example, the ascending and/or descending aorta) with main branch portion positioned closer to the heart while the second branch portion can be configured to extend into one of the branch vessels (left subclavian, right subclavian or carotid) that extend from the aortic arch.

Figure 1B:
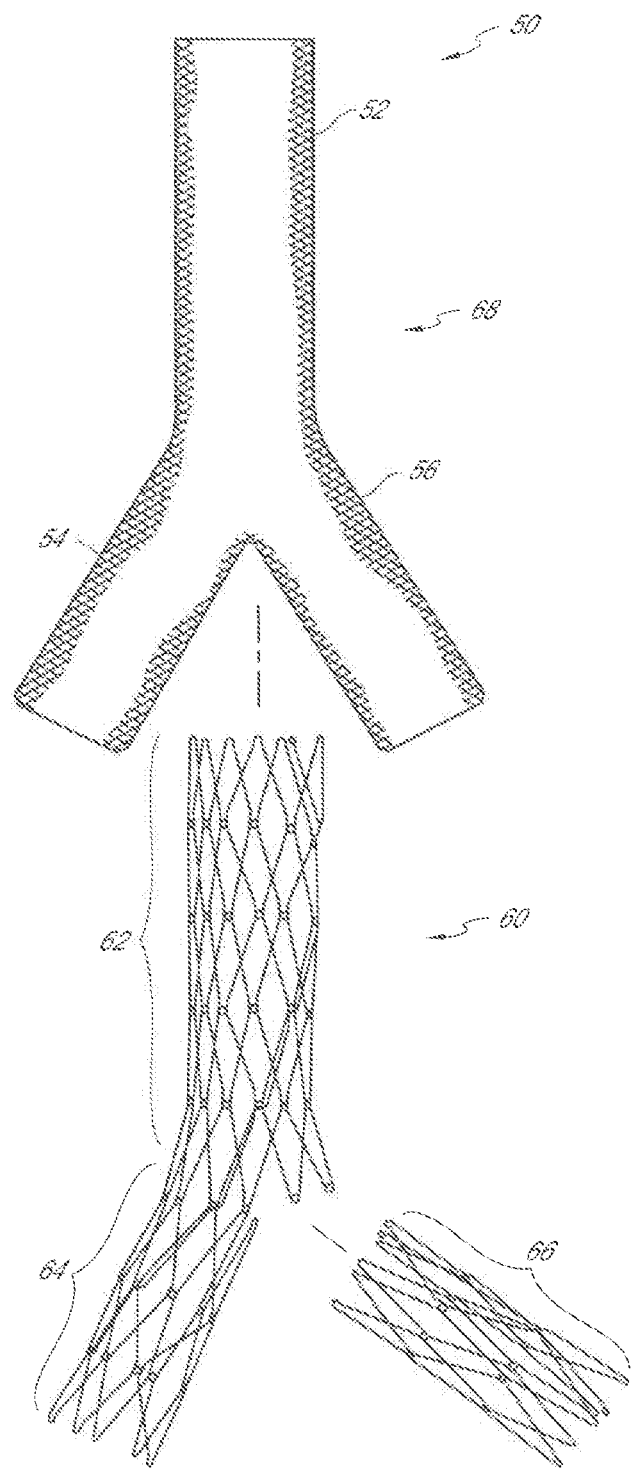
FIG. 1B is an exploded view of a bifurcated graft for use with the present disclosure, showing a self-expanding wire support cage separated from an outer polymeric sleeve.

FIG. 1B is an exploded view of the bifurcated graft 50 of FIG. 1A, which can include a self-expanding wire support cage 60 and an outer polymeric sleeve 68. In FIG. 1B, the wire support 60 is shown separated from an outer polymeric sleeve 68. In the illustrated embodiment, the polymeric sleeve 68 can be situated concentrically outside of the tubular wire support 60. However, other embodiments may include a sleeve positioned instead concentrically inside the wire support or positioned on both the inside and the outside of the wire support. Alternatively, the wire support may be embedded within a polymeric matrix or layer which makes up the sleeve. The sleeve 68 may be attached to the wire support 60 by any of a variety of suitable manners known to those skilled in the art.

The tubular wire support 60 can comprise a main branch portion 62 for traversing the aorta, a first branch portion 64 (also referred to herein as an ipsilateral branch portion) for spanning an ipsilateral iliac and a second branch portion 66 (also referred to herein as a contralateral branch portion) for spanning a contralateral iliac. The main branch portion 62 and first ipsilateral branch portion 64 can be formed from a continuous single length of wire having a proximal end, a distal end and a central lumen extending therebetween. Alternatively, the first ipsilateral branch portion 64 may be formed of one or more lengths of wire pivotably connected to the proximal end of the main branch portion 62. A second, contralateral branch component 66 may be formed of one or more lengths of wire pivotably connected to the proximal end of the main branch portion 62. Each of the iliac branch components has a proximal end, a distal end and a central lumen extending therethrough. Construction of the graft from a three part cage conveniently facilitates the use of different gauge wire in the different components (e.g. 0.014 in. diameter main trunk and 0.012 in. diameter branch components).

In general, each of the components of the bifurcated endoluminal vascular graft 50 may vary considerably in diameter, length, expansion coefficient, and other parameters or characteristics, depending upon the intended application. For implantation within the aorta of a typical adult, the main branch portion 52 will have a length within the range of from approximately 2 in. to approximately 5 in. or more, and, typically within the range of from approximately 3.5 in. to approximately 4 in. The unconstrained outside expanded diameter of the main branch portion 52 will typically be within the range of from approximately 0.75 in. to approximately 1.5 in. The unconstrained expanded outside diameter of the main branch portion 52 can be constant or substantially constant throughout the length, or can be tapered from a relatively larger diameter at the distal end to a relatively smaller diameter at the bifurcation. In general, the diameter of the proximal end of the main branch portion will be on the order of no more than approximately 95% and often no more than approximately 85% of the diameter of the distal end of the main branch portion. The iliac branch portions 54 and 56 will typically be bilaterally symmetrical, having a length within the range of from approximately 0.4 in. to approximately 2.6 in., and a diameter within the range of from approximately 0.04 in. to approximately 0.79 in.

The collapsed prosthesis for use in accordance with the present disclosure has a diameter in the range of approximately 0.08 in, to approximately 0.39 in. The maximum diameter of the collapsed prosthesis can be in the range of approximately 0.12 in. to approximately 0.24 in. (12 to 18 French). Some embodiments of the deployment catheter, including the prosthesis, can have a diameter in the range of from approximately 18 to approximately 20 or approximately 21 French. Other embodiments can have a diameter as low as approximately 19 French, approximately 16 French, approximately 14 French, or smaller. After deployment, the expanded endoluminal vascular prosthesis may radially self-expand to a diameter anywhere in the range of approximately 0.8 in. to approximately 1.6 in.

Although certain prosthesis configurations are disclosed herein, these are only examples of prostheses which are deployable using the embodiments of a deployment catheter and guidewire assembly described herein. In other embodiments, the delivery system described below may be used to deliver and deploy other types of self-expandable bifurcated or multi-segmented prosthesis having a main branch portion and at least one branch graft portion, as will be apparent to those of skill in the art in view of the disclosure herein. For example, in other embodiments, certain features and aspects of the deployment catheter and guidewire assembly can be used to deploy a graft without a branch graft portion, a graft with only one branch portion and/or a graft with more than one graft portions. Further details and additional embodiments of the prosthesis described above can be found in U.S. Pat. Nos. 6,007,296, 6,187,036, and 6,197,049, the entirety of each of which is hereby incorporated by reference herein.

It should also be appreciated that, although the illustrated embodiments are described in the context of a bifurcated graft configured for the abdominal aorta, certain features and aspects of the delivery systems and methods described herein can be used in other portions of the vascular system. For example, it is anticipated that certain features and aspects of the systems and methods described herein can be adapted for use in the thoracic aorta. In some embodiments, the deployment catheter 120 (see FIG. 3) may be configured to treat defects that may include, but are not limited to, abdominal aortic aneurysms, subclavian aneurysms, and thoracic aortic aneurysms, to name a few. It is also anticipated that certain features and aspects of the system described herein may be adapted to deliver a single straight graft segment to the thoracic aorta or other vessels or arteries within the body.

Delivery System

The expandable bifurcation graft 50 can be deployed at a treatment site with any of a variety of deployment catheters, as will be apparent to those of skill in the art. Any of the embodiments of the deployment catheters disclosed herein may comprise any of the materials, features, or other details of any deployment catheters suitable for deploying an expandable bifurcation graft known in the field. Further details and additional embodiments of the deployment catheter can be found in U.S. Pat. Nos. 8,236,040 and 8,523,931, the entirety of each of which is hereby incorporated by reference herein.

The deployment catheters herein disclosed can be used for deploying a self-expanding bifurcation graft known in the field, or in any of the embodiments disclosed in U.S. Pat. Nos. 6,090,128, 6,500,202, 6,660,030, 8,523,931, and U.S. Pat. Pub. 2008/0071343. The entirety of each of the above-referenced patents and published patent applications is hereby incorporated by reference in their entirety as if fully set forth herein.

Figure 2:
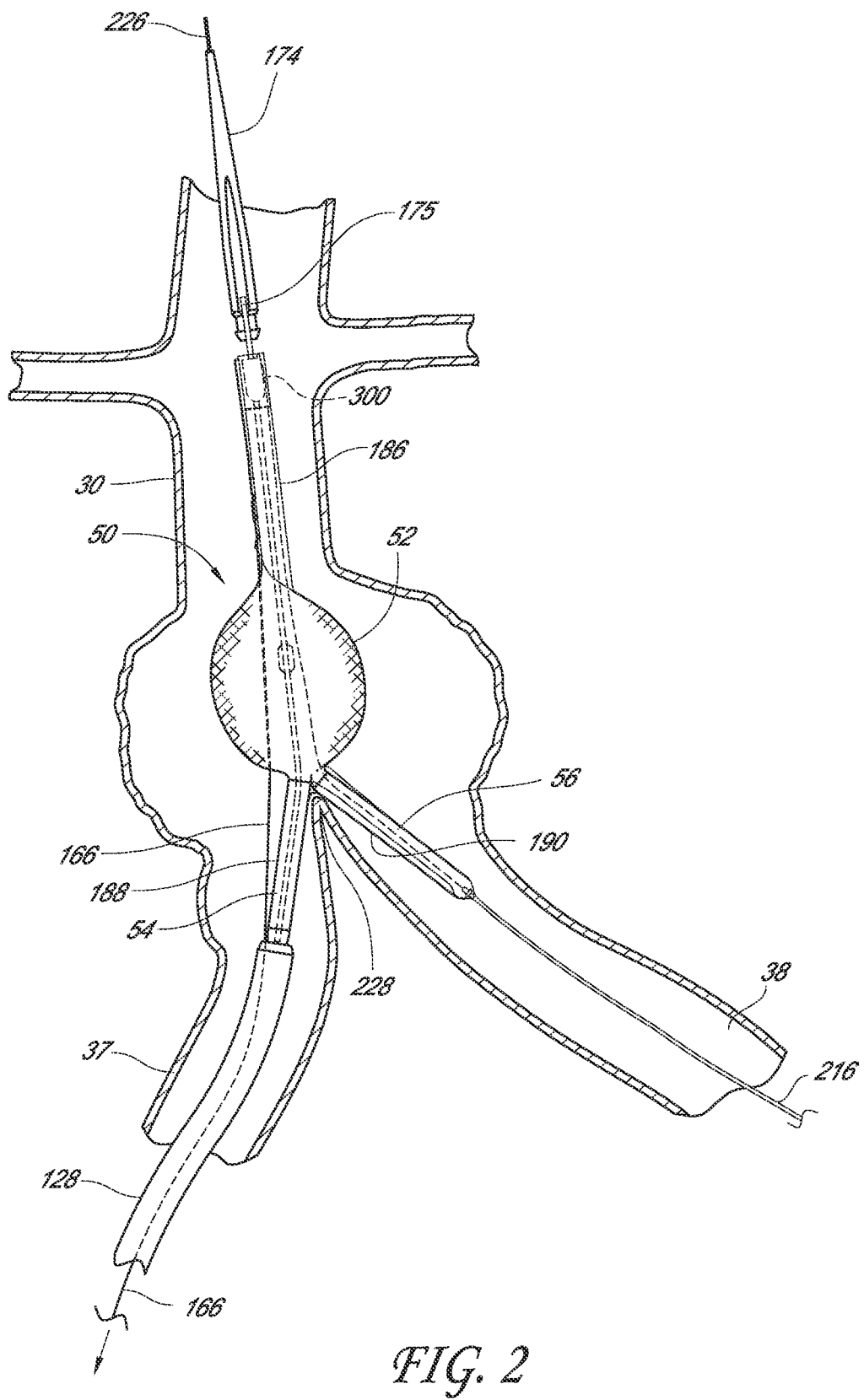
FIG. 2 is a schematic representation of an embodiment of the deployment catheter for delivering a bifurcated prosthesis, with a proximal portion of the main branch portion of the graft at least partially deployed.

With reference to FIG. 2, one method for using an embodiment of a deployment catheter 120 for treating an abdominal aortic aneurysm will be briefly described, without limitation. More detail regarding this deployment method will be described below. FIG. 2 is a schematic representation of an embodiment of a deployment catheter 120 for delivering a bifurcated prosthesis or graft 50, showing a proximal portion of the main branch portion 52 of the graft 50 at least partially deployed within the aorta for illustration purposes. As shown in FIG. 2, the deployment catheter 120 can be introduced into a patient's vasculature through a puncture site in the patient's ipsilateral artery. The deployment catheter 120 is not limited to treatment of an abdominal aortic aneurysm; it can be configured to treat other aneurysms as discussed more fully herein. Additionally, depending on the clinical requirements, the deployment catheter 120 can be introduced into the patient's vasculature through puncture sites other than an ipsilateral artery. For example, without limitation, the deployment catheter 120 can be introduced into the patient's vasculature through a contralateral artery, through a radial artery, or through a subclavian artery.

As illustrated in FIG. 2, the deployment catheter 120 can be advanced over a guidewire 226 to the desired location within the patient's aorta. The graft 50 illustrated in FIG. 2 can include a main branch portion 52 constrained within a main branch sheath or member 186, an ipsilateral branch portion 54 constrained within and ipsilateral branch sheath or member 188, and a contralateral branch portion 56 constrained within a contralateral branch sheath or member 190. Prior to the deployment of the main branch portion 52 of the graft 50 as shown in FIG. 2, the entire graft can be constrained within an outer sheath 128 of the deployment catheter 120. In brief, the graft 50 can be exposed by retracting the outer sheath 128, and the deployment catheter 120 can be manipulated so as to position the contralateral branch portion 56 in the contralateral artery 38.

After positioning the graft 50 in the desired position, illustrated in FIG. 2, the main branch portion 52 of the graft 50 can be deployed by retracting a sheath release 166 (e.g., a cord, suture, wire, or likewise), which can cause the perforated main branch sheath 186 to tear along a side thereof. The remaining portion of the main branch portion 52 can be deployed by further withdrawing the sheath release 166. The main branch sheath 186 can be attached to the sheath release 166, allowing the main branch sheath 186 to be removed through the ipsilateral access site as the sheath release 166 is removed through the ipsilateral access site. In other configurations, the main branch sheath 186 can be separately withdrawn from the contralateral access site or with either the ipsilateral branch sheath 188 or the contralateral branch sheath 190.

In the illustrated embodiment, the contralateral branch portion 56 of the graft 50 can be deployed by withdrawing a contralateral guidewire sheath 216 through a puncture site in the contralateral iliac artery 38, causing the contralateral branch sheath 190 to be withdrawn. Similarly, the ipsilateral branch portion 54 of the graft 50 can be deployed by withdrawing the deployment catheter 120 through a puncture site in the ipsilateral iliac artery 37, causing the ipsilateral branch sheath 188 to be withdrawn either before or after the contralateral branch sheath 190 is withdrawn.

The deployment method described with reference to FIG. 2 is not intended to limit the applicability of the deployment catheter 120. The deployment catheter 120 may be configured to deploy a straight, bifurcated, or any other graft configuration into any portion of an artery or other blood vessel in the body. In some embodiments, the deployment catheter 120 may be used to deploy grafts having anchoring elements that help secure the graft to the vessel wall as well as grafts that do not have anchoring elements. With this brief, non-limiting overview of one method of using the deployment catheter 120 having been described, additional features and configurations of the deployment catheter 120 and additional details of this and other deployment methods will now be described.

Figure 3:
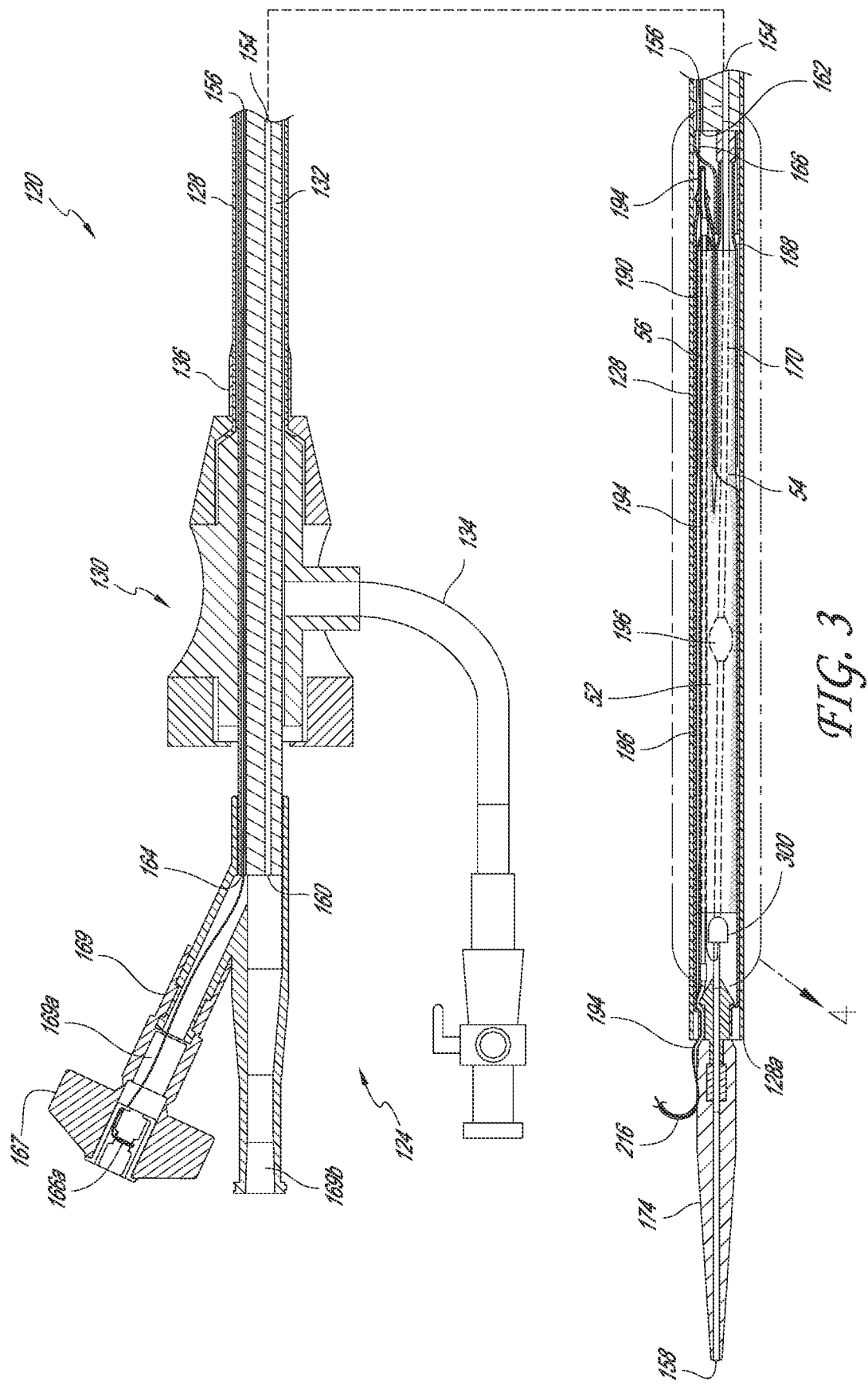
FIG. 3 is a cross-sectional view of an embodiment of a deployment catheter for delivering a bifurcated prosthesis.

FIG. 3 is a cut-away side view of a non-limiting exemplary embodiment of a deployment catheter 120. The inner core 132 of the deployment catheter 120 can include a guidewire lumen 154 and a sheath release lumen 156 extending longitudinally therethrough. The guidewire lumen 154 can be defined by a central tube 170 that can be disposed within inner core 132. The guidewire lumen 154 can be defined by a hole bored along a longitudinal axis of the inner core 132. In the illustrated embodiment, the guidewire lumen 154 can extend throughout the entire length of the tubular inner core 132, having a distal exit port 158 and a proximal access port 160, as will be understood by those of skill in the art. In use, the deployment catheter 120 can be advanced into position in the aorta over a guidewire 226 (shown in FIG. 2) extending through the guidewire lumen 154, as will be understood by those of skill in the art. A sheath release 166 (also may be referred to herein as a cord) can be routed through the sheath release lumen 156. In the illustrated embodiment, the sheath release lumen 156 can extend through the entire length of the tubular inner core 132, having a distal exit port 162 and a proximal access port 164, as will be understood by those of skill in the art.

In the embodiment of the deployment catheter 120, the guidewire lumen 154 can be co-planar with the centerline axis of the inner core 132 and the sheath release lumen 156. However, this arrangement is not required. In some embodiments, the guidewire lumen 154 can be not coplanar with the centerline axis of the inner core 132 and the sheath release lumen 156. Therefore, the inner core 132 may be configured so that the guidewire lumen 154 and the sheath release lumen 156 are formed at any desired position in the cross-section of the inner core 132.

FIG. 4 is an enlargement of the portion delineated by the curve 4 in FIG. 3. FIGS. 5 and 6 are a cross-sectional view of the embodiment of the deployment catheter 120 shown in FIG. 3 taken along line 5-5 and line 6-6, respectively, of FIG. 4. With reference to FIGS. 4-6, a bifurcated endoluminal graft 50 is illustrated in a compressed configuration within the deployment catheter 120, prior to the advancement of the inner core 132 relative to the other sheath 128.

The graft 50 can comprise a distal aortic trunk or main branch portion 52, a proximal ipsilateral branch portion 54, and a proximal contralateral iliac portion 56. In the illustrated embodiment, the aortic main branch portion 52 of the graft 50 can be constrained within a main branch sheath 186. While the embodiment of main branch sheath 186 is shown with reference to compressing a main branch graft portion 52, it is envisioned that the sheath 186 could alternatively be used to compress and deliver other portions of a multi-segmented vascular graft, such as a branch graft portion, the entire multi-segmented graft, or a single-segment, straight vascular graft. Further, in the illustrated embodiment, the ipsilateral branch portion 54 can be constrained with a tubular ipsilateral branch sheath 188 (also referred to herein as the first branch sheath), and the contralateral branch portion 56 (also referred to herein as the second branch sheath) can be constrained within a generally tubular contralateral branch sheath 190. In the illustrated embodiment, the ipsilateral branch sheath 188 and the contralateral branch sheath 190 can be open-ended tubular sheaths.

The ipsilateral branch sheath 188 can constrain substantially the entire length of the ipsilateral branch portion 54 of the bifurcated graft 50. Similarly, in the illustrated embodiment, the contralateral branch sheath 190 can constrain substantially the entire length of the contralateral branch portion 56 of the bifurcated graft 50. However, in some embodiments, the ipsilateral branch sheath 188 and/or the contralateral branch sheath 190 may constrain substantially more or less than the entire length of the ipsilateral branch portion 54 or the contralateral branch portion 56, respectively, of the bifurcated graft 50.

With reference to FIG. 5, the main branch sheath 186 can be sized and configured to circumferentially surround the main branch portion 52 of the bifurcated graft 50. However, in some embodiments, the main branch sheath 186 can be configured to only partially surround the main branch portion 52 of the bifurcated graft 50. The main branch sheath 186 may extend to the distal end of the contralateral branch portion 56 of the graft 50. In some embodiments, the main branch sheath 186 can be configured so as to define a notch 192 along the portion of the length of the main branch sheath 186 that covers the contralateral branch portion 56. In some embodiments, the notch 192 can be a slit along a portion of the length of the main branch sheath 186. In some embodiments, as in the illustrated embodiment, the notch 192 can remove a portion of the main branch sheath 186 along a portion of the length of the main branch sheath 186 that can be less than or equal to approximately half of the perimeter of the main branch sheath 186. In some embodiments, the main branch sheath 186 can be skived to remove a suitable amount of the material comprising the main branch sheath 186 to allow the ipsilateral or contralateral branch portion 54, 56 of the graft 50 to deploy upon retraction of the outer sheath 128. Thus, in some embodiments, the main branch sheath 186 may not constrain the ipsilateral or contralateral branch portion 54, 56 of the bifurcated endoluminal graft 50.

In some embodiments, as illustrated in FIG. 4, a torsion tab 196 can be integrally formed with the central tube 170, or secured thereto such as by thermal bonding, adhesive bonding, and/or any of a variety of other securing techniques known in the art. As is illustrated, the main branch portion 52 of the bifurcated endoluminal graft 50 can be constrained by the main branch sheath 186 around the torsion tab 196. In the illustrated embodiment, the torsion tab 196 can engage with the endoskeleton or, with reference to FIG. 1B, the wire support cage 60 of the bifurcated graft 50 and ensures that the bifurcated graft 50 substantially rotates with the inner core 132 of the deployment catheter 120. In other words, the torsion tab 196 can prevent the central tube 170 from rotating relative to the bifurcated graft 50. This can enhance the ability of the medical practitioner or user to rotate and, hence, maneuver, the graft 50 and the ipsilateral and/or contralateral branch portions 54, 56 within the patient's aorta by rotating the proximal end of the deployment catheter 120, in particular, by rotating the proximal end of the inner core 132 or the "Y" connector 169. As such, the torsion tab 196 can cause the bifurcated endoluminal graft 50 to rotate substantially in unison with the central tube 170.

As described in greater detail below, a locking assembly 300 can couple with the central tube 170. The locking assembly 300 may be integrally formed with the central tube 170, or secured thereto such as by thermal bonding, adhesive bonding, and/or any of a variety of other securing techniques known in the art. The locking assembly 300 can engage a locking portion 194b (shown in FIG. 17A) of a contralateral guidewire 194. The locking portion 194b is also referred to herein as a distal end 194b or as a stiff region. The contralateral guidewire 194 can extend distally from the locking assembly 300 and cannulate the guidewire sheath 216. The contralateral guidewire 194 can then bend proximally back and extend through the main branch portion 52 of the graft 50 and into the contralateral branch portion 56 of the graft 50. The contralateral guidewire 194 and the contralateral guidewire sheath 216 can extend proximally from the contralateral branch portion 56 of the graft 50 and bend back distally, running distally along a gap formed between an inner surface of the outer sheath 128 and an outer surface of the main branch sheath 186. The contralateral guidewire 194 and contralateral guidewire sheath 216 can then exit the delivery catheter 120 through a gap formed between a proximal face of the distal tip 174 and a distal face of the outer sheath 128. The distal tip 174 may include a groove (not shown) that accommodates the contralateral wire 194 as the contralateral wire 194 passes through the junction between the distal tip 174 and the outer sheath 128.

The contralateral branch sheath 190 can be deployed using the contralateral guidewire sheath 216. The ipsilateral branch sheath 188 can be connected to the inner core 132 or the interface member 168 and adapted to be axially proximally withdrawn from the ipsilateral branch portion 182 of the graft 178, thereby permitting the ipsilateral branch portion 182 to expand to its implanted configuration. The main branch sheath 186 can retracted with the contralateral branch sheath 190 or with the ipsilateral branch sheath 188.

Method of Use

With reference to the embodiments of the deployment catheter 120 described above, an exemplary procedure or method of using the deployment catheter 120 to treat a patient's abdominal aortic aneurysm using the embodiments of the bifurcated endoluminal graft 50 disclosed above will now be described. However, the methods and devices of the present disclosure are not to be taken as limited to this particular illustrative example. The present methods and systems can be used in any medical procedure where one desires to reversibly couple catheters, sheaths, guidewires, or similar devices.

In the illustrated embodiment the main branch sheath 186 and the ipsilateral branch sheath 188 are introduced into the patient through the ipsilateral access site and removed from the patient through the ipsilateral access site, while the contralateral branch sheath 190 is introduced through the ipsilateral access site and removed through the contralateral access site.

Figure 7:
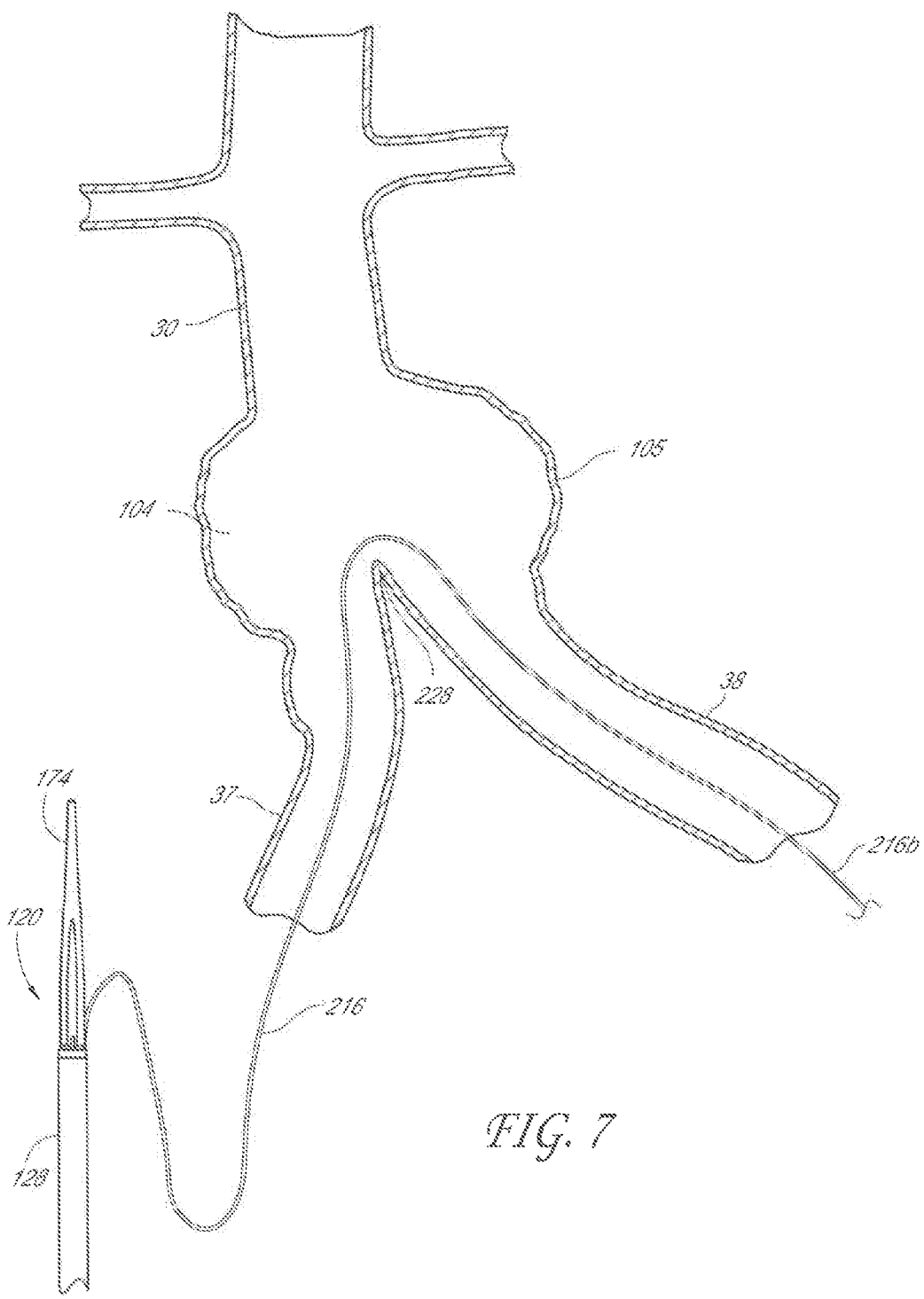
FIG. 7 is a schematic representation of an embodiment of the deployment catheter with the guidewire sheath positioned across the bifurcation.

FIG. 7 is a schematic representation of an embodiment of the deployment catheter 120 with the contralateral guidewire sheath 216 positioned across the bifurcation and within the contralateral iliac artery 38. The hollow contralateral guidewire sheath 216 can be introduced into the ipsilateral iliac artery 37 through an ipsilateral access site in the femoral artery, advanced superiorly towards the aorta 30, and using cross-over techniques known to those skilled in the arts, subsequently advanced inferiorly down the contralateral iliac artery 38 and out a contralateral access site in the contralateral femoral artery. The leading portion 216b of the contralateral guidewire sheath 216 can be externalized by passing the leading portion 216b of the contralateral guidewire sheath 216 through the contralateral access site. As discussed below, the guidewire sheath 216 can be secured to the contralateral branch sheath 190. The contralateral branch portion 56 of the bifurcated graft 50 can be deployed by withdrawing the contralateral guidewire sheath 216 and thereby removing the contralateral branch sheath 190 from the contralateral branch portion 56 of the graft 50. The contralateral branch sheath 190 can be removed through the contralateral access site by pulling on the contralateral guidewire sheath 216.

Figure 8:
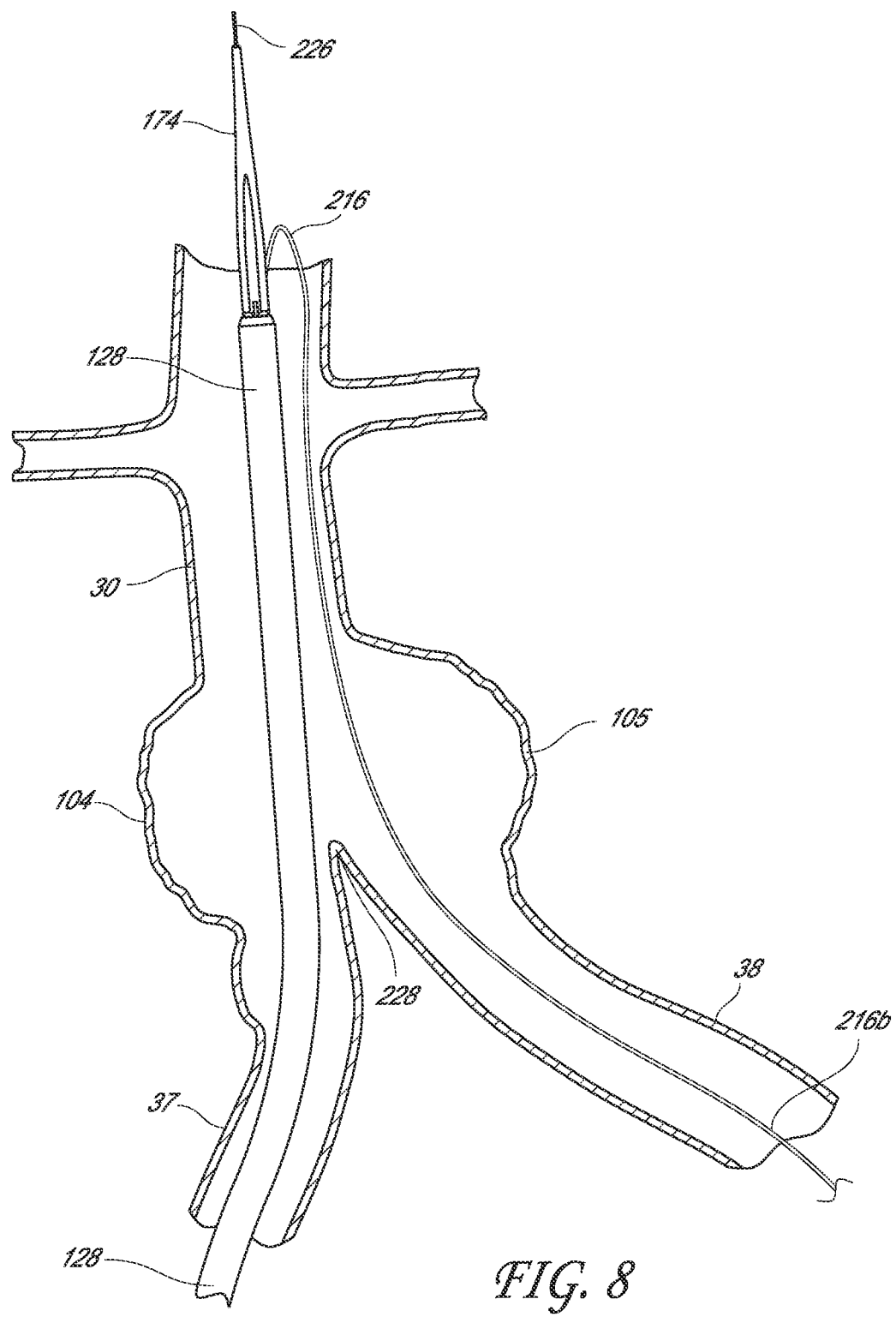
FIG. 8 is a schematic representation, as in FIG. 7, with the deployment catheter positioned in the aorta.

FIG. 8 is a schematic representation, as in FIG. 7, with the deployment catheter 120 positioned in the aorta 30. Referring to FIG. 8, after the contralateral guidewire sheath 216 the has been positioned across the bifurcation 228 in the aorta 30, the deployment catheter 120 can then be advanced over a second guidewire 226 (also referred to as the main guidewire), such as but not limited to a standard 0.035 in. guidewire, from the ipsilateral access site into the aorta 30 using techniques known to those skilled in the arts. Traction can be applied to the hollow contralateral guidewire sheath 216 from the contralateral access site to take up the slack in the contralateral guidewire sheath 216 as the deployment catheter 120 is advanced into the aorta 30.

Figure 9:
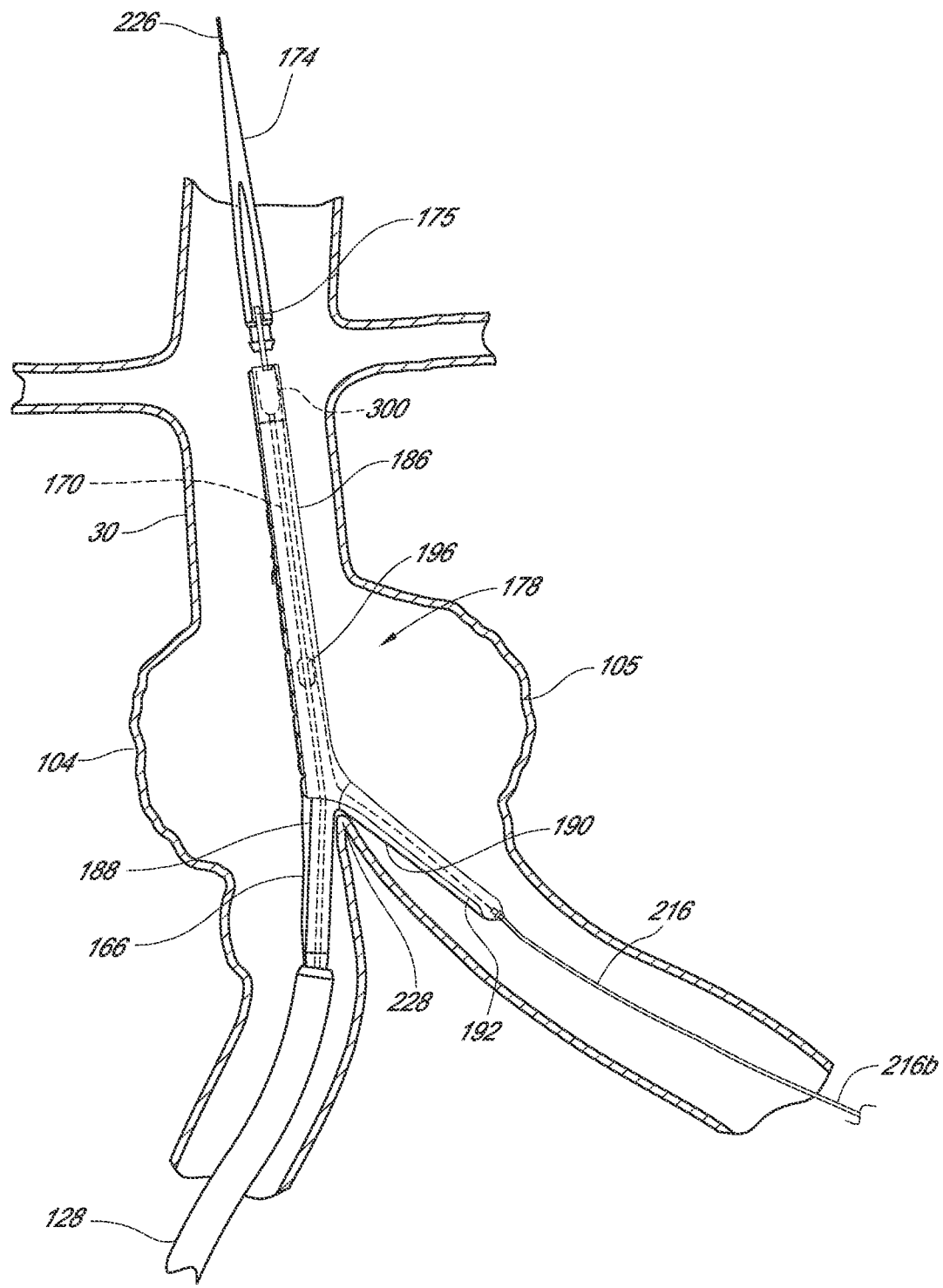
FIG. 9 is a schematic representation, as in FIG. 8, with the compressed iliac branches of the graft positioned partly within the iliac arteries.

FIG. 9 is a schematic representation with the ipsilateral and contralateral branch portions 54, 56 of the graft 50 compressed within the ipsilateral and contralateral branch sheaths 188, 190 (respectively) and positioned substantially fully within the respective ipsilateral and contralateral iliac arteries. As shown in FIG. 9, the bifurcated graft 50 can be configured so as to abut against the bifurcation of the aorta 228 or be positioned in the vicinity of the bifurcation of the aorta 228 by retracting the deployment catheter 120 and, if desired, the contralateral guidewire sheath 216 until the bifurcated graft 50 abuts or is in the vicinity of bifurcation of the aorta 228. The contralateral guidewire 194 can be manipulated so as to seat the graft 50 onto the bifurcation 228 of the aorta 30.

Figure 10:
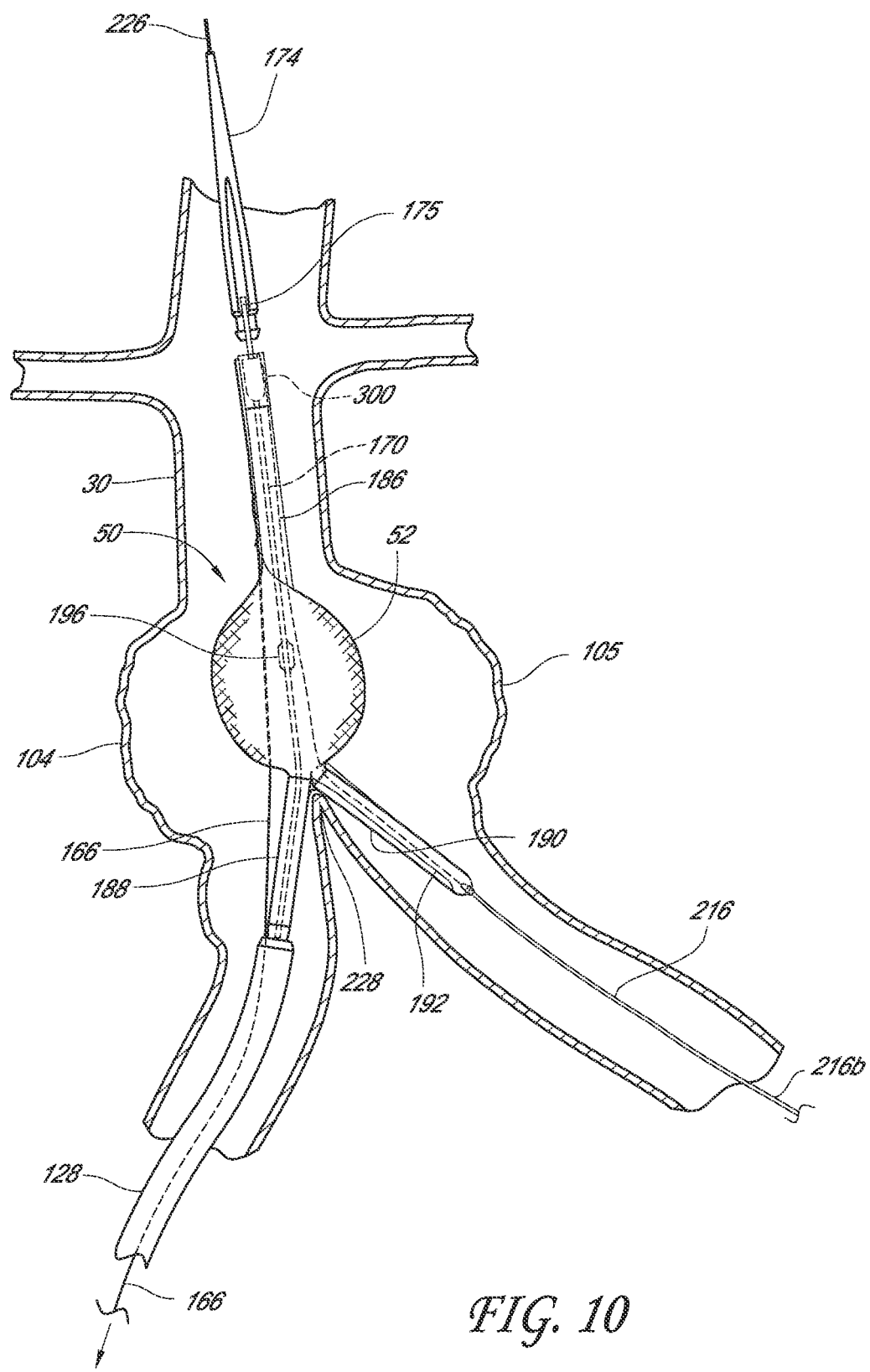
FIG. 10 is a schematic representation, as in FIG. 9, with a proximal portion of the main branch portion of the graft at least partially deployed within the aorta.

FIG. 10 is a schematic representation, as in FIG. 9, with a proximal portion of the main branch portion 52 of the graft 50 or at least partially deployed within the aorta 30. The proximal portion of the main branch portion 52 of the graft 50 can be partially deployed within the aorta 30 as illustrated by proximally retracting the sheath release wire 166, as described above, while holding the inner core 132 of the deployment catheter (see FIG. 3) in a fixed position relative to the aorta 30 so as to prevent exerting undue force on the bifurcation 228 of the aorta 30 or other portions of the anatomy. Deploying the graft 50 in a bottom up sequence, as illustrated herein, may help mitigate the "wind socking" effect that can cause proximal migration of the graft 50. Additionally, deploying the graft 50 and a bottom up sequence may allow for either axially or rotationally repositioning of a partially deployed graft 50 without causing significant or any damage to the arterial wall. In some embodiments, this may partly be due to the fact that the deployed middle portion of the graft 50 may move against the arterial wall more easily than a deployed end portion of the graft 50. The main branch sheath 186 can be attached to the sheath release wire 166 and withdrawn from the patient through the ipsilateral access site.

Figure 11:
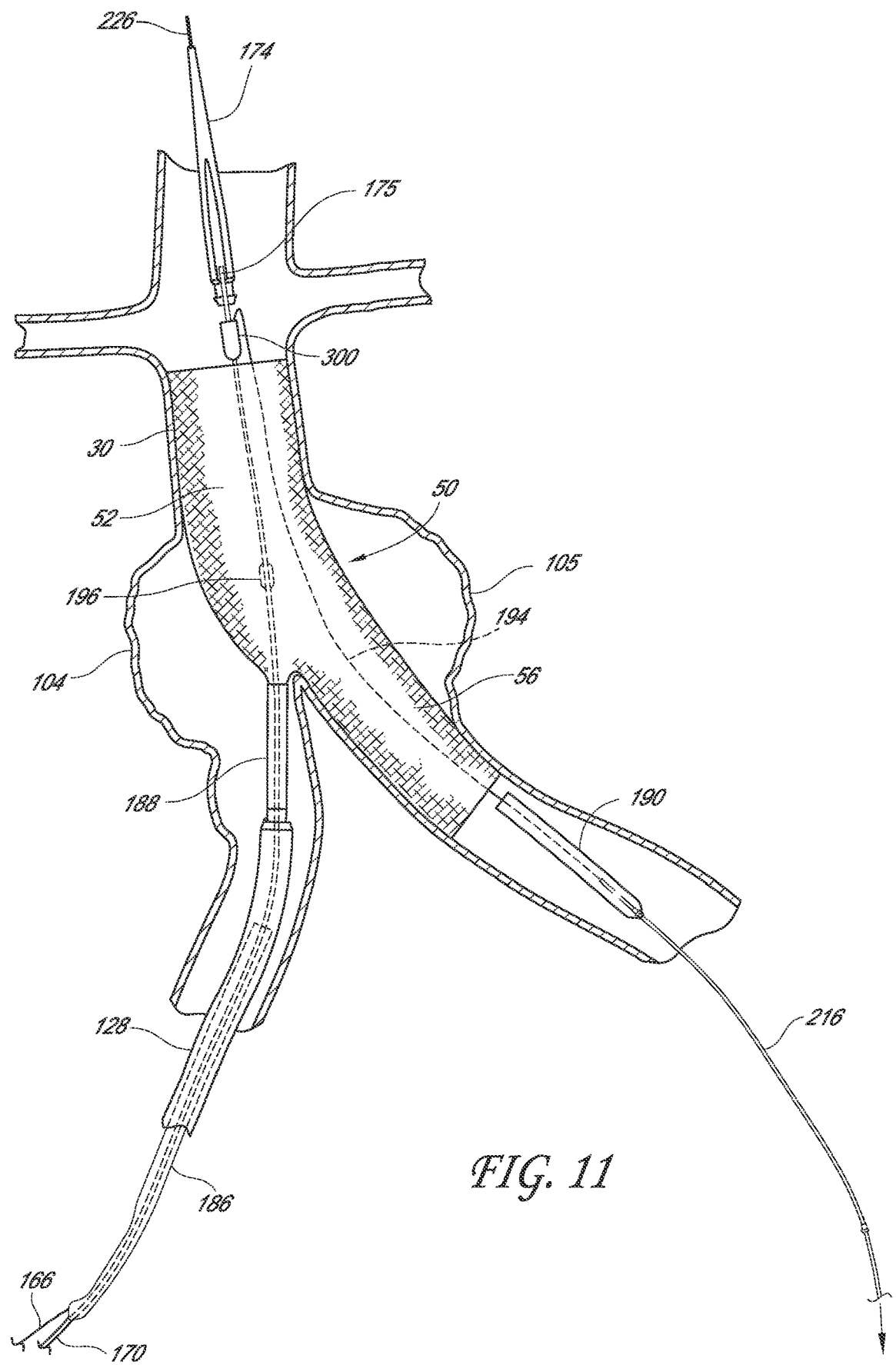
FIG. 11 is a schematic representation, as in FIG. 10, following the further proximal retraction of the guidewire sheath and the contralateral branch sheath through the contralateral iliac artery, causing the deployment of the contralateral branch portion of the graft.

FIG. 11 is a schematic representation, as in FIG. 10, following the further proximal retraction of the contralateral guidewire sheath 216 and, consequently, the contralateral branch sheath 190, through the contralateral iliac artery 38. As illustrated therein, the contralateral branch sheath 190 has been retracted so as to completely deploy the contralateral branch portion 56 of the bifurcated graft 50. The contralateral guidewire 194 may remain coupled to the locking assembly 300 as the contralateral guidewire sheath 216 is withdrawn through the contralateral access site.

Figure 12A:
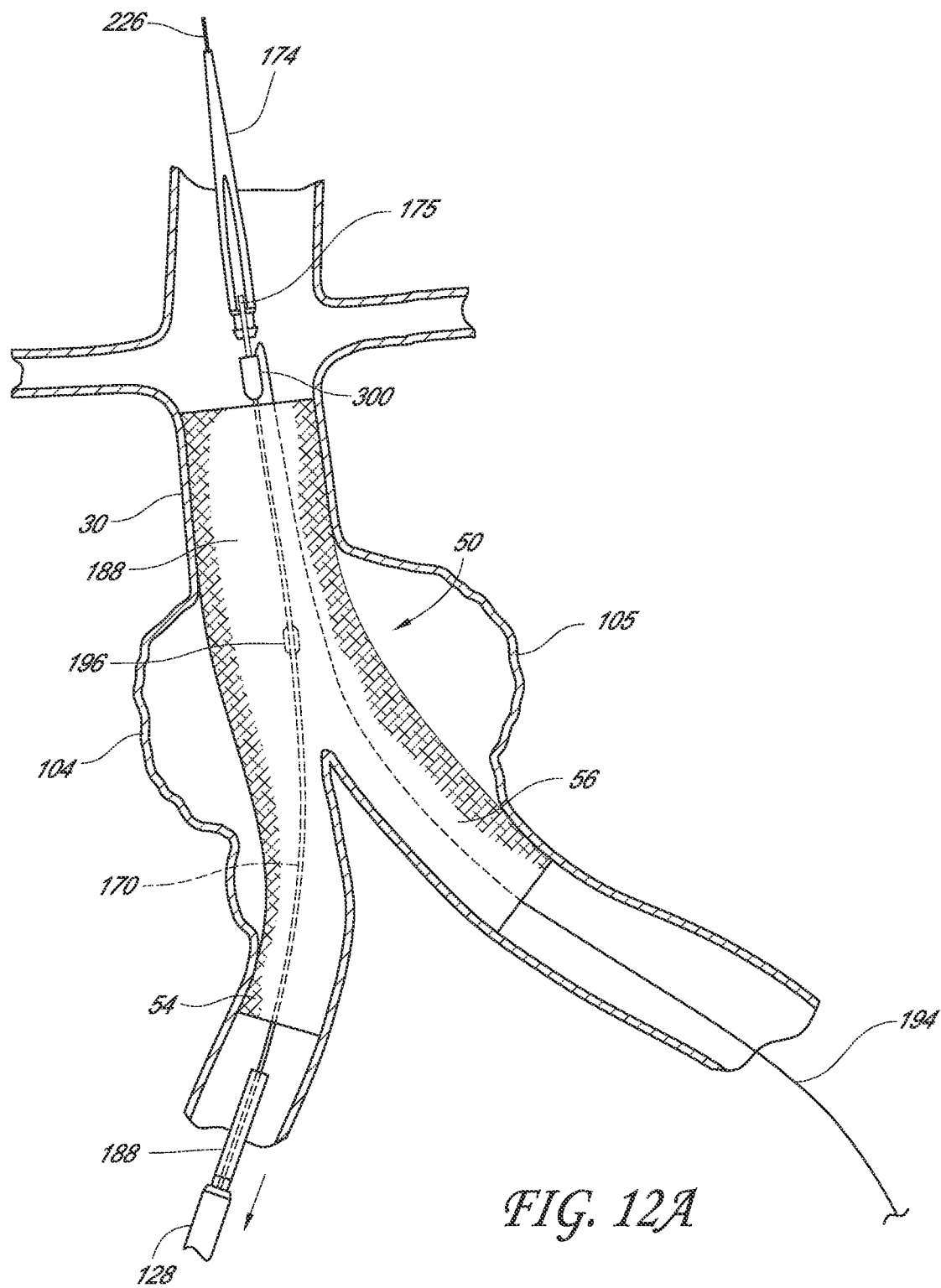
FIG. 12A is a schematic representation, as in FIG. 11, following the proximal retraction of the ipsilateral branch sheath and deployment of the ipsilateral branch portion of the graft.

FIG. 12A is a schematic representation, as in FIG. 11, following the proximal retraction of the ipsilateral branch sheath 188 and deployment of the ipsilateral branch portion 54 of the graft 50. The ipsilateral branch portion 54 of the graft 50 may be deployed by proximally retracting the inner core 132 which, as described above, can be directly or indirectly rigidly attached to the ipsilateral branch sheath 188 (see FIG. 3). Because the ipsilateral branch sheath 188 can be an open-ended tubular sheath, the ipsilateral branch portion 54 of the graft 50 can be deployed in a top down sequence.

However, the ipsilateral branch sheath 188 (and the contralateral branch sheath 190) can be configured to accommodate any other desired or suitable sequence. In some embodiments, the ipsilateral branch portion 54 of the bifurcated graft 50 may be deployed before deployment of the contralateral branch portion 56 of the graft 50. Additionally, although the figures illustrate the main branch portion 52 of the graft 50 being deployed with the contralateral branch portion 56, in other embodiments, the main branch portion 52 of the graft 50 may be deployed with the ipsilateral branch portion 54. Also, although the figures illustrate the ipsilateral branch portion 54 being deployed before the contralateral branch portion 56, in other methods, the contralateral branch portion 56 may be deployed before the ipsilateral branch portion 54 of the graft 50.

In the illustrated embodiment depicted in FIG. 12A, the contralateral guidewire 194 remains coupled to the locking assembly 300 after deployment of the bifurcated graft 50. The locking assembly 300 retains the distal end 194b (shown in FIG. 17A) of the contralateral guidewire 194 to prevent unintended movement of the distal end of the contralateral guidewire 194. The locking assembly 300 can be configured to allow the medical technician to actuate the locking assembly 300, thereby triggering the locking assembly 300 to release the distal end of the contralateral guidewire 194.

Figure 12B:
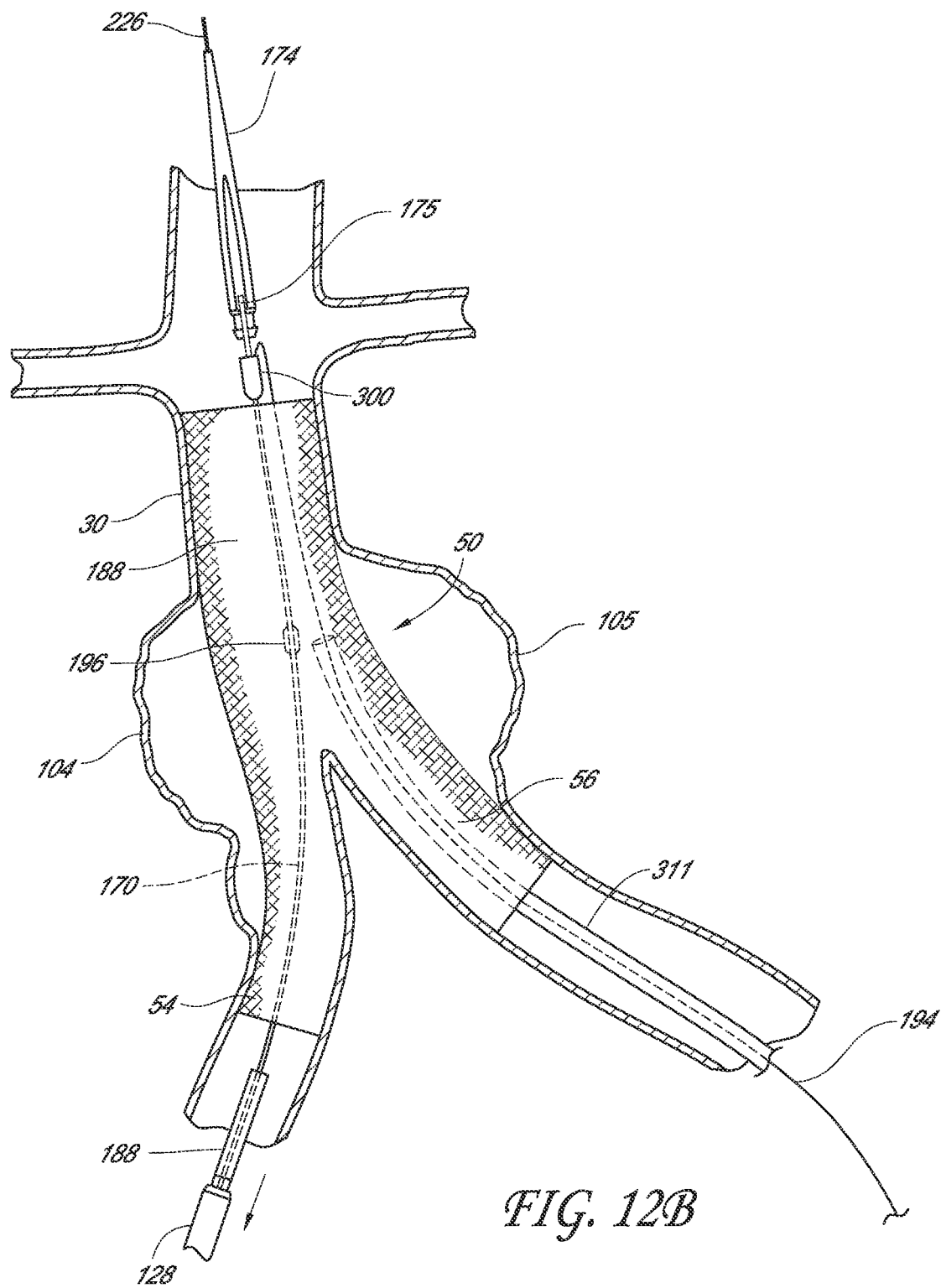
FIG. 12B is a schematic representation, as in FIG. 12A, following introduction of the release member at the contralateral access site and advancement of the release member along the contralateral guidewire.
Figure 12C:
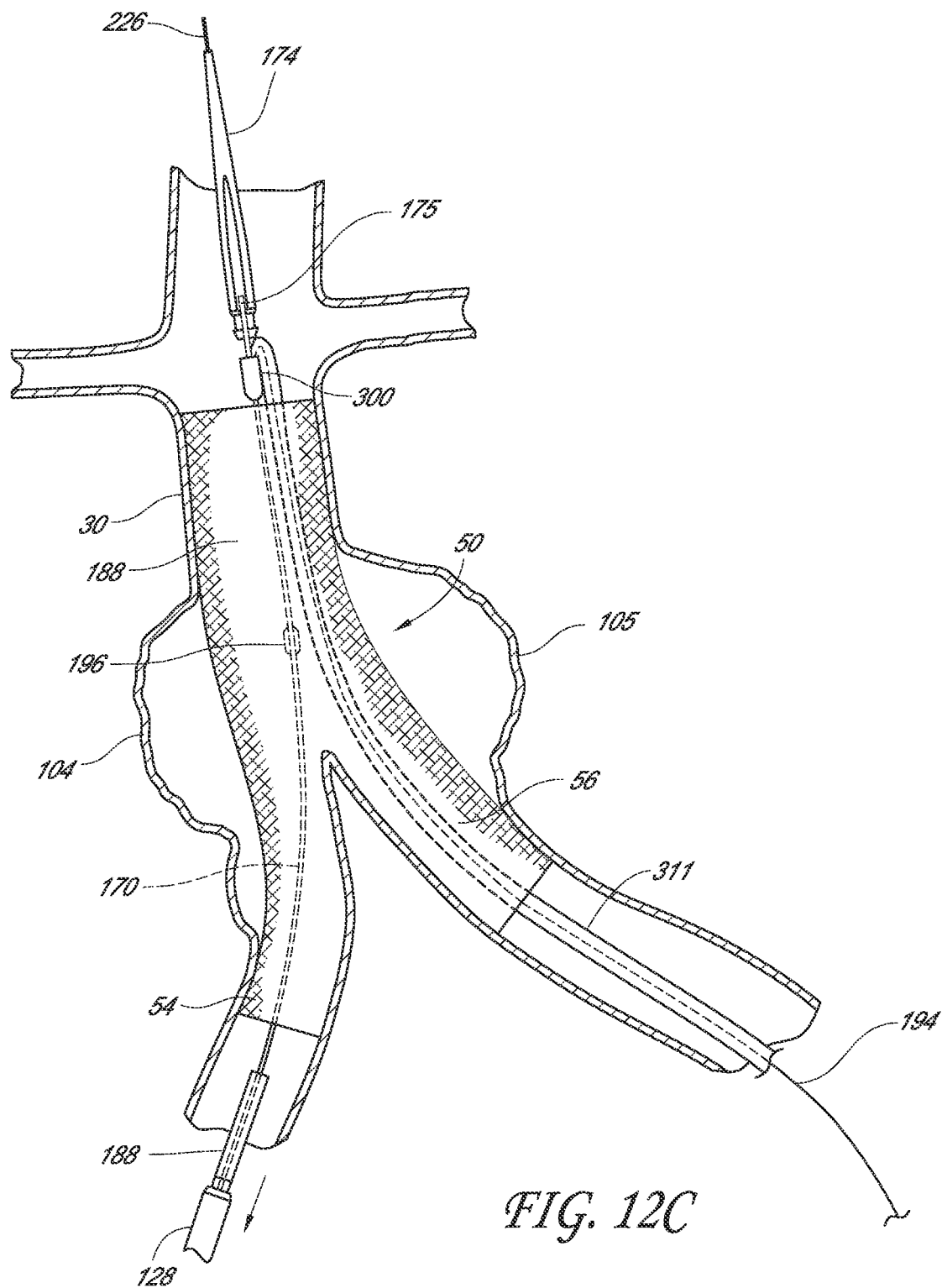
FIG. 12C is a schematic representation, as in FIG. 12B, with a release member interfacing with a locking assembly.
Figure 12D:
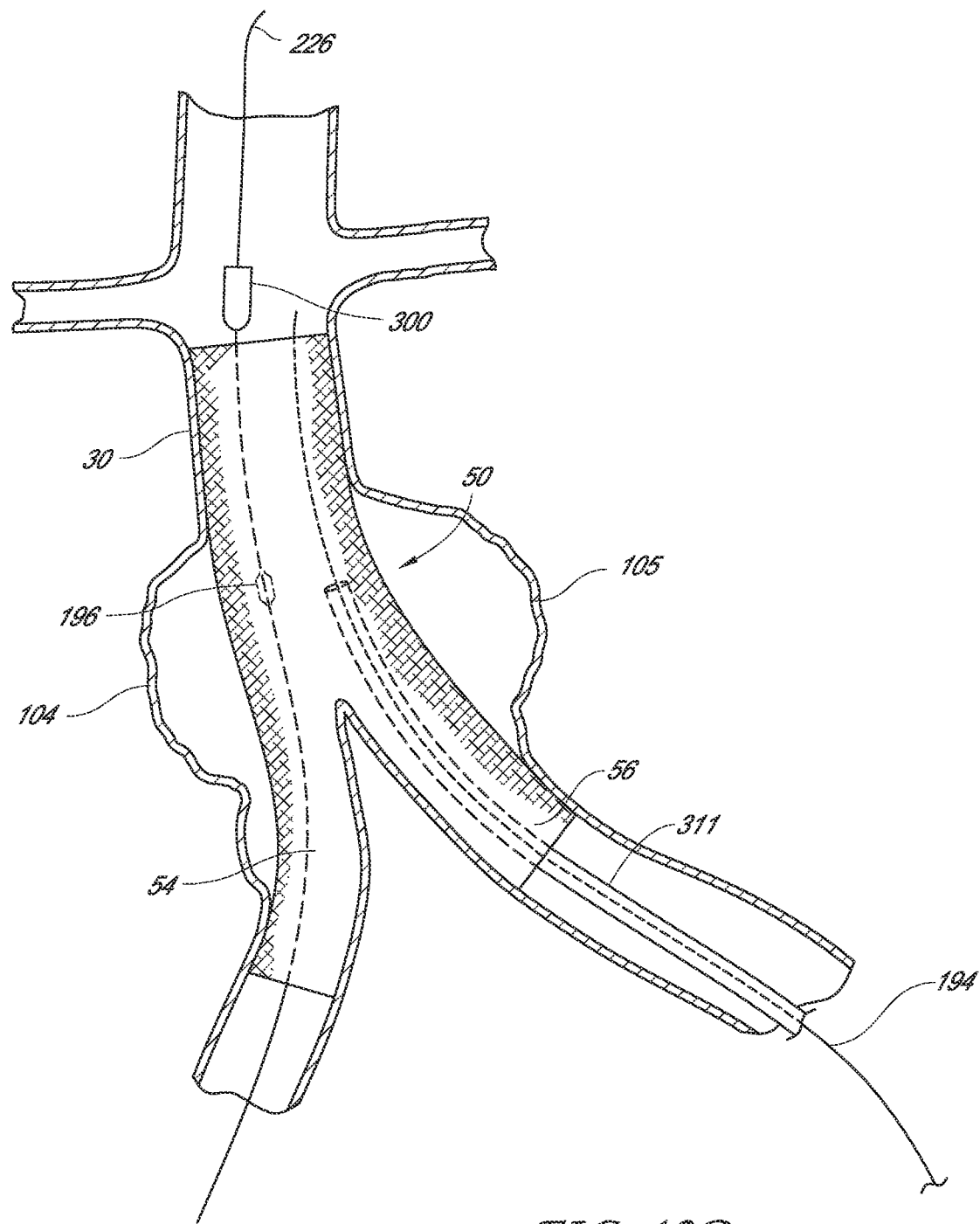
FIG. 12D is a schematic representation, as in FIG. 12C, with a release member being retracted through the contralateral access site following decoupling of the contralateral guidewire from a locking assembly. In some embodiments, a cuff may be implanted (e.g., on a proximal end of the main branch portion) to secure or lengthen the graft.

Referring to FIGS. 12B-D, release of the contralateral guidewire 194 from the locking assembly 300 may be accomplished by advancing a release member 311 (e.g., pigtail catheter) along the contralateral guidewire 194. The release member 311 can then directly or indirectly apply a vertical force to the contralateral guidewire 194, thereby causing the locking assembly 300 to release the distal end 194b of the contralateral guidewire 194. The release member 311 can then be withdrawn through the contralateral access site. The contralateral guidewire 194 can be withdrawn before, after, or at the same time as the withdrawal of the release member 311. Additionally or alternatively, the release member 311 can be configured to release the contralateral guidewire 194 upon the activation of a triggering element that is coupled to the locking device 300, as described below.

Although the illustrated method shows the ipsilateral branch portion 54 of the graft 50 being released before withdrawing the contralateral guidewire 194, in some methods, the contralateral guidewire 194 may be released (e.g., as shown in FIGS. 12B-12D) prior to releasing the ipsilateral branch portion 54 (e.g., as shown in FIG. 12A).

Locking Assembly

Figure 13A:
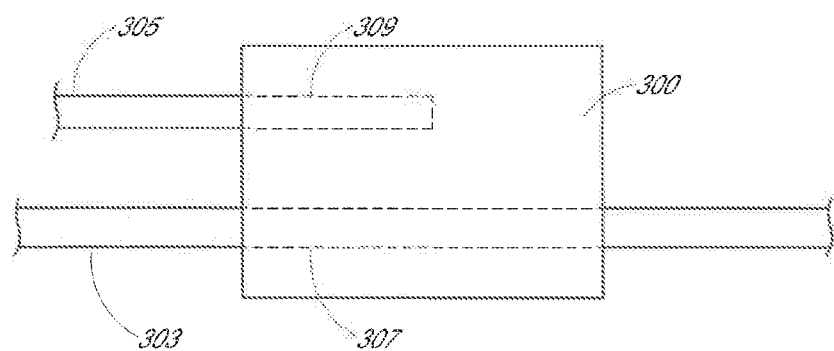
FIG. 13A is a schematic representation of a locking assembly configured to releasably retain an elongate member.

FIG. 13A is a schematic representation of a locking assembly 300. The locking assembly 300 may be interfaced with (e.g., removably coupled, permanently secured, or integrally formed with) a first elongate member 303 and a second elongate member 305. The locking assembly 300 may be configured to interface with more than two elongate members. The first elongate member 303 may pass through the locking assembly 300. The locking assembly 300 can interface with an anchor portion 307 of the first elongate member 303. The locking assembly 300 may reversibly couple to a locking portion 309 of the second elongate member 305.

Figure 13B:
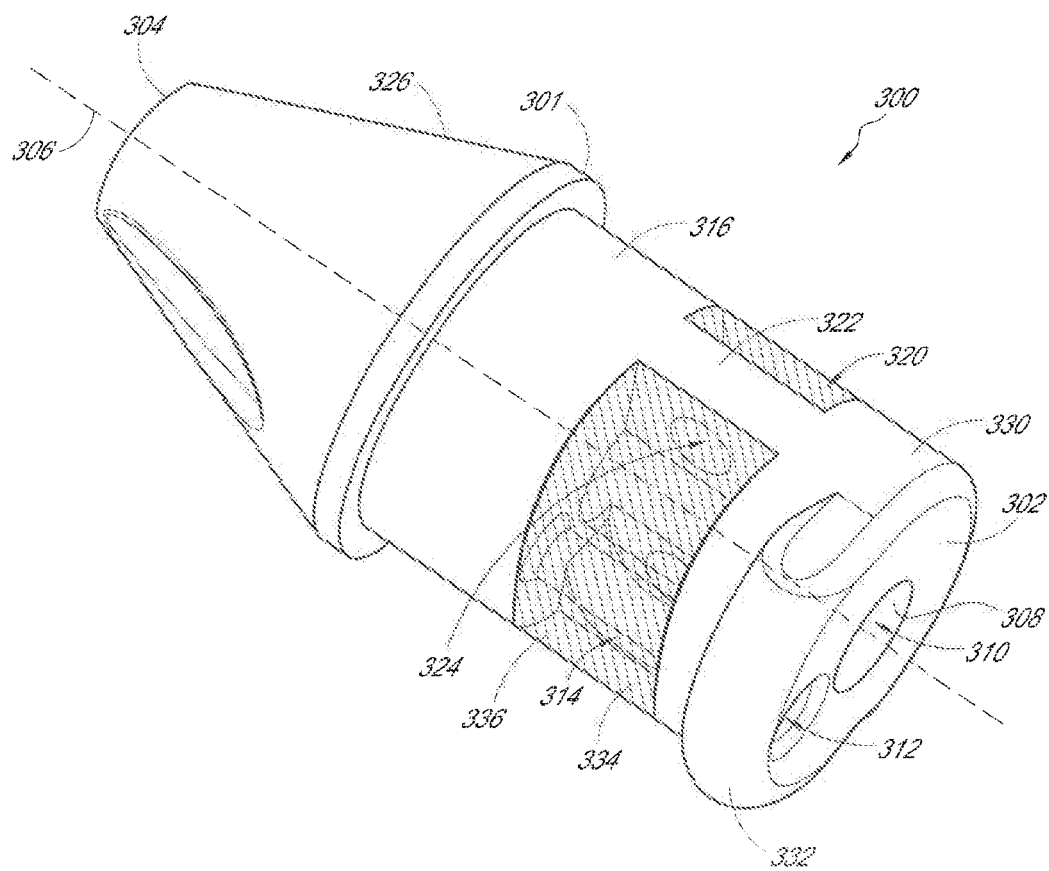
FIG. 13B is an isometric view of an exemplary embodiment of the locking assembly including a housing an elastomeric member.

FIG. 13B is a non-limiting example of a locking assembly 300 that can be used with any embodiment of the deployment catheter 120 disclosed herein. In general, the locking assembly 300 presently disclosed can be configured to secure two elongate members to the locking assembly 300. The locking assembly 300 can be adapted to release one of the elongate members from the locking assembly 300 when a user applies a vertical force to the elongate member being released. The locking assembly 300 presently disclosed can be used in medical procedures that employ a junction of two wires from different locations, such as procedures deploying bifurcated stents or multiple stents in thoracic, renal, or cardiac procedures. By way of a non-limiting example, the locking assembly 300 can be used to join a contralateral guidewire to an ipsilateral catheter when deploying a bifurcated stent in order to treat an abdominal aortic aneurysm. Certain aspects of the locking assembly 300 will now be described by presenting a variety of non-limiting exemplary embodiments of the locking assembly 300.

Referring to FIG. 13B, the locking assembly 300 can include a housing 301 having a distal face 302 and a proximal face 304. As shown in FIG. 13B, the proximal and distal faces 304, 302 may be substantially perpendicular to the longitudinal axis 306. However, in other configurations the proximal and distal faces 304, 302 may not be substantially perpendicular to the longitudinal axis 306 and/or parallel with each other. The locking assembly 300 can include an anchoring surface 308 that defines a first lumen 310. The first lumen 310 may communicate between the distal face 302 and the proximal face 304 of the housing 301. As shown in FIG. 13B, the first lumen 310 may be concentric to the longitudinal axis 306 of the locking assembly 300. However in other configurations, the first lumen 310 may be off-center of the longitudinal axis 306 of the locking assembly 300.

The elongate member can pass through the first lumen 310 of the locking assembly 300, e.g., the central tube 170 of the delivery catheter 120 can pass through the first lumen 310. The locking assembly 300 can be integral with the central tube 170 or bonded to the central tube 170 so that there is no relative movement between the locking assembly 300 and the central tube 170 as the central tube 170 is moved in a distal or proximal direction. The central tube 170 can be secured to the anchoring surface 308 such as by thermal bonding, adhesive bonding, crimping, or any of a variety of other securing techniques known in the art.

Additionally or alternatively, the locking assembly 300 can include a second lumen 312. The second lumen 312 is a passage between the distal face 302 and the proximal face 304 of the housing 301. However, in other configurations, the second lumen 312 may communicate only with the distal face 302, and not with the proximal face 304, of the housing 301. The second lumen 312 can be configured to retain a second elongate member (e.g., the contralateral guidewire 194) to the locking assembly 300. The contralateral guidewire 194 can be released from the second lumen 312 upon activation of the locking assembly 300 by a user.

The locking assembly 300 can include a first recess 314 that extends from a lateral wall 316 of the housing 301 toward the longitudinal axis 306 of the locking assembly 300. The second lumen 312 can communicate with the first recess 314. Additionally or alternatively, the first lumen 310 can communicate with the first recess 314. The locking assembly 300 can include a second recess 320 that extends from the lateral wall 316 of the housing 301 toward the longitudinal axis 306 of the locking assembly 300. The locking assembly 300 can include a divider 322 that is interposed between the first recess 314 and the second recess 320. The locking assembly 300 can include a through-hole 324 that extends through the divider 322 and communicates between the first and second recesses 314, 320 to form a recessed portion.

A proximal portion 326 of the locking assembly 300 can be tapered. The proximal portion 326 can be tapered so that the transverse cross-sectional area of the proximal portion 326 decreases along the proximal direction. The proximal portion 326 can be tapered to allow the proximal portion 326 to be withdrawn out of the graft 50 and back into the outer sheath 128 without having the locking assembly 300 getting caught on the graft 50 or the outer sheath 128 or any other intervening structure. The locking assembly 300 can have a taper angle defined as the angle between the longitudinal axis 306 of the locking assembly 300 and the lateral wall of the proximal portion of the locking assembly 300. The taper angle can be between about 15 and 60 degrees, between about 20 and 45 degrees, and between about 25 and 35 degrees. The taper angle can be 30 degrees with a tolerance of 1 degree.

A distal portion 330 of the locking assembly 300 can include a protrusion 332, extending radially outward from housing 301. The protrusion 332 may circumferentially surround the entire distal portion 330 of the locking assembly 300, or may surround only a portion of the distal portion 330 of the locking assembly 300. The protrusion 332 may extend from only a portion of the distal portion 330. The second lumen 312 can be interposed between the protrusion 332 and the first lumen 310. The protrusion 332 can be configured to provide strain relief to an elongate member that extends distally from the second lumen 312 and then bends back in the proximal direction. The protrusion 332 can have a radius of curvature between about 0.005 and 0.1 inches, between about 0.01 and 0.05 inches, and between about 0.015 and 0.025 inches. The protrusion 332 can have a radius of curvature of 0.02 inches with a tolerance of 0.01 inches.

The locking assembly 300 can have a length dimension that defines the distance between the proximal and distal faces 304, 302. The length dimension can be between about 0.1 and 1.0 inches, between about 0.2 and 0.5 inches, and between about 0.3 and 0.4 inches. The length dimension can be 0.375 inches with a tolerance of 0.010 inches. The locking assembly 300 can have a width dimension perpendicular to the length dimension. The width dimension can be between about 0.05 and 0.5 inches, between about 0.1 and 0.3 inches, and between about 0.15 and 0.2 inches. The width dimension can be 0.187 inches with a tolerance of 0.002 inches. The locking assembly 300 can have a first aspect ratio defined as the length dimension divided by the width dimension. The first aspect ratio can be between about 0.5 and 5, between about 1 and 3, and between about 1.75 and 2.25. The first aspect ratio can be 2.0.

The first lumen 310 of the locking assembly 300 can have a diameter of between about 0.01 and 0.2 inches, between about 0.02 and 0.1 inches, and between about 0.04 and 0.06 inches. The first lumen 310 can have a diameter of 0.055 inches with a tolerance of 0.002 inches. The second lumen 312 of the locking assembly 300 can have a diameter of between about 0.01 and 0.1 inches, between about 0.02 and 0.05 inches, and between about 0.03 and 0.04 inches. The second lumen 312 can have a diameter of 0.033 inches with a tolerance of 0.002 inches. The locking assembly 300 can have a second aspect ratio defined as the diameter of the first lumen 310 divided by the diameter of the second lumen 312. The second aspect ratio of the locking assembly 300 can be between about 1 and 3, between about 1.5 and 2. The second aspect ratio of the locking assembly 300 can be 1.667. The center points of the first and second lumens can be separated from one another by a spacing dimension. The spacing dimension can be between about 0.04 and 0.07 inches, and between 0.05 and 0.06 inches. The spacing dimension can be 0.053 inches with a tolerance of 0.002 inches.

The locking assembly 300 can include an elastomeric member 334. The elastorneric member 334 may occupy at least a portion of the first recess 314. The elastomeric member 334 can have an outer surface 336 that is flush with at least a portion of the lateral wall of the locking assembly 300. The first recess 314 can be configured to retain the elastomeric member 334 within the locking assembly 300. Additionally or alternatively, the elastomeric member 334 may occupy at least a portion of the second recess 320. The second recess 320 can be configured to retain the elastomeric member 334 within the locking assembly 300. The elastomeric member 334 can be configured to span the divider 322. The elastomeric member 334 can have a first portion that resides in the first recess 314 while a second portion of the elastomeric member 334 resides in the second recess 320, the first and second portions of the elastomeric member 334 being connected by a segment of the elastorneric member 334 that extends through the through-hole 324.

The elastomeric member 334 can be configured to enhance the ability of the second lumen 312 to retain the contralateral guidewire 194 of the delivery catheter 120. For example, the elastomeric member 334 can be configured to intrude into at least a portion of the second lumen 312. The locking assembly 300 can be configured so that at least a portion of the elastomeric member 334 can interface with an elongate member inserted into the second lumen 312. The elastomeric member 334 may form a friction fit with an elongate member inserted into the second lumen 312, helping to retain the elongate member in the second lumen 312. Different non-limiting exemplary embodiments of the elastomeric member 334 are discussed below.

Figure 14:
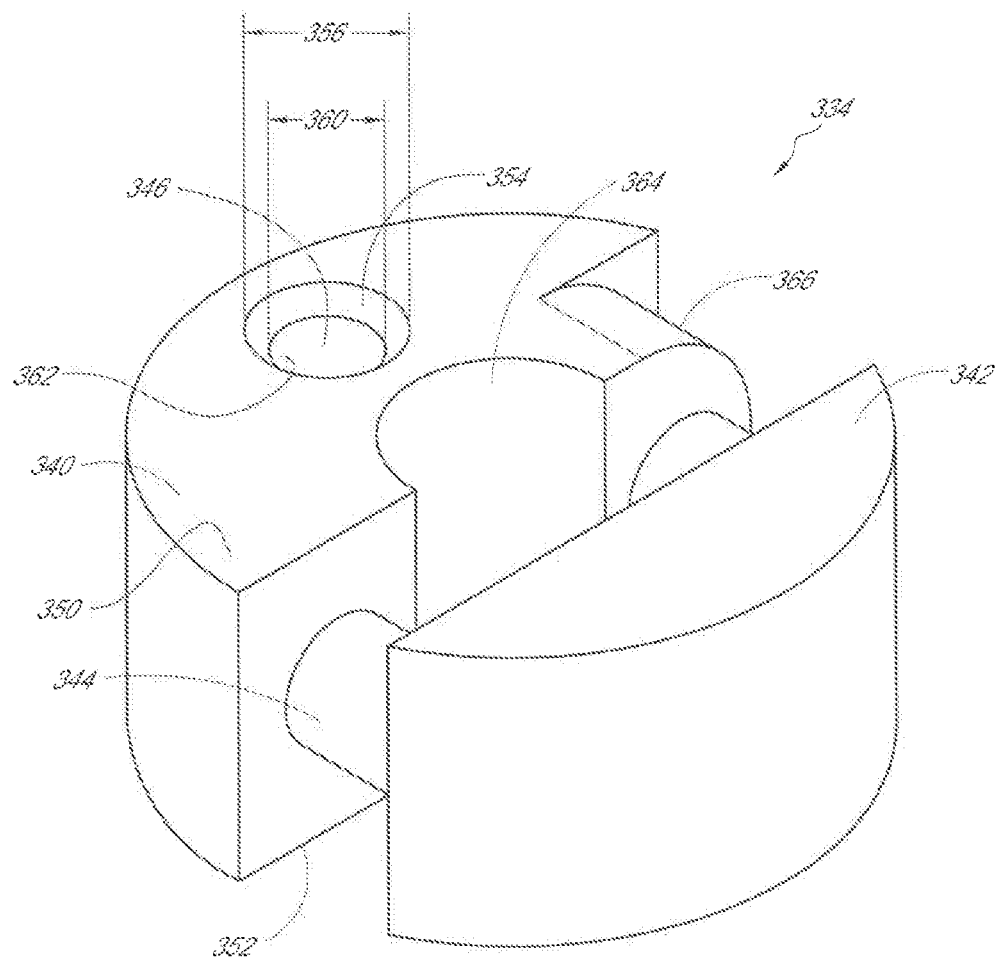
FIG. 14 is an isometric view of an embodiment of the elastomeric member shown in FIG. 13B.

FIG. 14 shows an isometric view of one exemplary embodiment of the elastomeric member 334. The elastomeric member 334 can include a first portion 340 that is configured to be retained within the first recess 314 of the locking assembly 300. Additionally or alternatively, the elastomeric member 334 may include a second portion 342 that is configured to be retained within the second recess 320 of the locking assembly 300. The first portion 340 can be connected to the second portion 342 by at least one segment 344. In the non-limiting exemplary example depicted in FIG. 14 the elastomeric member 334 can include a first portion 340 joined to a second portion 342 by two segments 344, the segments 344 being cylindrical in shape. The elastomeric member 344 can include a segment 344 having a shape other than cylindrical. The second portion 342 and the segment 344 can be configured to enhance retention of the elastomeric member 334 within the housing 301 of the locking assembly 300. The second portion 342 can provide a mechanical lock between the elastomeric member 334 and the housing 301 of the locking assembly 300, thereby increasing the strength of the attachment between the elastomeric member 334 and the housing 301.

The elastomeric member 334 can include a retention portion 346 configured to retain a second elongate member 305 that is inserted into the second lumen 312 of the locking assembly 300. The retention portion 346 can define an opening 348 (e.g., through-hole, lumen, or otherwise) that extends at least partially through the elastomeric member 334, e.g., between a distal face 350 and a proximal face 352 of the elastomeric member 334 or only in communication with the distal face 350 of the elastomeric member 334. The opening 348 can be concentric with the second lumen 312 of the locking assembly 300 when the elastomeric member 334 is seated within the first recess 314 of the locking assembly 300.

An end portion of the opening 348 has a diameter 356 that can be larger than an intermediate diameter 360 of an intermediate portion 362 of the retention portion 346. The end portion 354 of the retention portion 346 can be configured to guide an elongate member into the intermediate portion 356 of the retention portion 346. The end portion 354 of the retention portion 346 can include a canted wall that funnels an inserted elongate member into the intermediate portion 356 of the retention portion 346.

The elastomeric member 334 can include a passageway defined by a curved surface 364 that aligns with the first lumen 310 of the locking assembly 300. The curved surface 364 of the elastomeric member 334 can interface with (e.g., by bonding) the housing 301 of the locking assembly 300. The housing 301 of the locking assembly can interface with (e.g., by welding) to the elongate member that passes through the first lumen of the locking assembly 300.

The elastomeric member 334 can include a curved portion 366. The curved portion 366 can be configured to enhance the bonding between the elastomeric member 334 and the housing 301 of the locking assembly 300. FIG. 14A is a top view of the elastomeric member 334 depicted in FIG. 14. FIG. 14B is an offset rear view of the elastomeric member 334 depicted in FIG. 14, showing the curved portion 366 in more detail. FIG. 14C is a front cross-sectional view of the elastomeric member 334 depicted in FIG. 14. FIG. 14D is an offset front view of the elastomeric member 334 depicted in FIG. 14.

Figure 15:
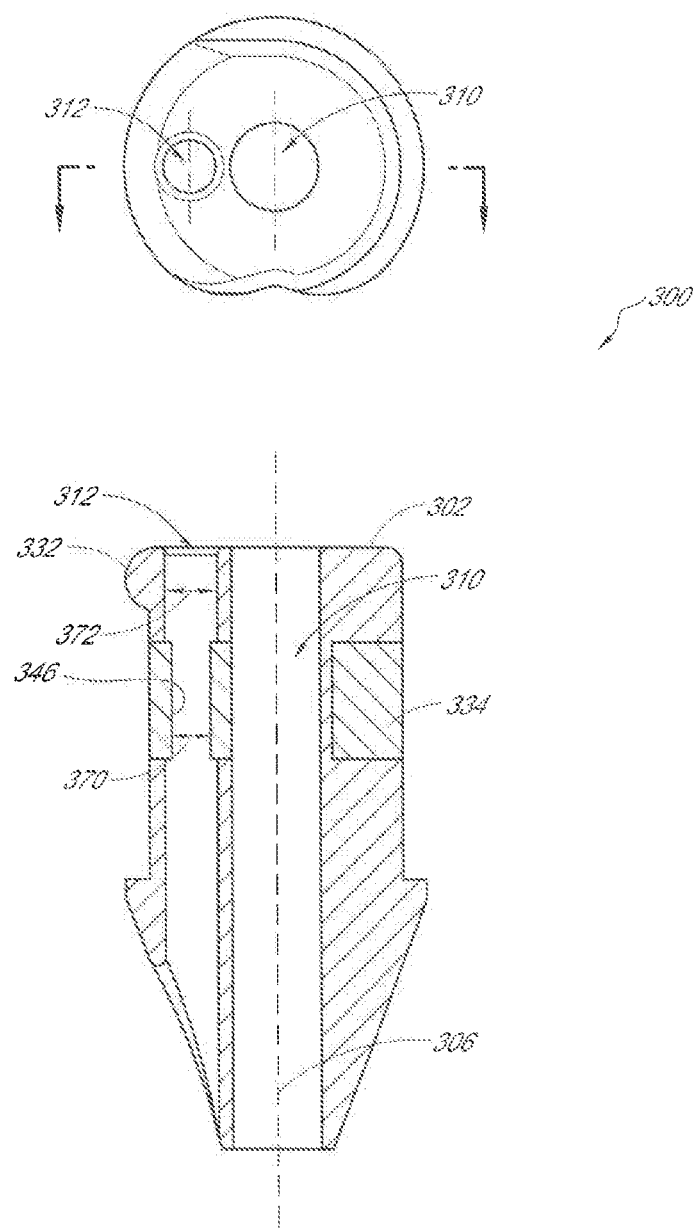
FIG. 15 is a front cross-sectional view of an embodiment of the present locking assembly.

FIG. 15 depicts a cross-sectional view of an exemplary embodiment of the locking assembly 300. The elastomeric element 334 can include a retention portion 346 that at least partially aligns with the second lumen 312. The retention portion 346 can include an opening 348 having a width 370. The width 370 of the passageway of the retention portion 346 can be smaller than the width 372 of the second lumen 312, thereby causing at least a portion of the retention portion 346 to intrude upon the second lumen 312. The retention portion 346 can define an opening 348 that partially aligns with the second lumen 312. For example, the retention portion 346 may intrude upon the second lumen 312 from only one side. In some configurations, the retention portion 346 can be cup-shaped, with the mouth of the cup-shaped retention portion 346 facing the distal surface 302 of the locking assembly 300.

As discussed, in some embodiments, the retention portion 346 can include an opening 348 formed within the elastomeric member 334. The elastomeric member 334 can be made of an elastic material such as silicone. The opening 348 of the retention portion 346 can stretch and/or compress to accommodate an elongate member inserted into the retention portion 346. The retention portion 346 can be configured to form a friction fit with an elongate member inserted into the opening 348 of the retention portion 346. The friction fit between the retention portion 346 and the elongate member can resist distal movement of the elongate member relative to the retention portion 346 until the elongate member is subjected to sufficient tension in the distal direction.

Figure 16:
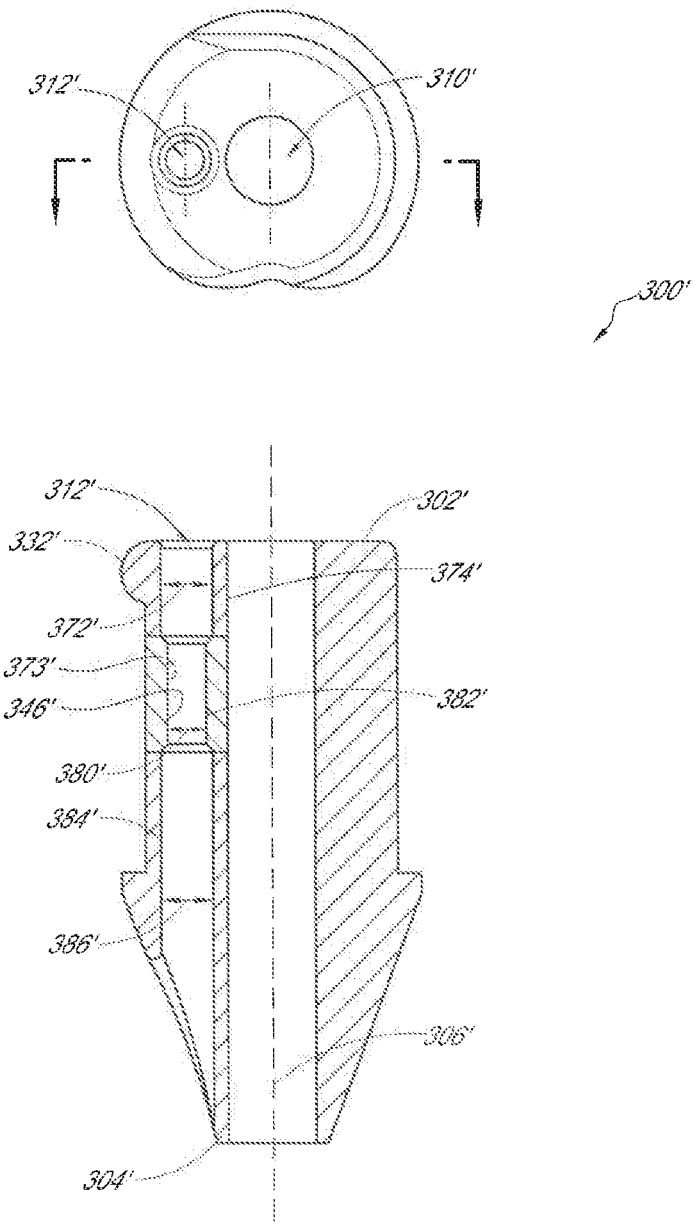
FIG. 16 is a front cross-sectional view of an alternative embodiment of the present locking assembly.

FIG. 16 depicts a cross-sectional view of a non-limiting alternative embodiment of the locking assembly 300' that includes the housing 301' but not include an elastomeric member 334'. The housing 301' can be substantially similar to that described above except without a recessed portion configured to receive the elastomeric member. In this embodiment, the locking assembly 300' can include a retention portion 346' which can include the second lumen 312'. The second lumen 312' can have a uniform cross-sectional area or a non-uniform cross-sectional area (e.g., a constriction of the second lumen 312'). A distal portion 374' of the second lumen 312' can have a width 376' that is greater than a width 380' of an intermediate portion 382' of the second lumen 312'. The second lumen 312' may include a proximal portion 384' that is proximal of the intermediate portion 382' of the second lumen 312'. The proximal portion 384' can have a width 386' that is greater than the width 380' of the intermediate portion 382'. The operation of the retention portion 346' is discussed below.

Figure 17A:
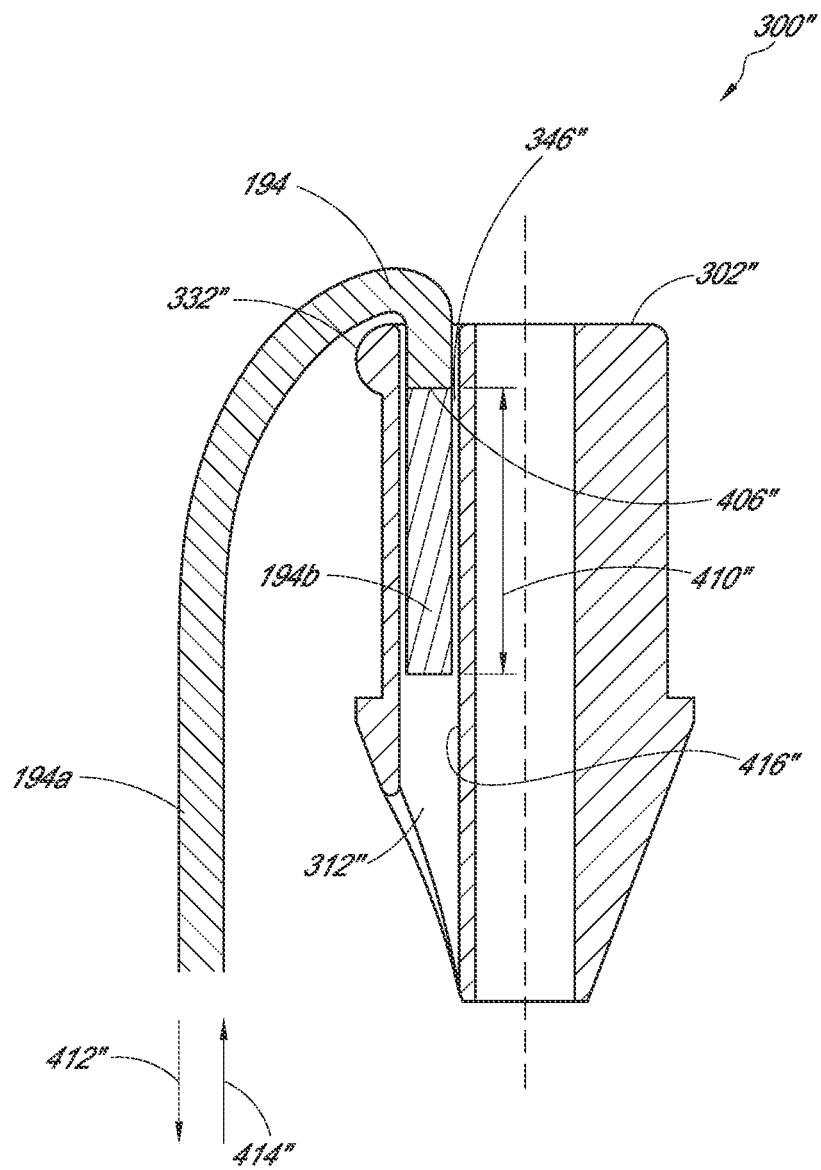
FIG. 17A is a front view of an embodiment of a locking assembly coupled to a contralateral guidewire.
Figure 17B:
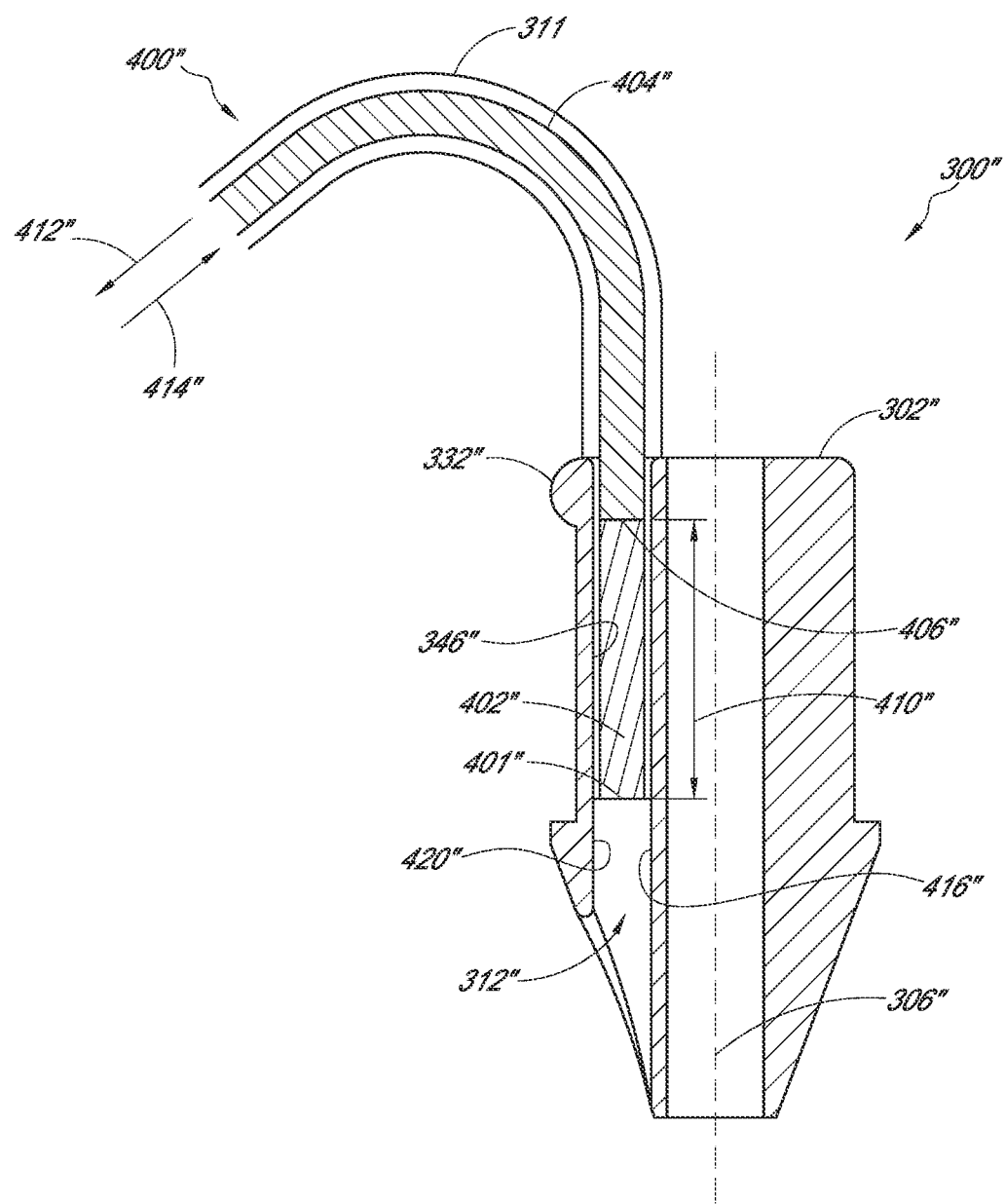
FIG. 17B is a front view of the embodiment depicted in FIG. 17A interfacing with a release member.

FIGS. 17A and 17B schematically illustrate a method of releasing the guidewire from the locking assembly 300 that can be used in connection with both the locking assemblies with and without the elastomeric member (shown in FIGS. 15 and 16). Although these figures illustrate the second lumen 312" having a generally uniform diameter, the diameter may vary as shown in FIG. 16. FIG. 17A depicts a non-limiting exemplary embodiment of the locking assembly 300" with a distal portion 194b (also called the locking portion) of the contralateral guidewire 194 inserted into the second lumen 312" of the locking assembly 300". When the contralateral guidewire 194 is inserted into the locking assembly 300", general advancement and retraction of the contralateral guidewire 194 without the appropriate vertical force and/or actuation will not release the contralateral guidewire 194 from the locking assembly 300".

The contralateral guidewire 194 can include multiple regions, with each region having a different stiffness. For example, the stiffness of the locking portion 194b of the contralateral guidewire 194 can be selected to be higher than the stiffness of a proximal portion 194a (also called the floppy region) of the contralateral guidewire 194. 194194194194 By designing the floppy region 194a to have a low stiffness, the a proximal portion 194a of the contralateral guidewire 194 will be sufficiently flexible to avoid causing damage to surrounding tissue. The tensile strength of the floppy region 194a can be greater than about 1 lbf, greater than about 2 lbf, greater than about 6 lbf, and greater than about 8 lbf.

The locking portion 194b of the contralateral guidewire 194 can extend from the floppy region 194a of the contralateral guidewire 194 at an interface 406". The length 410" of the locking portion 194b can be selected from different lengths. In some embodiments, the length of the locking portion 194b" can be between about 0.3 and 0.8 cm. Additionally or alternatively, the insertion depth of the locking portion 194b into the second lumen 312" can be adjusted. The contralateral guidewire 194 and the locking assembly 300" may be tailored so that the interface 406" can be located distal, proximal, or co-planar to the distal face 302" of the locking assembly 300".

During use, a user may pull on the contralateral guidewire 194, creating a tension 412" in the contralateral guidewire 194, thereby causing the contralateral guidewire 194 to bend in the proximal direction, as illustrated in FIG. 17A. Additionally or alternatively, a user may push on the contralateral guidewire 194, causing a compressive force 414" that buckles the contralateral guidewire 194 in the distal direction, thereby pushing the locking portion 194b into the retention portion 346". The locking assembly 300" can include a protrusion 332" that provides strain relief to the contralateral guidewire 194 when the contralateral wire 194 bends back in the proximal direction. The position of the interface 406" relative to the distal face 302" of the locking assembly 300" can be selected so that as the tension 412" pulls on the interface 406", the locking portion 194b of the contralateral guidewire 194 is retained against a lateral surface 416" of the retention portion 346", thereby preventing the contralateral guidewire 194 from decoupling from the locking assembly 300". The clearance between the locking portion 194b and the lateral surface 416" can also be selected to further define the tension 412" required to decouple the contralateral guidewire 194 from the locking assembly 300". The locking assembly 300" can be configured to release the locking portion 194b of the contralateral guidewire 194 when a force is applied to an intermediate portion of the contralateral guidewire 194 at an angle of less than or equal to about 60 degrees from the locking portion 194b of the contralateral guidewire 194 and/or at least about 45 degrees from the locking portion 194b" of the contralateral guidewire 194".

FIG. 17B shows an illustrative embodiment of a locking assembly 300" that is configured to release the contralateral guidewire 194 upon a release member 311 (e.g., pigtail catheter) contacting with the locking assembly 300" and applying a vertical force to draw the locking portion 194b of the contralateral guidewire 194 out of the retention portion 346". In the non-limiting exemplary locking assembly 300" depicted in FIG. 17B, the release member 311 can be a release sheath that is configured to be disposed over the contralateral guidewire 194. The release member 311 may completely circumferentially surround the contralateral guidewire 194, or the release member 311 may only partially circumferentially surround the contralateral guidewire 194. The release member 311 may be composed of plurality of segments. The segments may be identical to one another or different from one another. Some, all, or no segments may completely circumferentially surround the contralateral guidewire 194 while some, all, or no other segments only partially surround the contralateral guidewire 194. The segments may be separated from one another by one or more hinge points. The hinge points may be configured to allow the segments to bend, flex, or pivot relative to one another.

The release member 311 can be introduced at the contralateral access site by passing the distal end of the release member 311 over the proximal end of the contralateral guidewire 194. The release sheath 420" can be advanced over the contralateral guidewire 194 until the distal face of the release member 311 engages the distal face 302" of the locking assembly 300". The outer diameter of the distal face of the release member 311 can be selected so that the distal face abuts against the distal face 302" of the locking assembly. As a user applies a compressive force 414" to the release member 311 and contralateral guidewire 194, the release member 311 buckles in the distal direction. As the release member 311 buckles (loops, forms a U-shape, or otherwise bends) in the distal direction, the portion of the contralateral guidewire 194 that distally extends from the retention member 346" of the locking assembly 300" is aligned to be substantially perpendicular to the distal face 302" of the locking assembly 300". A user may now apply tension 412" to the contralateral guidewire 194. Once a distally extending portion of the contralateral guidewire 194 is longitudinally aligned with the retention member 346", the 194 the contralateral guidewire 194 is released from the retention member 346". The locking assembly 300" can be configured to retain the contralateral guidewire 194 until a vertical force of at least 0.1 lbf (or at least about 0.5 lbf, at least about 1.0 lbf, or otherwise) is applied to the contralateral guidewire 194.

The reversible coupling of the contralateral guidewire 194 to the locking assembly 300 can be accomplished by alternative embodiments that are within the scope of the present disclosure. For example, the locking assembly 300" depicted in FIGS. 17A-B can include an elastomeric member 334, as discussed above. Additionally or alternatively, the locking assembly 300 can include any of the features depicted in the alternative embodiments depicted in FIGS. 18A-R.

Figure 18A:
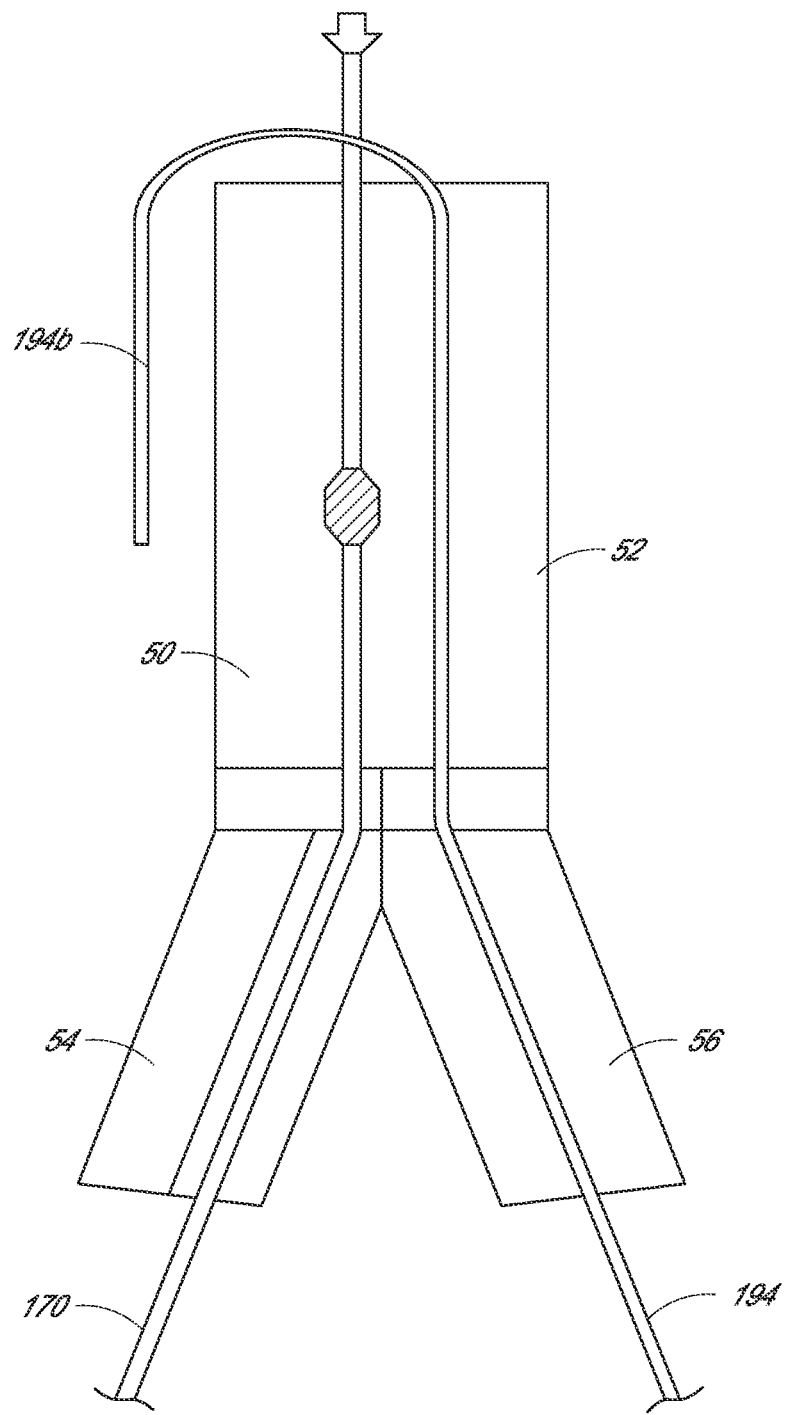
FIG. 18A is an alternative embodiment of the locking assembly presently disclosed.

FIG. 18A depicts an embodiment where the locking portion 194b of the contralateral guidewire 194 is retained by wrapping the locking portion 194b of the contralateral guidewire 194 over the main branch portion 52 of the graft 50. The locking portion 194b can be secured to the outer surface of the main branch portion 52 by a sheath (not shown) that is deployed by a suture (not shown) as described above for the deployment of the main branch portion 52 of the graft 50. The locking portion 194b may be larger in diameter, longer, and/or more rigid than remaining portions of the contralateral guidewire 194. The sheath that secures the locking portion 194b can be the main branch sheath 186 or a sheath different from the main branch sheath 186.

Figure 18B:
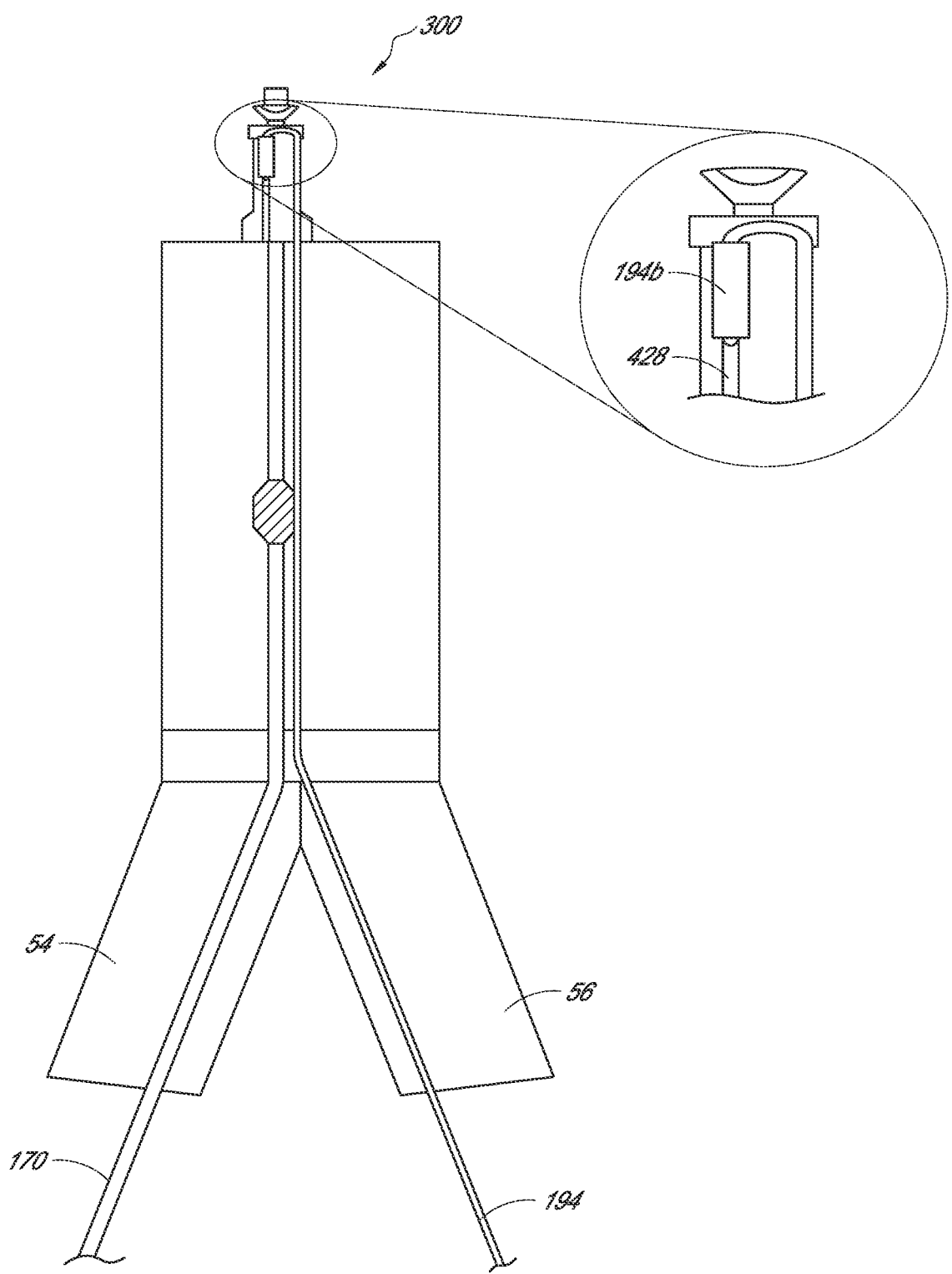
FIG. 18B is an alternative embodiment of the locking assembly presently disclosed.

FIG. 18B depicts an embodiment of the locking assembly 300 that can have a track 428 configured to retain the locking portion 194b of the contralateral guidewire 194. The locking portion 194b may be larger and/or more rigid than a remaining portion of the contralateral guidewire 194 to help retain the locking portion 194b within the track 428. The track 428 may be an open faced channel having a variable width so that when tension is applied to the contralateral guidewire 194 the locking portion 194b is drawn up into a necked region of the track 428, thereby constraining the locking portion 194b from escaping the track 428. Additionally or alternatively, a region of the track 428 may be an open faced channel having an enlarged region where the width of the track 428 is larger than the width of the locking portion 194b. A user may free the contralateral guidewire 194 from the locking assembly 300 by advancing the locking portion 194b of the contralateral guidewire 194 until the locking portion 194b is aligned with the enlarged region of the track 428, thereby allowing the locking portion 194b to escape the track 428.

Figure 18C:
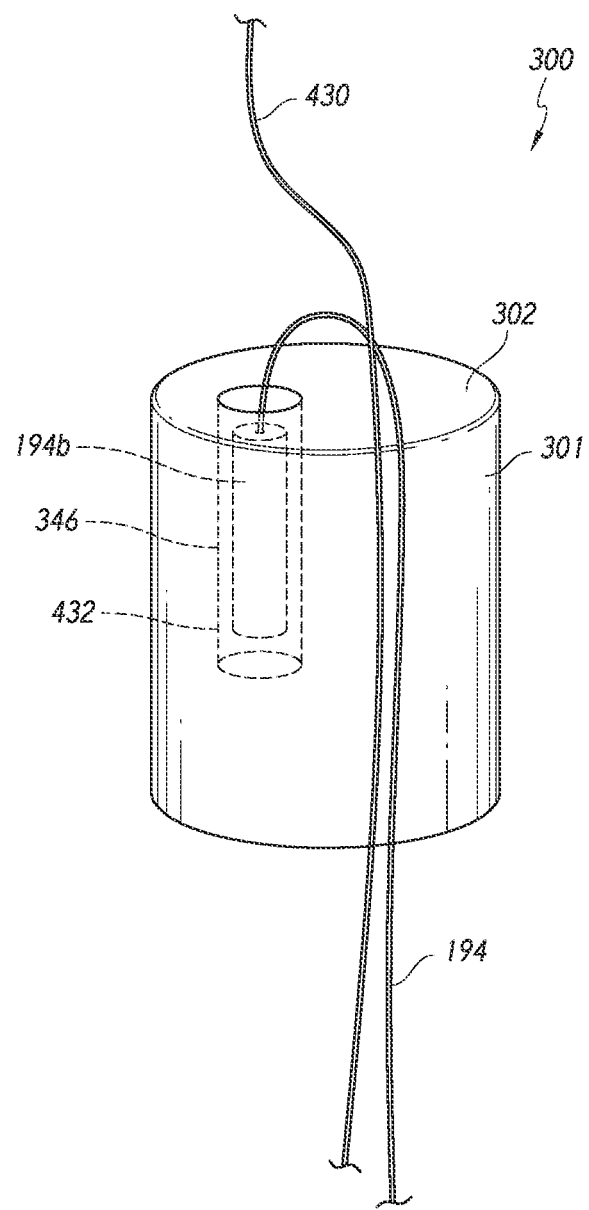
FIG. 18C is an alternative embodiment of the locking assembly presently disclosed.

FIG. 18C depicts an embodiment of the locking assembly 300 that has a retaining wire 430. The retaining wire 430 can be configured to hold the contralateral guidewire 194 against the distal face 302 of the locking assembly 300, thereby keeping the locking portion 194b within the retention portion 346 of the locking assembly 300. The retention portion 346 can be a groove on the side of the housing 301 of the locking assembly 300. The retention portion 346 may be a pocket 432 that is surrounded by the housing 301. The width of the groove or pocket 432 may vary as described above. The retaining wire 430 can be configured to be withdrawn from the locking assembly 300, thereby allowing the locking portion 194b to potentially release from the pocket 432.

Figure 18D:
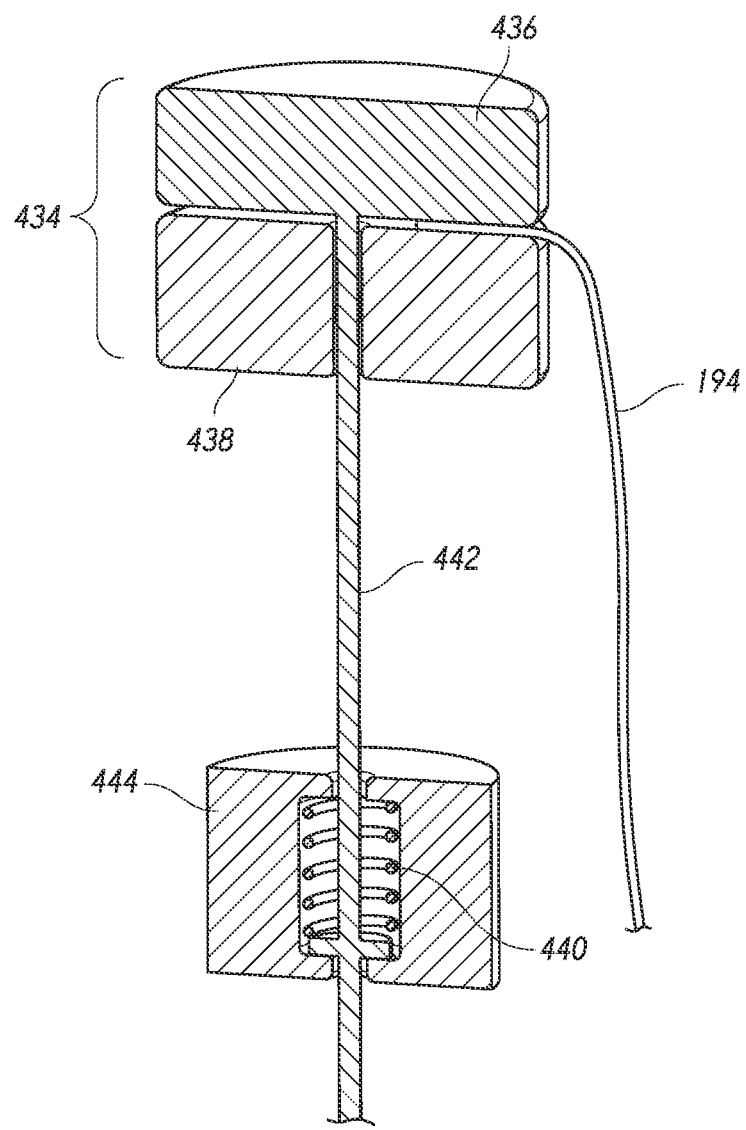
FIG. 18D is an alternative embodiment of the locking assembly presently disclosed.

FIG. 18D depicts an embodiment of the locking assembly 300 that has a clamp 434. The top portion 436 of the clamp 434 may be pulled against the bottom portion 438 of the clamp 434 by a spring 440 that is connected to the top portion 436 by a tension element 442. The contralateral guidewire 194 may be coupled to the locking assembly 300 by virtue of being compressed between the top and bottom portions 436, 438 of the clamp 434. A user may activate a trigger 444 to compress the spring 440 reducing the tension element, thereby reducing the compressive force between the top and bottom portions 436, 438 of the clamp 434 and allowing the contralateral guidewire 194 to decouple from the locking assembly 300. In other embodiments, the tension in the spring 440 may be released by moving the trigger 444 or by releasing the tension on the spring 440.

Figure 18E:
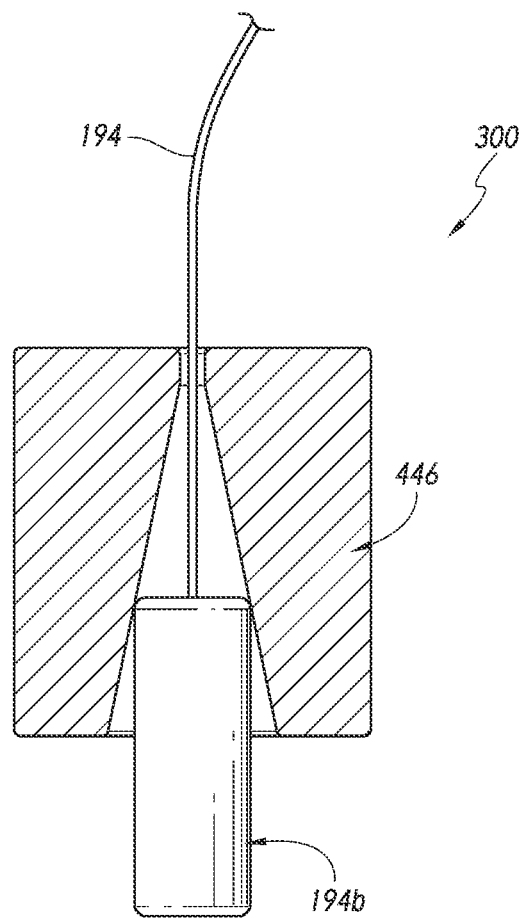
FIG. 18E is an alternative embodiment of the locking assembly presently disclosed.

FIG. 18E depicts an embodiment of the locking assembly 300 having a duckbill valve 446. The duckbill valve 446 can be configured to retain a locking portion 194b at the distal end of the contralateral guidewire 194. The locking portion 194b may be larger and/or more rigid than a remaining portion of the contralateral guidewire 194. A user may decouple the contralateral guidewire 194 from the locking assembly 300 by advancing the contralateral guidewire 194 to allow the locking portion 194b to escape the duckbill valve 446.

Figure 18F:
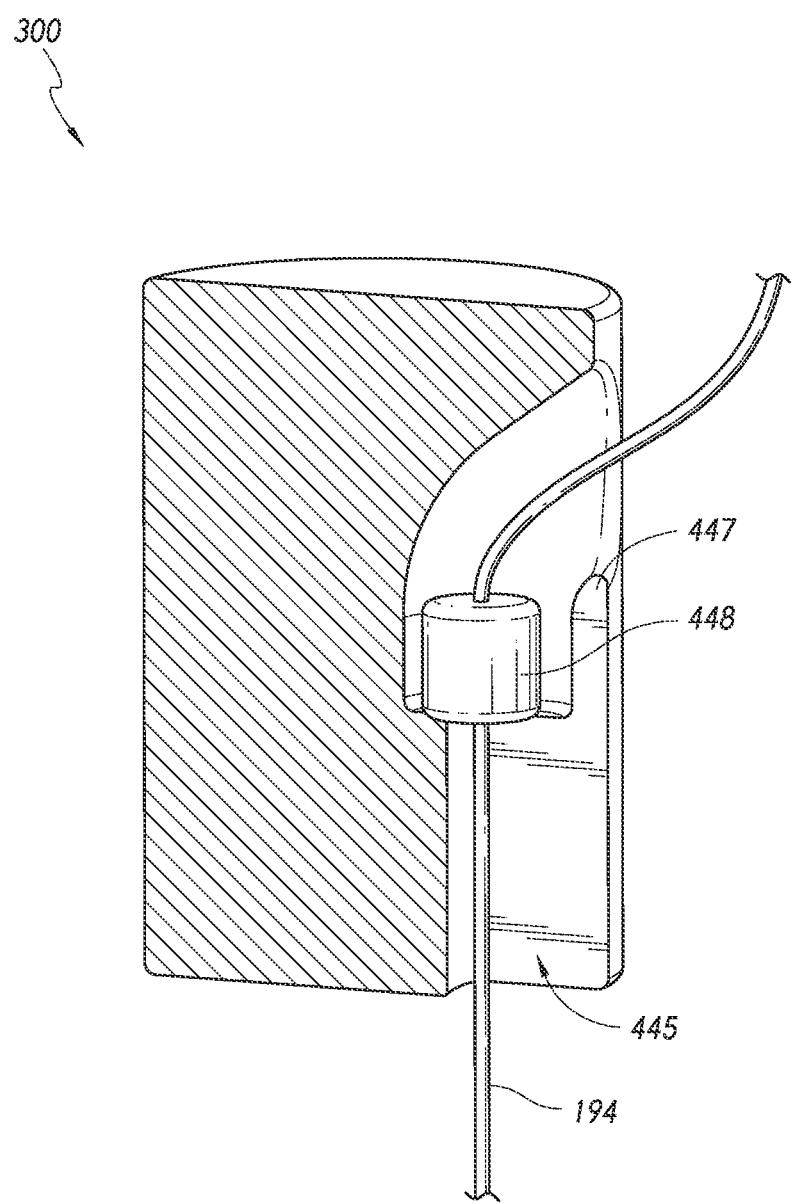
FIG. 18F is an alternative embodiment of the locking assembly presently disclosed.

FIG. 18F depicts an embodiment of the locking assembly 300 configured to retain a bead 448 attached to the contralateral guidewire 194. The bead 448 can interface with (e.g., by bonding) the contralateral guidewire 194. As shown in FIG. 18F, the bead 448 can sit within a channel 445 that has a narrow proximal portion and a wider distal portion. The narrow proximal portion of the channel 445 can be configured to prevent the bead 448 from being pulled proximally through the channel. The wider portion of the channel can have an overhang 447 that can be configured to prevent the bead 448 from leaving the channel 445 unless the bead 448 is advance sufficiently far distally to clear the overhang 447.

Figure 18G:
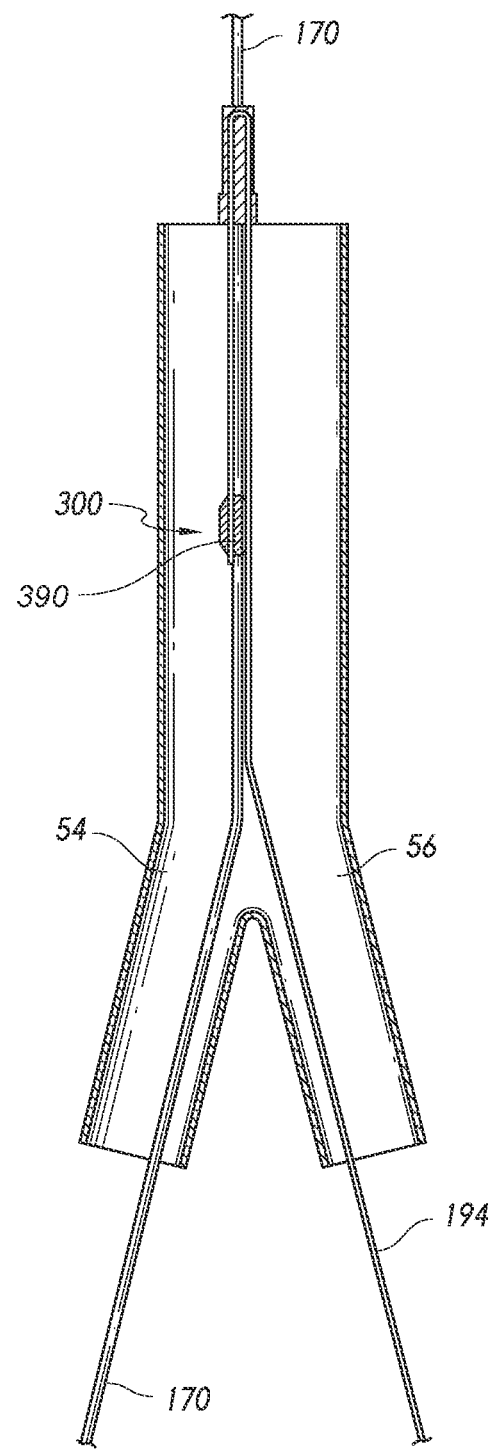
FIG. 18G is an alternative embodiment of the locking assembly presently disclosed.

FIG. 18G depicts an embodiment of the locking assembly 300 having a plastic retention member 390 (e.g., soft wing) that can be located within the main branch portion 52 of the graft 50. The plastic retention member 390 can interface (e.g., by friction, press fit, molded, adhered, thermally bonded, mechanically locked, otherwise secured) with the central tube 170. The contralateral guidewire 194 can extend distally through the graft 50, pass over or through a housing member and bend proximally back into the graft 50 to terminate at the plastic retention member 390. The locking portion 194b of the contralateral guidewire 194 can be configured to be retained by the plastic retention member 390 as described above in FIG. 18B.

Figure 18H:
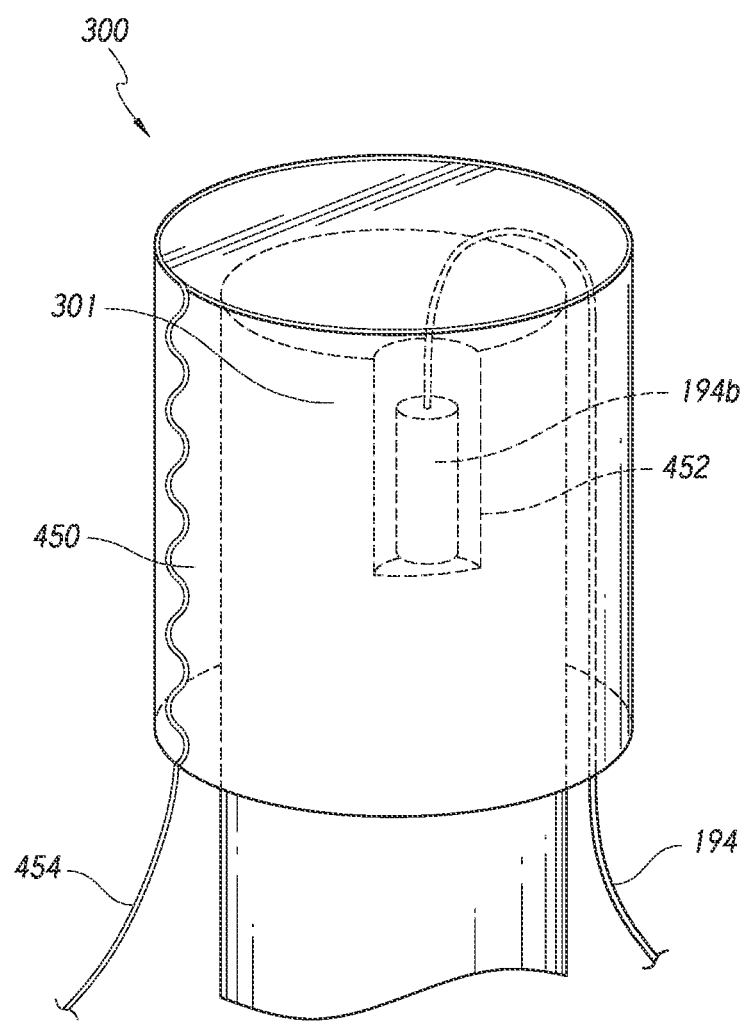
FIG. 18H is an alternative embodiment of the locking assembly presently disclosed.

FIG. 18H depicts an embodiment of the locking assembly 300 having a wrapper 450. The wrapper 450 can enclose at least a portion of the housing 301 of the locking assembly 300. The wrapper 450 can be configured to restrain the locking portion 194*b* of the contralateral guidewire 194 within a channel 452 formed in the side of the housing 301. The wrapper 450 can be removed by a control suture 454, thereby allowing the locking portion 194*b* to escape the channel 452.

Figure 18I:
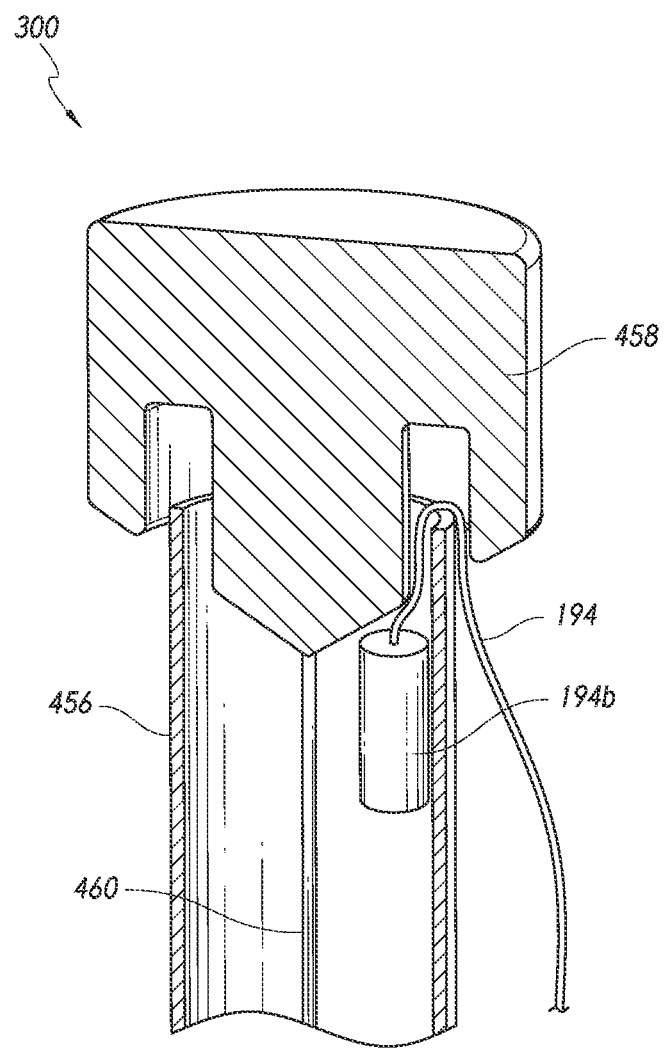
FIG. 18I is an alternative embodiment of the locking assembly presently disclosed.
Figure 18J:
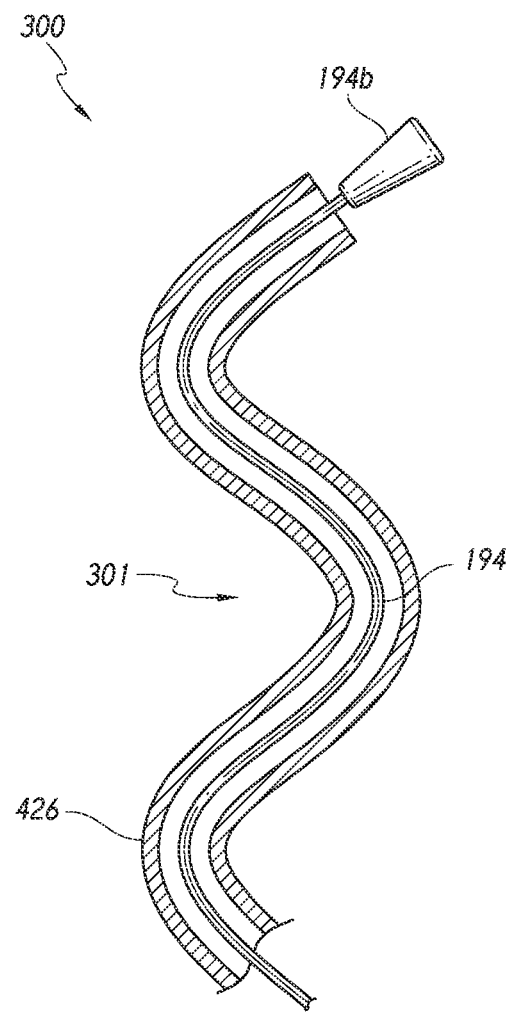
FIG. 18J is an alternative embodiment of the locking assembly presently disclosed.

FIG. 18I depicts an embodiment of the locking assembly 300 having a rigid sheath 456. The rigid sheath 456 can be configured to press the contralateral guidewire 194 against an abutment 458, thereby locking the contralateral guidewire 194 to the locking assembly 300. The contralateral guidewire 194 may be decoupled from the locking assembly 300 by proximally withdrawing the rigid sheath 456 or distally advancing the abutment 458. A control rod 460 attached to the abutment 458 can allow a user to distally advance the abutment 458. The locking portion 194*b* may be larger and/or more rigid than a remaining portion of the contralateral guidewire 194 locking portion FIG. 18J depicts an embodiment of the locking assembly 300 having a curved groove 462. The curved groove 462 may be S-shaped, U-shaped, sinusoidal, zig-zag-shaped or combinations thereof. The curved groove 462 may be formed in the outer surface of the housing 301 of the locking assembly 300 described above. The contralateral guidewire 194 may include a locking portion 194*b* that has a width or length that prevents the locking portion 194*b* from being pulled through the curved groove 462. The locking assembly 300 can be configured so that when the contralateral guidewire 194 is advanced distally the locking portion 194*b* of the contralateral guidewire 194 may peel out of the housing 301, thereby freeing the contralateral guidewire 194 from the locking assembly. Additionally or alternatively, the locking assembly 300 may be configured so that a release member 311 is advanced over the contralateral guidewire 194 to assist in freeing the contralateral guidewire 194 from the locking assembly 300.

Figure 18K:
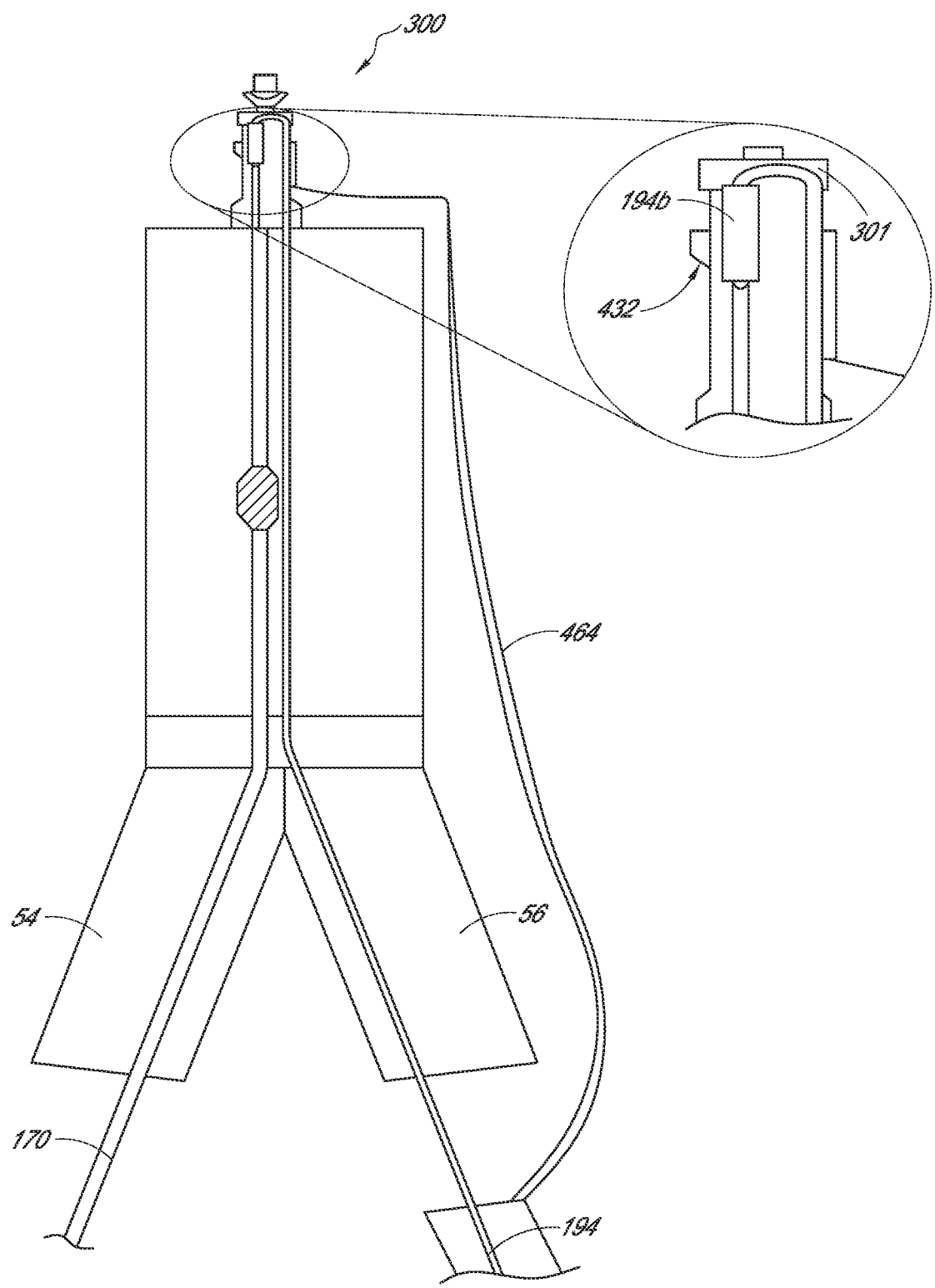
FIG. 18K is an alternative embodiment of the locking assembly presently disclosed.

FIG. 18K depicts an embodiment of the locking assembly 300 having an extended portion 464 of the contralateral branch sheath 190. The extended portion 464 may wrap around a portion of the locking assembly 300, thereby retaining the locking portion 194*b* of the contralateral guidewire 194 within a pocket 432 of the locking assembly 300. The extended portion 464 may be held closed by a suture. The suture can be coupled to the contralateral branch sheath 190. The suture can be configured to separate the extended portion 464 from the housing 301 as the contralateral branch sheath 190 is proximally withdrawn, thereby freeing the locking portion 194*b* of the contralateral guidewire 194 from the locking assembly 300.

Figure 18L:
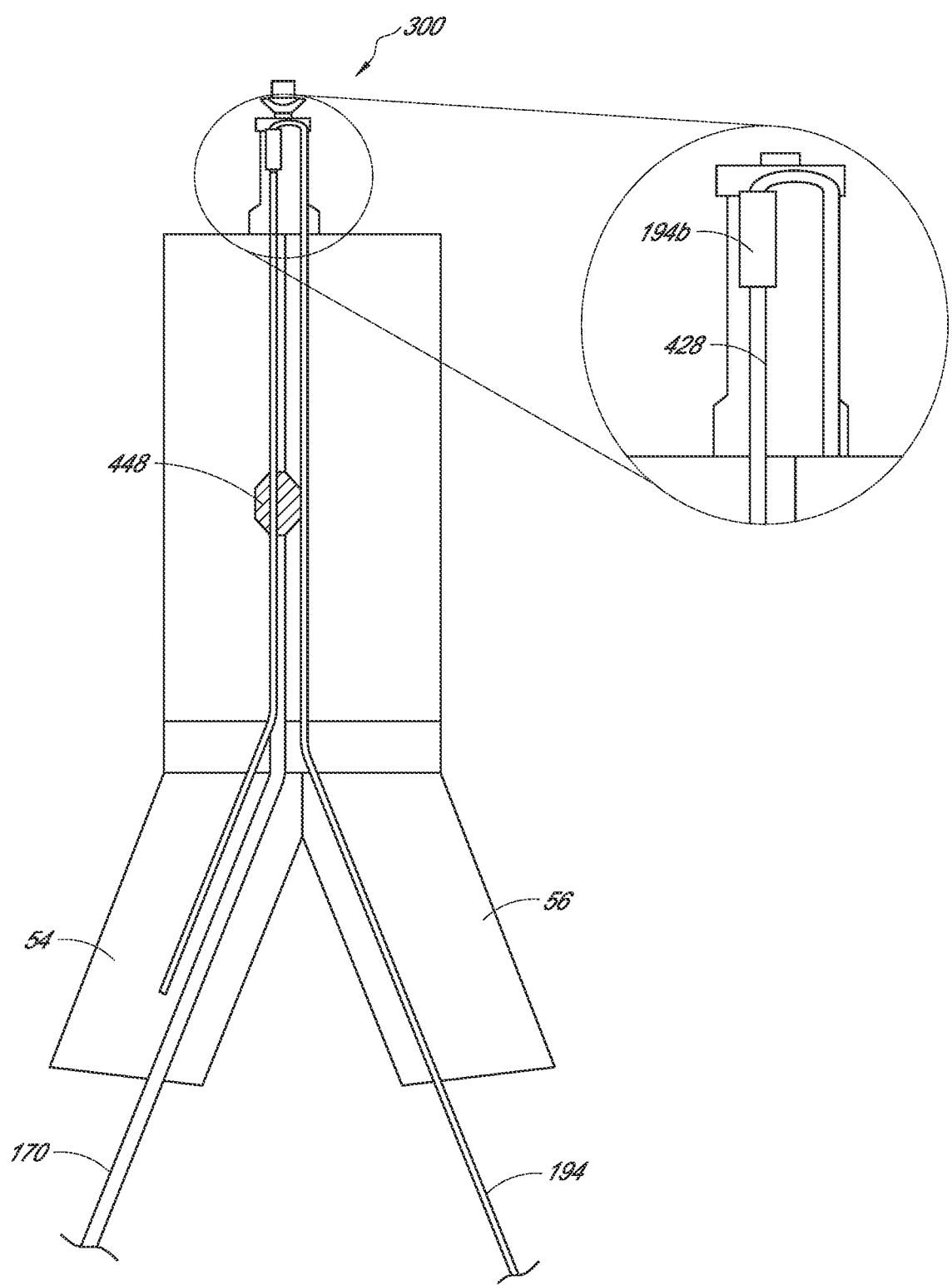
FIG. 18L is an alternative embodiment of the locking assembly presently disclosed.

FIG. 18L depicts an embodiment of the locking assembly 300 having a contralateral guidewire 194 that extends into the ipsilateral branch portion 54 of graft 50. The ipsilateral limb pinches, compresses, or otherwise provides friction such that the guidewire when inadvertently advanced does not disconnect from the catheter until the ipsilateral branch portion is deployed. The contralateral guidewire 194 may extend through a bead 448. The bead 448 may be configured to be retained within a channel 452 formed in the side of or through the housing 301 of the locking assembly 300 as described above.

Figure 18M:
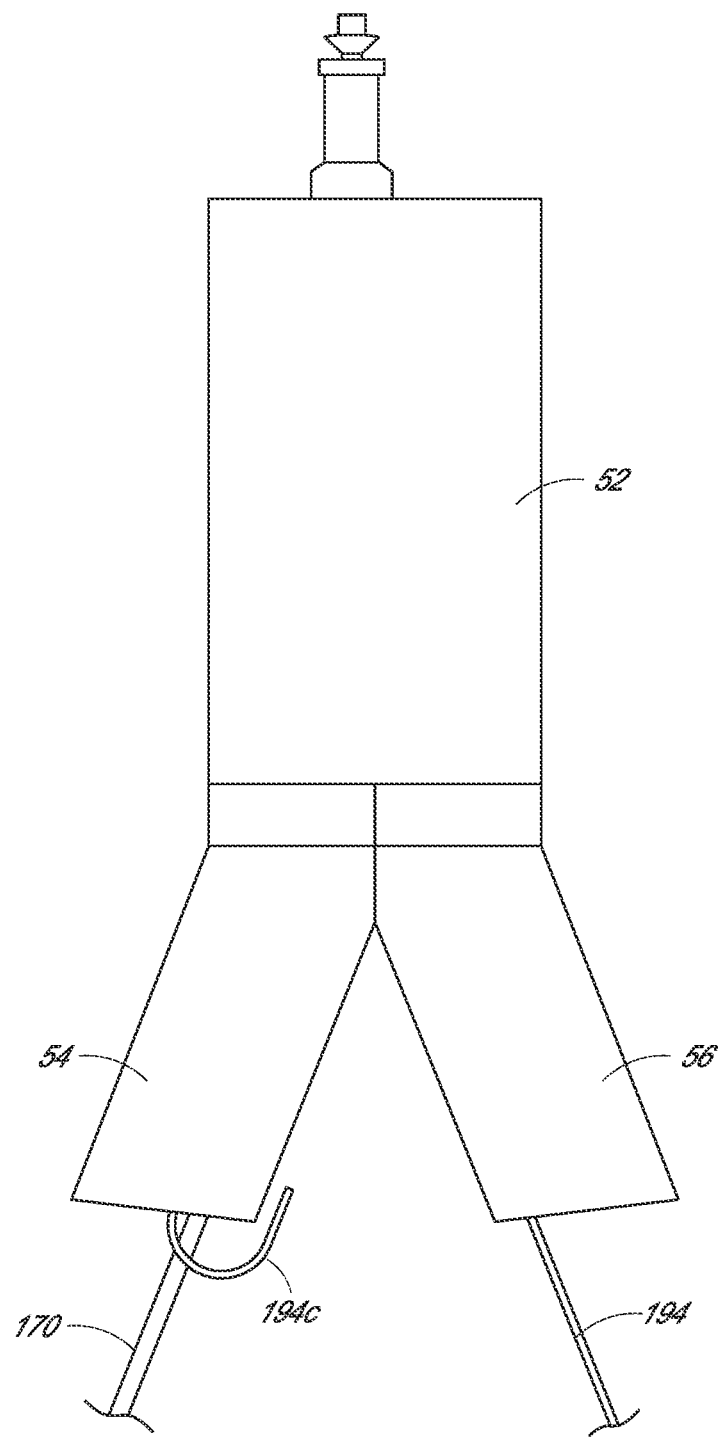
FIG. 18M is an alternative embodiment of the locking assembly presently disclosed.

FIG. 18M depicts an embodiment of the locking assembly 300 having a folded portion 194*c* of the contralateral guidewire 194 that is folded over the ipsilateral branch portion 54 of the graft 50. The folded portion 194*c* may be held against an outer surface of the ipsilateral branch portion 54 by the ipsilateral branch sheath 188. Retraction of the ipsilateral branch sheath 188 may then free the folded portion 194*c*, thereby allowing the contralateral guidewire 194 to be removed from the locking assembly 300.

Figure 18N:
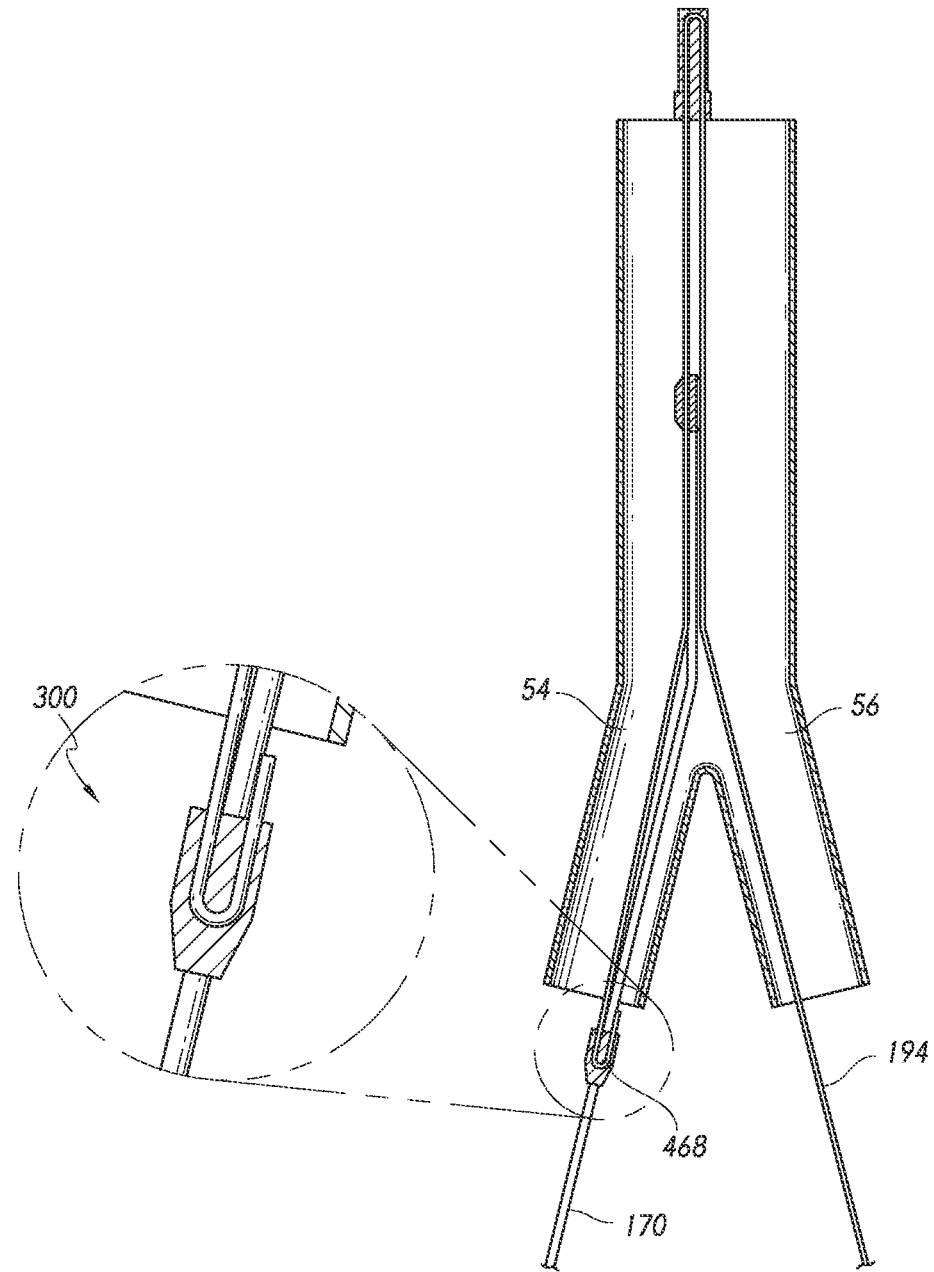
FIG. 18N is an alternative embodiment of the locking assembly presently disclosed.

FIG. 18N depicts an embodiment of the locking assembly 300 having ipsilateral locking member 468. The ipsilateral locking member 468 can include a channel 452 configured to retain a locking portion 194*b* or bead 448 that is coupled to the contralateral guidewire 194, as discussed above.

Figure 18O:
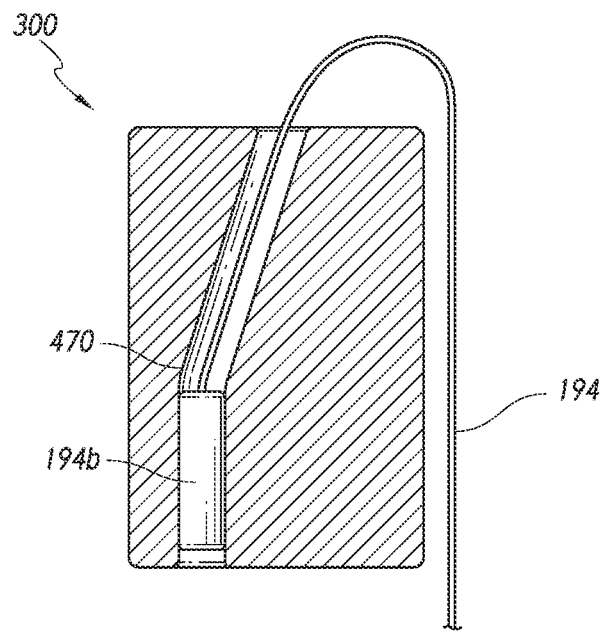
FIG. 18O is an alternative embodiment of the locking assembly presently disclosed.

FIG. 18O depicts an embodiment of the locking assembly 300 having a bent channel 470. The bent channel 470 can be configured so that the locking portion 194*b* of the contralateral guidewire 194 is unable to navigate through the bent channel 470. The locking portion 194*b* of the contralateral guidewire 194 can be decoupled for the locking assembly 300 by advancing the locking portion 194*b* proximally through the bent channel 470.

Figure 18P:
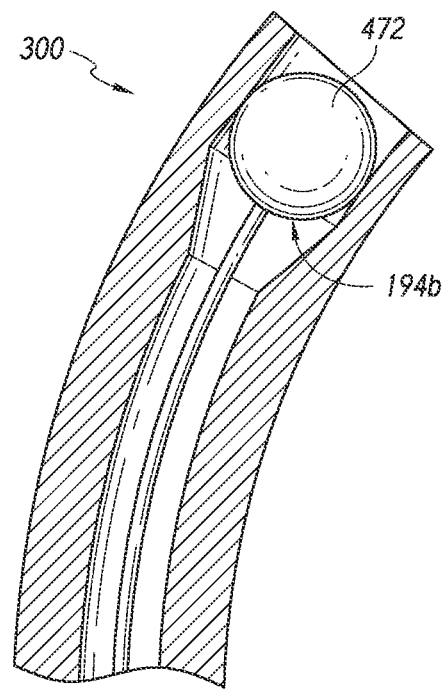
FIG. 18P is an alternative embodiment of the locking assembly presently disclosed.

FIG. 18P depicts an embodiment of the locking assembly 300 having a ball feature 472 at the locking portion 194*b* of the contralateral guidewire 194. The ball feature 472 can be configured to function similar to the bead 448 described above for FIG. 18F. The ball feature 472 may be configured to be too large to pass proximally through the channel of the locking assembly 300. The ball feature can be configured so that the locking portion 194*b* is freed from the locking assembly when the ball feature is advanced distally, thereby allowing the contralateral guidewire 194 to peel out of the channel in the locking assembly 300.

Figure 18Q:
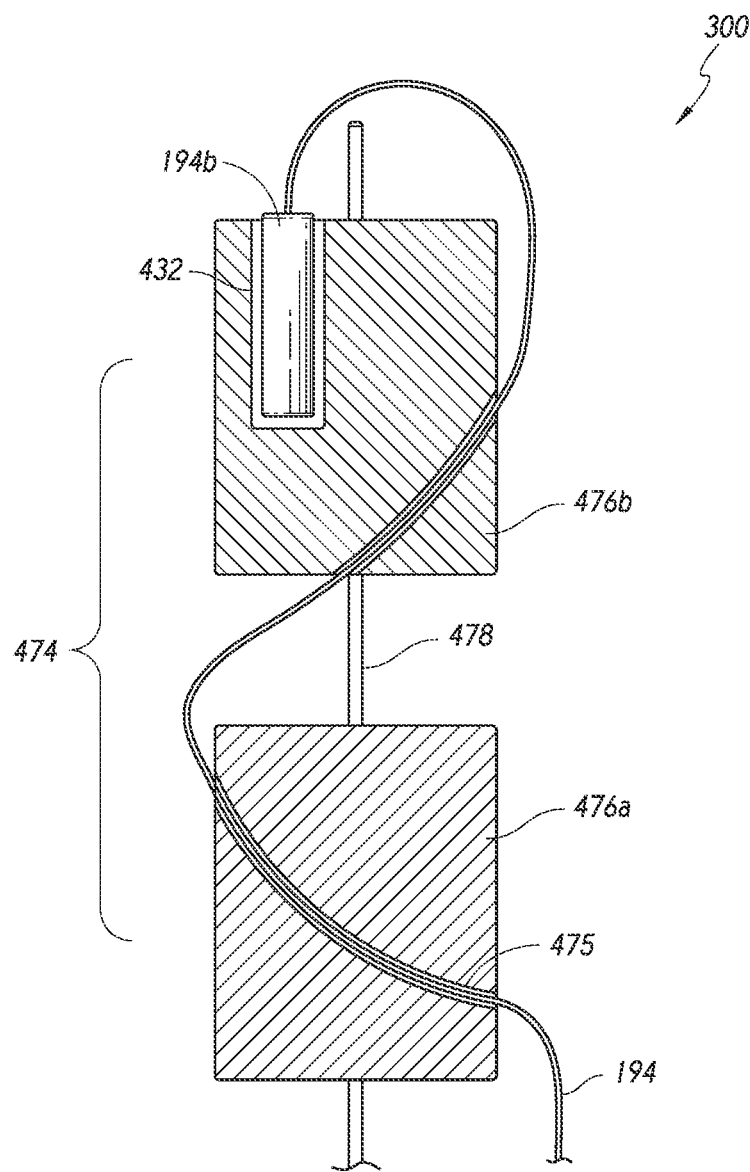
FIG. 18Q is an alternative embodiment of the locking assembly presently disclosed.

FIG. 18Q depicts an embodiment of the locking assembly 300 having a segmented locking channel 474. The segmented locking channel 474 may include a plurality of segments 476*a, b*, each having a groove 475 formed into the surface of the segment 476*a,b*. The segments 476*a,b* may be joined together by a coupling member 478. The contralateral guidewire 194 may navigate through the segmented locking channel 474. The locking portion 194*b* of the contralateral guidewire 194 may be retained within a pocket 432 that is formed in one of the segments 476*b* of the plurality of segments 476*a,b*.

Figure 18R:
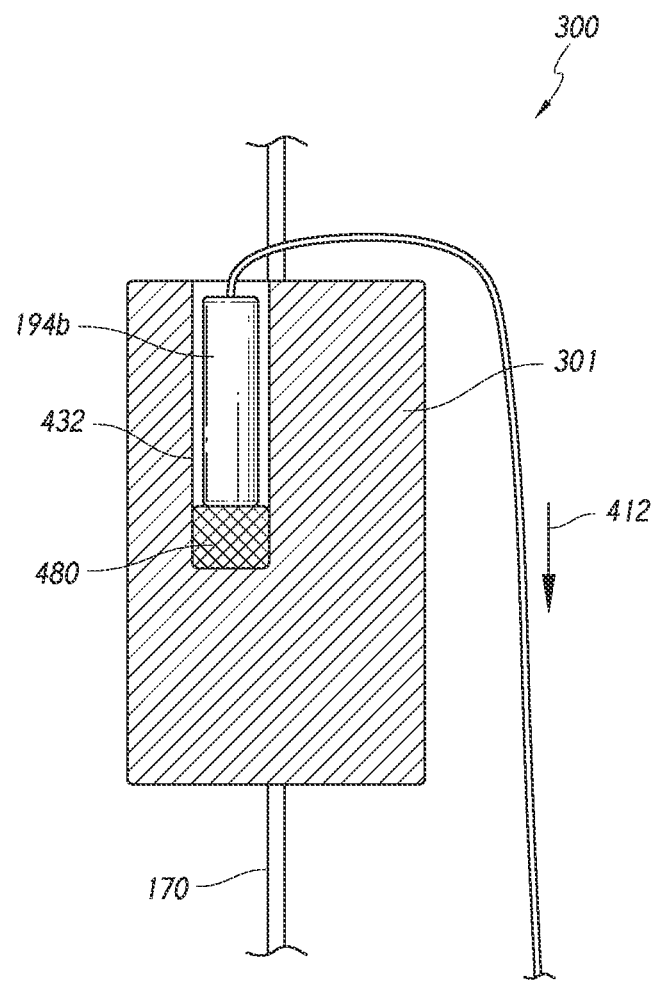
FIG. 18R is an alternative embodiment of the locking assembly presently disclosed.

FIG. 18R depicts an embodiment of the locking assembly 300 having a magnetic component 480. The magnetic component 480 can be disposed within the pocket 432 formed into the housing 301 of the locking assembly 300. The locking portion 194*b* of the contralateral guidewire 194 may include magnetic material that causes the locking portion 194*b* to be magnetically attracted to the magnetic member 180, thereby resisting upward forces 412 on the contralateral guidewire 194 from decoupling the locking portion 194*b* of the contralateral guidewire 194 from the locking assembly 300.

Figure 19:
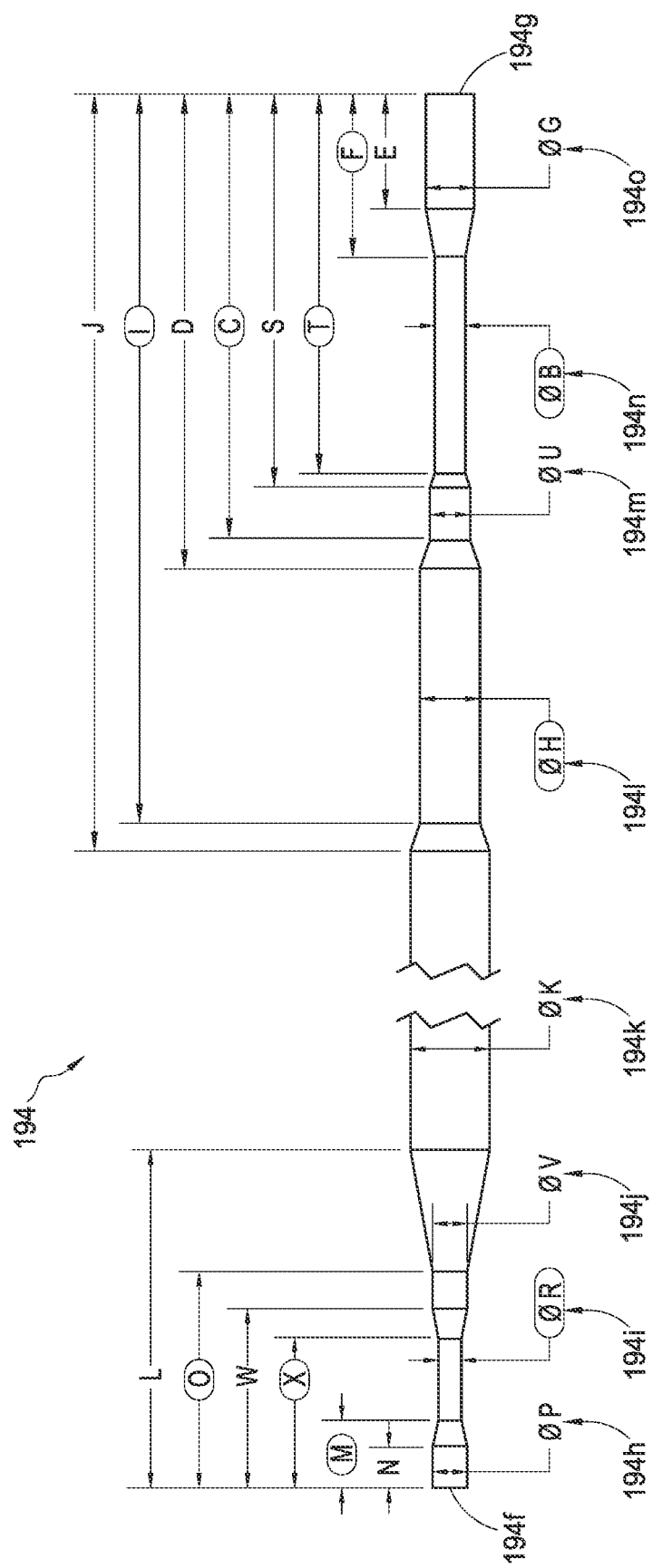
FIG. 19 is a side view of an embodiment of a contralateral guidewire.

FIG. 19 depicts a non-limiting exemplary embodiment of the contralateral guidewire 194. The contralateral guidewire 194 can be configured to include multiple regions that are joined together. The contralateral guidewire 194 can have a first end 194*f* and a second end 194*g*. The serial arrangement of the multiple regions of the contralateral guidewire can be varied according to the needs of the user. The serial arrangement of the regions of the contralateral guidewire 194 shown in FIG. 19 is illustrative only and not to be taken as limiting. The contralateral guidewire 194 can include a wire core, shrink tube made of suitable material (e.g., PTFE), adhesive, alloys containing platinum, and combinations thereof. The platinum alloys can contain 90% platinum and 10% iridium, or 92% platinum and 8% tungsten.

The contralateral guidewire 194 may include a distal coil made of wire containing platinum, e.g., at least about 90% platinum, at least about 92% platinum, at least about 95% platinum, or at least about 99% platinum. In some embodiments, the contralateral guidewire 194 can be constructed from about 92% platinum and 8% tungsten. The distal coil may be made of wire having an outer diameter of 0.003 inches. The distal coil may have a pitch of 0.003 inches. The distal coil may have a coil outer diameter of 0.025 inches. The distal coil may have a coil length of 8.0 cm with a tolerance of 0.3 cm.

The contralateral guidewire 194 may include a proximal coil made of wire containing 92% platinum and 8% tungsten. The proximal coil may be made of wire having an outer diameter of 0.003 inches. The proximal coil may have a pitch of 0.003 inches. The proximal coil may have a coil outer diameter of 0.025 inches. The proximal coil may have a coil length of 15.0 cm with a tolerance of 0.3 cm.

A first region 194*h* (denoted as having a diameter of P in FIG. 19) of the contralateral guidewire 194 can have a diameter of 0.0160 inches with a tolerance 0.0002 inches. The first region 194*h* can have a length of 0.3 cm with a tolerance of 0.1 cm. A second region 194*i* (denoted as having a diameter of R in FIG. 19) of the contralateral guidewire 194 can have a smaller diameter than the first region 194*h*, e.g., less than or equal to one-half the diameter of the first region 194*h*. For example, the diameter of the second region 194*i* can be about 0.0080 inches with a tolerance 0.0002 inches. The second region 194*i* can be longer than the first region 194*h*. For example, the second region 194*i* can have a length of 10.4 cm with a tolerance of 0.1 cm. A third region 194*j* (denoted as having a diameter of V in FIG. 19) of the contralateral guidewire 194 can have a larger diameter than the first and second regions 194*h*, 194*i*. For example, the diameter of the third region 194*j* can be about 0.0174 inches with a tolerance 0.0002 inches. The third region 194*j* can be longer than the first region 194*h* and/or shorter than the second region 194*i*. For example, the third region 194*j* can have a length of 1.0 cm with a tolerance of 0.1 cm. A fourth region 194*k* (denoted as having a diameter of K in FIG. 19) of the contralateral guidewire 194 can have a diameter greater than the first, second, and third regions 194*h*, 194*i*, 194*j*. For example, the fourth region 194*k* can have a diameter of about 0.0300 inches with a tolerance 0.0003 inches. A fifth region 194*l* (denoted as having a diameter of H in FIG. 19) of the contralateral guidewire 194 can have a diameter that is less than the diameter of the fourth region 194*k*, but greater than the diameter of the first, second, and third regions 194*h*, 194*i*, 194*j*. For example, the diameter of the fifth region 194*l* can be about 0.0210 inches with a tolerance 0.0002 inches. The fifth region 194*l* can be greater than each of the preceding regions 194*h*, 194*i*, 194*j*, 194*k*. For example, the fifth region 194*l* can have a length of 40.8 cm with a tolerance of 0.5 cm. A sixth region 194*m* (denoted as having a diameter of U in FIG. 19) of the contralateral guidewire 194 can have a diameter that is about the same as the diameter of the third region 194*j*. For example, the diameter of the sixth region 194*m* can be about 0.0174 inches with a tolerance 0.0002 inches. The sixth region 194*m* can be shorter than the can have a length of 0.8 cm with a tolerance of 0.1 cm. A seventh region 194*n* (denoted as having a diameter of B in FIG. 19) of the contralateral guidewire 194 can have a diameter that is about the same as the second region 194*i*. The diameter of the seventh region 194*n* may provide the smallest diameter of the contralateral guidewire 194. For example, the seventh region 194*n* can have a diameter of 0.0080 inches with a tolerance 0.0002 inches. The seventh region can have a length of 5.2 cm with a tolerance of 0.1 cm. An eighth region 194*o* (denoted as having a diameter of G in FIG. 19) of the contralateral guidewire 194 can have a diameter that is about the same as the diameter of the first region 194*h*. For example, the eighth region 194*o* can have a diameter of about 0.0160 inches with a tolerance 0.0002 inches. The eighth region 194*o* can have a length of 0.5 cm with a tolerance of 0.1 cm. The contralateral guidewire 194 may include transition regions that soften diameter changes in the contralateral guidewire 194. The transition regions may have a tapering angle that is formed between the longitudinal axis of the contralateral guidewire 194 and the outer wall of the transition region. The tapering angle of the transition regions can range between 10 and 60 degrees.

Terminology

While the above description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope. For example, while the delivery system is described with respect to deploying a bifurcated stent in the abdominal aortic, it is further envisioned that the delivery system could be used to deliver a prosthesis having a main portion and at least one branch portion, or alternatively a prosthesis having only a straight, main branch portion, to other branched intravascular vessels (e.g., the thoracic aorta and a cardiac artery) and leave a guidewire positioned through the expanded prosthesis.

The term "guidewire" is to be interpreted broadly and may include, in addition to its ordinary and customary meaning to a person of ordinary skill in the art, any elongate member. Although the disclosure herein describes a locking assembly for reversibly coupling a guidewire to a delivery system, the locking assembly can also be used to reversibly couple any elongate structure to the delivery system, catheter, or otherwise.

As used herein, the relative terms "proximal" and "distal" shall be defined from the perspective of the delivery system. Thus, proximal refers to the direction of the control end of the delivery system and distal refers to the direction of the distal tip.

Note that the terms "first" and "second" branch portion can be used interchangeably and to refer to any branch vessel in the body, including but not limited to the ipsilateral vessel, the contralateral vessel, radial vessels, and subclavian vessels. Accordingly, in some embodiments, the "first" branch portion can refer to any branch portion including but not limited to the vessels set forth above. Similarly, the "second" branch portion can refer to any branch portion including but not limited to the vessels set forth below.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," "generally," and "substantially" as used herein represent an amount close to the stated amount that still performs a desired function or achieves a desired result. For example, the terms "approximately", "about", and "substantially" may refer to an amount that is within less than 10% of the stated amount. As another example, in certain embodiments, the terms "substantially parallel" refer to a value, amount, or characteristic that departs from exactly parallel by less than or equal to 15 degrees.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "approximately 2 in." includes "2 in."

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that, achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "releasing the delivery system from the locked configuration" include "instructing release of the delivery system from the locked configuration."

EXAMPLE EMBODIMENTS

The following example embodiments identify some possible permutations of combinations of features disclosed herein, although other permutations of combinations of features are also possible.

1. A locking assembly for releasably coupling a first elongate structure to a second elongate structure, the locking assembly comprising:
   a housing comprising a proximal end, a distal end, and a lateral wall portion;
   a first lumen extending from the proximal end of the housing to the distal end of the housing and along a longitudinal axis of the locking assembly, the first lumen being configured to receive the first elongate structure;
   a second lumen extending from the distal end of the housing, a diameter of the second lumen being less than a diameter of the first lumen, the second lumen being configured to receive the second elongate structure; and
   a recessed portion extending at least partially through the housing, the recessed portion comprising at least one opening in the lateral wall portion of the housing.

2. The locking assembly of Embodiment 1, further comprising an elastomeric member in the recessed portion, the elastomeric member configured to retain the second elongate structure when the second elongate structure extends through the second lumen.

3. The locking assembly of Embodiment 2, wherein at least a portion of an outer surface of the elastomeric member is substantially flush with an outer surface of the lateral wall portion of the housing.

4. The locking assembly of Embodiment 2, or 3 wherein the elastomeric member comprises an opening at least partially aligned with the second lumen.

5. The locking assembly of Embodiment 4, wherein the opening comprises a diameter that is smaller than the diameter of the second lumen.

6. The locking assembly of any one of Embodiments 2 to 5, wherein the elastomeric member comprises silicone.

7. The locking assembly of any one of the preceding Embodiments, wherein a proximal portion of the housing is tapered.

8. The locking assembly of any one of the preceding Embodiments, further comprising a protruding portion extending along at least a portion of an outer periphery of a distal portion of the housing.

9. The locking assembly of Embodiment 8, wherein the second lumen is positioned between the first lumen and the protruding portion.

10. The locking assembly of any one of the preceding Embodiments, wherein the second lumen comprises a proximal portion, a distal portion, and an intermediate portion therebetween, a diameter of the intermediate portion being less than a diameter of the proximal portion and the distal portion.

11. A locking assembly for coupling a contralateral guidewire to an ipsilateral catheter, the locking assembly comprising:
an anchoring portion configured to engage the ipsilateral catheter; and
an interlock portion configured to retain a distal portion of the contralateral guidewire when the contralateral guidewire is advanced or retracted unless a vertical force of at least 0.1 lbf is applied to the contralateral guidewire.

12. The locking assembly of Embodiment 11, wherein the interlock portion comprises a lumen, the lumen being shaped to retain the contralateral guidewire when the contralateral guidewire is retracted.

13. The locking assembly of Embodiment 12, wherein the lumen comprises a distal portion, a proximal portion, and an intermediate portion therebetween, a diameter of the intermediate portion being less than a diameter of the distal portion and a diameter of the proximal portion.

14. The locking assembly of any one of Embodiments 11 to 13, further comprising a retention member configured to frictionally retain the guidewire when the guidewire is advanced.

15. The locking assembly of Embodiment 14, wherein the retention member comprises an elastomeric material.

16. The locking assembly of Embodiment 14 or 15, wherein the retention member comprises an opening configured to receive the contralateral guidewire.

17. The locking assembly of any one of Embodiments 11 to 16, wherein the interlock portion is configured to release the contralateral guidewire when a force is applied to an intermediate portion of the contralateral guidewire at an angle of less than or equal to about 60 degrees from the distal portion of the guidewire in the interlock portion.

18. A system for reversibly securing a first elongate member to a second elongate member, the system comprising:
a first elongate member;
a second elongate member comprising a proximal portion and a distal portion; and
a locking assembly fixed to the first elongate member, the locking assembly comprising:
a housing comprising a proximal end and a distal end;
a lumen extending from the distal end of the housing and through at least a portion of the housing, the second lumen being configured to receive the second elongate member from a distal side of the locking assembly;
a recessed portion extending at least partially through the housing; and
an elastomeric member in the recessed portion, the elastomeric member configured to retain the distal portion of the second elongate member when the second elongate member extends through the second lumen.

19. The system of Embodiment 18, wherein the second elongate member comprises a first region and a second region, the first region having a first stiffness, the second region having a second stiffness, the first stiffness being greater than the second stiffness.

20. The system of Embodiment 19, wherein the first region is distal to the second legion.

21. The system of Embodiment 19, wherein the first region is at a distal end of the second elongate member.

22. The system of Embodiment 18 or 19, further comprising a sheath configured to be advanced along the second elongate member and disengage the second elongate member from the recessed portion.

23. The system of Embodiment 18 to 22, wherein the second elongate member is a guidewire.

24. The system of any one of Embodiments 18 to 23, wherein the first elongate member is a catheter.

25. The system of any one of Embodiments 18 to 24, wherein the second lumen comprises a proximal portion, a distal portion, and an intermediate portion therebetween, a diameter of the intermediate portion being less than a diameter of the distal portion and a diameter of the proximal portion.

26. The system of any one of Embodiments 18 to 25, wherein the recessed portion comprises at least one opening in a lateral wall of the housing.

27. The system of any one of Embodiments 18 to 26, wherein the elastomeric member comprises an opening at least partially aligned with the second lumen.

28. The locking assembly of Embodiment 27, wherein the opening comprises a diameter that is smaller than the diameter of the second lumen.

29. The locking assembly of any one of Embodiments 18 to 28, wherein the elastomeric member comprises silicone.

30. The locking assembly of any one of Embodiments 18 to 29, further comprising a protruding portion extending along at least a portion of an outer periphery of a distal portion of the housing.

31. A method for releasing a contralateral guidewire from an ipsilateral catheter, the method comprising:
advancing a delivery system in a locked configuration, the delivery system comprising a locking assembly fixed to the ipsilateral catheter, the locking assembly comprising an interlock portion configured to retain the guidewire when the delivery system is in the locked configuration, a distal end of the guidewire being introduced into the interlock portion from a distal side of the locking assembly such that the guidewire comprises a bend when the delivery system is in the locked configuration, the bend being positioned between a proximal portion of the guidewire and the distal portion of the guidewire; and
releasing the delivery system from the locked configuration to the unlocked configuration by advancing a release catheter along the guidewire.

32. The method of Embodiment 31, wherein in the locked configuration, the interlock portion is configured to retain the guidewire when the guidewire is retracted.

33. The method of Embodiment 31 or 32, wherein before advancing the release catheter, the interlock portion is configured to retain the guidewire when the guidewire is advanced.

34. The method of any one of Embodiments 31 to 33, wherein releasing the delivery system comprises applying a force to the guidewire at an angle of less than or equal to about 60 degrees from a longitudinal axis of the locking assembly.

What is claimed is:
1. A locking assembly, comprising:
a housing comprising a proximal end, a distal end, and a lateral wall portion;
a first lumen extending from the proximal end of the housing to the distal end of the housing;
an elongated structure;

a second lumen extending from the distal end of the housing, said second lumen having a first diameter and a second diameter, the second diameter being smaller than the first diameter, the first or second diameter of the second lumen being smaller than a diameter of the first lumen, the second lumen being configured to releasably receive the elongated structure; and a sheath configured to be advanced along the elongated structure and disengage the elongated structure from the second lumen.

2. The locking assembly of claim 1, further comprising a recessed portion and an elastomeric member in the recessed portion, the elastomeric member configured to retain the elongated structure when the elongated structure extends through the second lumen.

3. The locking assembly of claim 2, wherein at least a portion of an outer surface of the elastomeric member is substantially flush with an outer surface of the lateral wall portion of the housing.

4. The locking assembly of claim 2, wherein the elastomeric member comprises an opening at least partially aligned with the second lumen.

5. The locking assembly of claim 4, wherein the opening comprises a diameter that is smaller than the first diameter of the second lumen.

6. The locking assembly of claim 1, further comprising a protruding portion extending along at least a portion of an outer periphery of a distal portion of the housing.

7. The locking assembly of claim 6, wherein the second lumen is positioned between the first lumen and the protruding portion.

8. The locking assembly of claim 1, wherein the second lumen comprises a proximal portion, a distal portion, and an intermediate portion therebetween, a diameter of the intermediate portion being less than a diameter of the proximal portion and the distal portion.

9. A device comprising the locking assembly of claim 1, further comprising an additional elongated structure.

10. The device of claim 9, wherein the first lumen is configured to receive the additional elongated structure.

11. A locking assembly for releasably coupling a contralateral guidewire to an ipsilateral catheter, the locking assembly comprising:

a housing comprising a first lumen and a second lumen;

the contralateral guidewire;

the second lumen configured to retain a distal portion of the contralateral guidewire; and a sheath configured to be advanced along the contralateral guidewire and disengage the contralateral guidewire from the second lumen.

12. The locking assembly of claim 11, wherein the second lumen being shaped to retain the contralateral guidewire when the contralateral guidewire is retracted.

13. The locking assembly of claim 12, wherein the second lumen comprises a distal portion, a proximal portion, and an intermediate portion therebetween, a diameter of the intermediate portion being less than a diameter of the distal portion and a diameter of the proximal portion.

14. The locking assembly of claim 11, further comprising a retention member configured to frictionally retain the contralateral guidewire when the contralateral guidewire is advanced.

15. The locking assembly of claim 14, wherein the retention member comprises an opening configured to receive the contralateral guidewire.

16. The locking assembly of claim 11, wherein the second lumen is configured to release the contralateral guidewire when a force is applied to an intermediate portion of the contralateral guidewire.

17. The locking assembly of claim 11, wherein the second lumen is configured to retain the distal portion of the contralateral guidewire when the contralateral guidewire is advanced or retracted relative to the housing unless a vertical force between about 0.01 and about 6.0 lbf is applied to the contralateral guidewire.

18. A device comprising the locking assembly of claim 11 further comprising the ipsilateral catheter.

19. A system for releasably securing a first elongate member to a second elongate member, the system comprising:

the first elongate member, the second elongate member;

a housing;

a first housing lumen extending within the housing and configured to receive the first elongate member;

a second housing lumen extending within the housing and configured to receive the second elongate member; and a sheath configured to be advanced along the second elongate member and disengage the second elongate member from the second housing lumen.

20. The system of claim 19, wherein the second elongate member comprises a first region and a second region, the first region having a first stiffness, the second region having a second stiffness, the first stiffness being greater than the second stiffness.

* * * * *